United States Patent
Benghezal et al.

(10) Patent No.: US 8,715,929 B2
(45) Date of Patent: May 6, 2014

(54) SYNTHETIC OPERON

(75) Inventors: Mohammed Benghezal, Scarborough (AU); Yakhya Dieye, Nollamara (AU); Carola Schwann, Huntingdale (AU); Miriam Sehnal, Scarborough (AU); Alma Fulurija, White Gum Valley (AU); Barry J. Marshall, Subiaco (AU)

(73) Assignee: Ondek Pty. Ltd., Rushcutters Bay (AU)

( * ) Notice: Subject to any disclaimer, the term of this patent is extended or adjusted under 35 U.S.C. 154(b) by 0 days.

(21) Appl. No.: 13/380,736

(22) PCT Filed: Jun. 25, 2010

(86) PCT No.: PCT/AU2010/000806
§ 371 (c)(1),
(2), (4) Date: May 15, 2012

(87) PCT Pub. No.: WO2010/148459
PCT Pub. Date: Dec. 29, 2010

(65) Prior Publication Data
US 2012/0225454 A1    Sep. 6, 2012

(30) Foreign Application Priority Data

Jun. 26, 2009 (AU) ................ 2009902990

(51) Int. Cl.
*C12Q 1/68* (2006.01)
*C12P 21/06* (2006.01)

(52) U.S. Cl.
USPC ..................................... 435/6.1; 435/69.1

(58) Field of Classification Search
USPC ............................... 435/69.1, 6.1
See application file for complete search history.

(56) References Cited

U.S. PATENT DOCUMENTS 6,570,004 B1    5/2003    Blaser et al.
2002/0161192 A1    10/2002    Meyer et al.

FOREIGN PATENT DOCUMENTS

WO    WO2006/015445    2/2006
WO    WO2008/055316    5/2008
WO    WO 2008/131359    10/2008

OTHER PUBLICATIONS

Marshall and Schoep "Helicobacter pylori as a Vaccine Delivery System," Helicobacter 12:75-79, 2007.
Matic et al., "Development of Non-Antibiotic-Resistant, Chromosomally Based, Constitutive and Inducible Expression Systems for aroA-Attenuated Salmonella enterica Serovar Typhimurium," Infection and Immunity 77:1817-1826, 2009.
International Search Report; PCT/AU2010/000806; Sep. 10, 2010; (4 pages).
Hernando-Rico et al.; "Structure of the ask-asd operon and formation of aspartokinase subunits in the cephamycin producer 'Amycolatopsis lactamdurans'."; Microbiology, vol. 147, No. 6, Jun. 1, 1998; pp. 1547-1555.
Hofreuter et al.; "Natural competence for DNA transformation in Helicobacter pylori : identification and genetic characterization of the comβ locus"; Molecular Microbiology, vol. 28, No. 5; Jun. 1, 1998; pp. 1027-1038.
Suerbaum et al.; "Helicobacter pylori HSPA-HSPB heat-shock gene cluster: nucleotide sequence, expression, putative function and immunogenicity"; Molecular Microbiology, vol. 14, No. 5; Jan. 1, 1994; pp. 959-974.
Porwollik et al.; "Molecular characterization of a flagellar export locus of Helicobacter pylori"; Infection and Immunity, vol. 67, No. 5, May 1, 1999; pp. 2060-2070.
McClain et al.; Amino-Terminal hydrophobic region of Helicobacter pylori vacuolating cytotoxin (VacA) mediates transmembrane protein dimerization; Infection and Immunity, vol. 69, No. 2; Feb. 1, 2001; pp. 1181-1184.
Letley et al.; "Determinants of Helicobacter pylori vacuolating cytotoxin production analysed by construction of vacA hybrids and by site-directed mutagenesis", Gastroenterology, vol. 114, Apr. 15, 1998; pp. A1020-A1021.
Supplemental European Search Report; EP 10 791 078.8; Oct. 24, 2012; 12 pages.
EP Communication; EP 10 791 078.8; Jun. 14, 2013; 9 pages.
Ladeira, et al.; "Relationship among oxidative DNA damage, gastric, ucosal density and the relevance of cagA, vacA and iceA genotypes of Helicobacter pylori"; Dig Dis Sci, 2008; vol. 53, pp. 248-255.
Blaser; "Role of vacA and the cagA locus of Helicobacter pylori in human disease"; Alimentary Pharmacology & Therapeutics; 1996; vol. 10, No. suppl. 01; pp. 73-77.

*Primary Examiner* — Maryam Monshipouri
(74) *Attorney, Agent, or Firm* — Fish & Richardson P.C.

(57) ABSTRACT

The present invention relates to synthetic operons. In particular, the present invention relates to a synthetic operon for integration into a bacterial chromosome of a bacterium comprising a promoter operably-linked to at least two genes, wherein at least one gene is a gene of interest and at least one gene is a gene essential to said bacterium.

9 Claims, 29 Drawing Sheets

```
cacctgacgcgccctgtagcggcgcattaagcgcggcgggtgtggtggttacgcgcagcgtgaccgctacacttgccagcgccctagcgcccgctcctttcgcttt
cttccttcctttctcgccacgttcgccggctttccccgtcaagctctaaatcggggggctcccttttagggttccgatttagtgcttttacggcacctcgaccccaaaaaact
tgattagggtgatggttcacgtagtgggccatcgccctgatagacggttttttcgcccttttgacgttggagtccacgttctttaatagtggactcttgttccaaactggaac
aacactcaaccctatctcggtctattcttttgatttataagggattttgccgatttcggcctattggttaaaaaatgagctgatttaacaaaaatttaacgcgaattttaacaa
aatattaacgcttacaatttccattcgccattcaggctgcgcaactgttgggaagggcgatcggtgcgggcctcttcgctattacgccagctggcgaaaggggatgt
gctgcaaggcgattaagttgggtaacgccagggttttcccagtcacgacgttgtaaaacgacggccagtgaattgtaatacgactcactatagggcgaattgggtac
cgggccccccctcgatcgacggtatcgataagcttagcactaccttgacatggtagtggccgctggttcaagtccagtcgtggccaccattatcactccaattttaatt
ctcattttttttgcgagttttttgatctttataaattctaaaggggtattaaacgcacttctaataacgatttttatagcgcttcaaagatataacactaattcattttaaataataatta
gttaatgaacgcttctgttaatcttagtaaatcaaaacattgctacaattacatccaaccttgatttcgttatgtcttcaaggaaaaacactttaagaataggagaataagat
gaaactcaccccaaaagagttagacaagttgatgctccactatgctggagaattggctaaaaaacgcaaagaaaaaggcattaagcttaactatgtagaagcggta
gctttgattagtgcccatattatggaagaagcgagagctggtaaaaagactgcggctgaattgatgcaagaagggcgcactctttttaaaaccggatgatgtgatggat
ggcgtggcaagcatgatccatgaagtgggtattgaagcgatgtttcctgatgggacaaaactcgtaaccgtgcataccccctattgaggccaatggtaaattagttcct
ggtgagttgttcttaaaaaatgaagacatcactatcaacgaaggcaaaaaaagccgttagcgtgaaagttaaaaatgttggcgacagaccggttcaaatcggctcaca
cttccattcttgaagtgaatagatgcttagactttgacagagaaaaaactttcggtaaacgcttagacattgcgagcgggacagcggtaaggtttgagcctggcgaa
gaaaaatccgtagaattgattgacattggcggtaacagaagaatctttggatttaacgcgttggttgataggcaagcagacaacgaaagcaaaaaaattgctttacac
agagctaaagagcgtggttttcatggcgctaaaagcgatgacaactatgtaaaaacaattaaggagtaagaattcagatctgaaatgaaaaagattagcagaaaga
atatgtttctatgtatgccctactacaggcgataaagtgagattgggcgatacagacttgatcgctgaagtagaacatgactacaccatttatggcgaagagcttaaat
tcggtggcggtaaaaccctgagagaaggcatgagccaatccaacaaccctgcaaagaagaattggatctaatcatcactaacgctttaatcgtggattacaccggt
atttataaagcggatattggtattaaagatggcaaaatcgctggcattggtaaaggcggtaacaaagacatgcaagatggcgttaaaaacaatcttagcgtaggtcct
gctactgaagccttagccggtgaaggtttgatcgtaactgctggtggtattgacacacacatccacttcatttcaccccaacaaatccctacagcttttgcaagcggtgt
aacaaccatgattggtggcggaactggtcctgctgatggcactaatgcgactactatcactccaggcagaagaaatttaaaatggatgctcagagcggctgaagaat
attctatgaacttaggtttcttggctaaaggtaacgcttctaacgacgcgagcttagccgatcaaattgaagctggtgcgattggctttaaaatccacgaagactgggg
caccactcctctgcaatcaatcatgcgttagatgttgcagacaaatacgatgtgcaagtcgctatccacacagacactttgaatgaagccggttgcgtggaagacac
tatgcacagctattgccggacgcactatgcacactttccacactgaaggtgctggcggcggacacgctcctgatattattaaagtagctggtgaacacaacattcttccc
gcttccactaaccccactatcccttttcactgtgaatacagaagcagaacacatggacatgcttatggtgtgccaccacttggataaaagcattaaagaagatgttcagtt
cgctgattcaaggatcctctagagcggccgccaccgcggtggagctccagcttttgttccctttagtgagggttaatttcgagcttggcgtaatcatggtcatagctgtt
tcctgtgtgaaattgttatccgctcacaattccacacaacatacgagccgcagcatcaaagtgtaaagcctggggtgcctaatgagtgagctaactcacattaattgcg
ttgcgctcactgcccgctttccagtcgggaaacctgtcgtgccagctgcattaatgaatcggccaacgcgcggggagaggcggtttgcgtattgggcgctcttccgc
ttcctcgctcactgactcgctgcgctcggtcgttcggctgcggcgagcggtatcagctcactcaaaggcggtaatacggttatccacagaatcaggggataacgca
ggaaagaacatgtgagcaaaaggccagcaaaaggccaggaaccgtaaaaaggccgcgttgctggcgtttttccataggctccgcccccctgacgagcatcacaa
aaatcgacgctcaagtcagaggtggcgaaacccgacaggactataaagataccaggcgtttccccctggaagctccctcgtgcgctctcctgttccgaccctgccg
cttaccggatacctgtccgcctttctcccttcgggaagcgtggcgctttctcatagctcacgctgtaggtatctcagttcggtgtaggtcgttcgctccaagctgggctgt
gtgcacgaaccccccgttcagcccgaccgctgcgccttatccggtaactatcgtcttgagtccaacccggtaagacacgacttatcgccactggcagcagccactg
gtaacaggattagcagagcgaggtatgtaggcggtgctacagagttcttgaagtggtggcctaactacggctacactagaaggacagtatttggtatctgcgctctg
ctgaagccagttaccttcggaaaaagagttggtagctcttgatccggcaaacaaaccaccgctggtagcggtggtttttttgttggcaagcagcagattacgcgcaga
aaaaaaggatctcaagaagatcctttgatcttttctacggggtctgacgctcagtggaacgaaaactcacgttaagggattttggtcatgagattatcaaaaaggatctt
cacctagatcctttttaaattaaaaatgaagttttaaatcaatctaaagtatatatgagtaaacttggtctgacagttaccaatgcttaatcagtgaggcacctatctcagcga
tctgtctatttcgttcatccatagttgcctgactccccgtcgtgtagataactacgatacgggagggcttaccatctggccccagtgctgcaatgataccgcgagaccc
acgctcaccggctccagatttatcagcaataaaccagccagccggaagggccgagccgcagaagtggtcctgcaactttatccgcctccatccagtctattaattgttg
ccgggaagctagagtaagtagttcgccagttaatagtttgcgcaacgttgttgccattgctacaggcatcgtggtgtcacgctcgtcgtttggtatggcttcattcagct
ccggttcccaacgatcaaggcgagttacatgatccccatgttgtgcaaaaaagcggttagctccttcggtcctccgatcgttgtcagaagtaagttggccgcagtgtt
atcactcatggttatggcagcactgcataattctcttactgtcatgccatccgtaagatgcttttctgtgactggtgagtactcaaccaagtcattctgagaatagtgtatgc
ggcgaccgagttgctcttgcccggcgtcaatacgggataataccgcgccacatagcagaactttaaaagtgctcatcattggaaaacgttcttcggggcgaaaactc
tcaaggatcttaccgctgttgagatccagttcgatgtaacccactcgtgcacccaactgatcttcagcatcttttactttcaccagcgtttctgggtgagcaaaaacagg
aaggcaaaatgccgcaaaaaagggaataagggcgacacggaaatgttgaatactcatactcttcctttttcaatattattgaagcatttatcagggttattgtctcatgag
cggatacatatttgaatgtatttagaaaaataaacaaataggggttccgcgcacatttccccgaaaagtgc
```

FIGURE 4 cacctgacgcgccctgtagcggcgcattaagcgcggcgggtgtggtggttacgcgcagcgtgaccgctacacttgccagcgccctagcgcccgctccttcgcttt
cttccctccttctcgccacgttcgccggcttcccgtcaagctctaaatcgggggctccctttaggttccgatttagtgctttacggcacctcgacccaaaaaact
tgattagggtgatggttcacgtagtgggccatcgccctgatagacggttttcgcccctttgacgttggagtccacgttcttaatagtggactcttgttccaaactggaac
aacactcaaccctatctcggtctattcttttgatttataagggattttgccgatttcggcctattggttaaaaaatgagctgatttaacaaaaatttaacgcgaattttaacaa
aatattaacgcttacaatttccattcgccattcaggctgcgcaactgttgggaagggcgatcggtgcgggcctcttcgctattacgccagctggcgaaaggggggatgt
gctgcaaggcgattaagttgggtaacgccagggttttcccagtcacgacgttgtaaaacgacggccagtgaattgtaatacgactcactatagggcgaattgggtac
cggggcccccctcgatcgacggtatcgataagcttcatgcgttagatgttgcagacaaatacgatgtgcaagtcgctatccacacagacactttgaatgaagccggtt
gcgtggaagacactatggcagctattgccggacgcactatgcacactttccacactgaaggtgctggcggcggacacgctcctgatattattaaagtagctggtgaa
cacaacattcttcccgcttccactaaccccactatccctttcactgtgaatacagaagcagaacacatggacatgcttatgtgtgccaccacttggataaaagcattaa
agaagatgttcagttcgctgattcaaggatccgccctcaaaccattgcggctgaagacactttgcatgacatgggatttctcaatcaccagctctgactctcaagcta
tgggtcgtgtgggtgaagttatcactagaacttggcaaacagctgacaaaaacaaaaaagaatttggccgcttgaaagaagaaaaaggcgataacgacaacttcag
gatcaaacgctacttgtctaaatacaccattaacccagcgatcgctcatgggattagcgagtatgtaggttctgtagaagtgggcaaagtggctgacttggtattgtgg
agtcccgcattctttggcgtaaaacccaacatgatcatcaaaggcgggttcattgcgttgagtcaaatgggtgacgcgaacgcttctatccctaccccacaaccagttt
attacagagaaatgttcgctcatcatggtaaagccaaatacgatgcaaacatcacttttgtgtctcaagcggcttatgacaaaggcattaaagaagaattagggcttga
aagacaagtgttgccggtaaaaaattgcagaaacatcactaaaaaagacatgcaattcaacgacacactaccgctcacattgaagtcaatcctgaaacttaccatgtgtt
cgtggatggcaaagaagtaacttctaaaccagccaataaagtgagcttggcgcaactctttagcattttctaggattttttaggagcaacgctccttaaatccttagttttt
agctctctgattttttgtttatcaaaaaattgggggctttttttgtgaattcagatctttttatttttttgtcaatttactattttctttatgattagctcaagcaacaaaagttattcgta
aggtgcgtttgttgtaaaaattttttgtttggaaggaaaaggcaatgctaggacttgtattgttatatgttgggattgttttaatcagcaatgggatttgcgggttaaccaaag
tcgatcctaaaagcactgcggtgatgaactttttgtgggcggactttccattatttgtaatatagttgtcatcacttattctgcactccaccctacagccctgtagaaggt
gctgaagatattgctcaagtatcgcaccatttgactagtttctatggaccagcgactgggttattgtttggtttcacctacttgtatgcggctatcaaccacactttggtttg
gattggaggccctactcttggtatagcttattcgtagcgatcaacacgattcctgctgcgattttatcccactatagcgatatgcttgatgaccacaaagtgttaggcatc
actgaaggcgattggtgggcgatcatttggttggcttggggtgttttgtggcttaccgctttcattgaaaacatcttgaaaatccctttaggaaattcactccatggcttg
ctatcattgagggtattttaaccgcttggatccctgcttggttgctctttatccaacactgggtgtgagatgatcatagagcgtttagttggcaatctaaggattaaacc
ccttggatttcagcgtggatcatgtggatttggaatggtttgaaacgaggaaaaaaatcgctcgtttttaaaaccaggcaaggcaaagacatagccatacgccttaaag
acgctcccaagttggggctctctcaagggatattttatttaaagaagagaaggaaattatcgccgttaatatcttggattctgaagtcattcacatcctctagagcggc
cgccaccgcggtggagctccagcttttgttcccttttagtgagggttaatttcgagcttggcgtaatcatggtcatagctgtttcctgtgtgaaattgttatccgctcacaatt
ccacacaacatacgagccggaagcataaagtgtaaagcctggggtgcctaatgagtgagctaactcacattaattgcgttgcgctcactgcccgctttccagtcggg
aaacctgtcgtgccagctgcattaatgaatcggccaacgcgcggggagaggcggtttgcgtattgggcgctcttccgcttcctcgctcactgactcgctgcgctcgg
tcgttcggctgcggcgagcggtatcagctcactcaaaggcggtaatacggttatccacagaatcaggggataacgcaggaaagaacatgtgagcaaaaggccag
caaaaggccaggaaccgtaaaaaggccgcgttgctggcgtttttccataggctccgcccccctgacgagcatcacaaaaatcgacgctcaagtcagaggtggcg
aaacccgacaggactataaagataccaggcgtttccccctggaagctccctcgtgcgctctcctgttccgaccctgccgcttaccggatacctgtccgcctttctccct
tcgggaagcgtggcgctttctcatagctcacgctgtaggtatctcagttcggtgtaggtcgttcgctccaagctgggctgtgtgcacgaacccccgttcagcccgac
cgctgcgccttatccggtaactatcgtcttgagtccaacccggtaagacacgacttatcgccactggcagcagccactggtaacaggattagcagagcgaggtatgt
aggcggtgctacagagttcttgaagtggtggcctaactacggctacactagaaggacagtatttggtatctgcgctctgctgaagccagttaccttcggaaaaagagt
tggtagctcttgatccggcaaacaaaccaccgctggtagcggtggttttttgtttgcaagcagcagattacgcgcagaaaaaaaggatctcaagaagatcctttgatc
ttttctacggggtctgacgctcagtggaacgaaaactcacgttaagggattttggtcatgagattatcaaaaaggatcttcacctagatccttttaaattaaaaatgaagtt
ttaaatcaatctaaagtatatatgagtaaacttggtctgacagttaccaatgcttaatcagtgaggcacctatctcagcgatctgtctatttcgttcatccatagttgcctga
ctccccgtcgtgtagataactacgatacgggagggcttaccatctggccccagtgctgcaatgataccgcgagacccacgctcaccggctccagatttatcagcaat
aaaccagccagccggaagggccgagcgcagaagtggtcctgcaactttatccgcctccatccagtctattaattgttgccgggaagctagagtaagtagttcgcca
gttaatagtttgcgcaacgttgttgccattgctacaggcatcgtggtgtcacgctcgtcgtttggtatggcttcattcagctccggttcccaacgatcaaggcgagttaca
tgatccccatgttgtgcaaaaaagcggttagctccttcggtcctccgatcgttgtcagaagtaagttggccgcagtgttatcactcatggttatggcagcactgcataa
ttctcttactgtcatgccatccgtaagatgcttttctgtgactggtgagtactcaaccaagtcattctgagaatagtgtatgcggcgaccgagttgctcttgcccggcgtc
aatacgggataataccgcgccacatagcagaactttaaaagtgctcatcattggaaaacgttcttcggggcgaaaactctcaaggatcttaccgctgttgagatccag
ttcgatgtaacccactcgtgcacccaactgatcttcagcatcttttactttcaccagcgtttctgggtgagcaaaaacaggaaggcaaaatgccgcaaaaaagggaat
aagggcgacacggaaatgttgaatactcatactcttcctttttcaatattattgaagcatttatcagggttattgtctcatgagcggatacatatttgaatgtatttagaaaaa
taaacaataggggttccgcgcacatttccccgaaaagtgc

FIGURE 6

```
   1 ATGAAAAGA TTAGCAGAAA AGAATATGTT TCTATGTATG GCCCTACTAC AGGCGATAAA GTGAGATTGG GCGATACAGA CTTGATCGCT GAAGTAGAAC
     TACTTTTCT AATCGTCTTT TCTTATACAA AGATACATAC CGGGATGATG TCCGCTATTT CACTCTAACC CGCTATGTCT GAACTAGCGA CTTCATCTTG
 101 ATGACTACAC CATTTATGGC GAAGAGCTTA AATTCGGTGG CGTAAAACC CTGAGAGAAG GCATGAGCCA ATCCAACAAC CCTAGCAAAG AAGAATTGA
     TACTGATGTG GTAAATACCG CTTCTCGAAT TTAAGCCACC GCCATTTTGG GACTCTCTC CGTACTCGGT TAGGTTGTTG GGATCGTTTC TTCTTAACCT
 201 TCTAATCATC ACTAACGCTT TAATCGTGA TTACACCGGT ATTATAAAG CGGATATTGG TATTAAAGAT GGCAAAATCG CTGGCATTGG TAAAGGCGGT
     AGATTAGTAG TGATTGCGAA ATTAGCACCT AATGTGGCCA AATCTTAGCG CGTTATAACC ATAATTTCTA CCGTTTTAGC GACCGTAACC ATTTCCGCCA
 301 AACAAAGACA TGCAAGATGG CGTTAAAAAC AATCTTAGCC TAGGTCCTGC TACTGAAGCC ATGACTTCGG TTAGCCGGTG AAGGTTTGAT CGTAACTGCT GGTGGTATTG
     TTGTTTCTGT AGTTCTACC GCAATTTTTG TTAGAATCGC ATCCAGGACG ATGACTTCGG AATCGGCCAC TTCCAAACTA GCATTGACGA CCACATAAC
 401 ACACACACAT CCACTTCATT TCACCCCAAC AAATCCCTAC AGCTTTTGCA AGCGGTGTAA CAACCATGAT TGGTGGCGGA ACTGGTCCTG CTGATGGCAC
     TGTGTGTGTA GGTGAAGTAA AGTGGGGTTG TTTAGGGATG TCGAAAACGT TCGCCACATT GTTGGTACTA ACCACCGCCT TGACCAGGAC GACTACCGTG
 501 TAATGCGACT ACTATCACTC CAGGCAGAAG GTCCGTCTTC AAATTTAAAA TGGATGCTCA GAGCGGCTGA AGAATATTCT ATGAACTTAG GTTTCTTGGC TAAAGGTAAC
     ATTACGCTGA TGATAGTGAG GTCCAGTCTTC TTTAAATTTT ACCTACGAGT CTCGCCGACT CTTAAAATC TCTTATAAGA TACTTGAATC CAAAGAACCG ATTTCCATTG
 601 GCTTCTAACG ACGCGAGCTT AGCCGATCAA ATTGAAGCTG GTGCGATTGG CTTTAAAATC CACGAAGACT GGGCACCCAC TCCTTCTGCA ATCAATCATG
     CGAAGATTGC TGCGCTCGAA TCGGCTAGTT TAACTTCGAC CACGCTAACC GAAATTTTAG GTGCTTCTGA CCCCGTGGTG AGGAAGACGT TAGTTAGTAC
 701 CGTTAGATGT TGCAGACAAA TACGATCTGT ATGCTACACG TTCAGCGAGA GGTGTGTCTG TGAAACTTAC CTGATATTAT TAAAGTAGCT GCACCTTCTG CTATTGCCGG
     GCAATCTACA ACGTCTGTTT ATGCTGATCA ACACTGAAGG TGCTGGCGGC ACGACCGCCG CCTGTGCGAG GACTATAATA AATTCATCGA GCACCTTCTG GATAACGGCC
 801 ACGCACTATG CACACTTTCC ACACTGAAGG TGTGACTTCC TGTGAATACA GAAGCAGAAC ACATGGACAT GCTTATGTG CGAATACCAC ACGGTGTGA ACCTATTTTC GTAATTTCTT GTAACAGATGATT CGTAATTTCT CTACAAGTCA
     TGCGTGATAC TGTGAAAAGG ACACTTATGT CTTCGTCTTG TGTACCTGTA CGAATACCAC ACGGTGTGA ACCTATTTTC GTAATTTCT CTACAAGTCA
 901 AACCCCACTA TCCCTTTCAC AGGGAAAGTG ACACTTATGT CTTCGTCTTG TGTACCTGTA CGAATACCAC ACGGTGTGA ACCTATTTTC GTAATTTCTT CTACAAGTCA
     TTGGGGTGAT AGGGAAAGTG ACACTTATGT CTTCGTCTTG TGTACCTGTA CGAATACCAC ACGGTGTGA ACCTATTTTC GTAATTTCT CTACAAGTCA
1001 TCGCTGATTC AAGGATCCGC CCTCAAACCA TTGCGGCTGA AACGCCGACT TCTGTGAAAC GTACTGTACC CCTAAAGAG TTAGTGGTG AGACTGAGAG TTCGATACCC
     AGCGACTAAG TTCCTAGGCG GGAGTTTGGT CTAGAACTTG GCAAACAGCT GACAAAACA AAAAGATT TGGCCGCTTG AAAGAAGAAA AAGGCGATAA CGACAACTTC
1101 TCGTGTGGGT GAAGTTATCA CTAGAACTTG GCAAACAGCT GACAAAACA AAAAGATT TGGCCGCTTG AAAGAAGAAA AAGGCGATAA CGACAACTTC
     AGCACACCCA CTTCAATAGT GATCTTGAAC CGTTTGTGA CTGTTTTGT TTTTCTTAA ACCGGCGAAC GGTATCTAG GAGTATCGAG TTCCGCTATT GCTGTTGAAG
1201 AGATACAAAC GCTACTTGTC TAAATACACC ATTACCCAG CGATCGCTCA TGGGATTAGC GAGTATCGAG GGTTCTAGA AGTCTCATC AGTGGGCAAA GTGGCTGACT
     TCCTAGTTTG CGATGAACAG ATTTATGTGG TAAATTGGGT GCTAGCGAGT CATGATCATC AAGGCGGGT TCATTGCCTT GAGTCAAATG CTGACGCGA ACGCTTCTAT
1301 TGGTATTGTG GAGTCCCGCA TTCTTTGGCC TAAAACCCAA CATGATCATC AAGGCGGGT TCATTGCCTT GAGTCAAATG CTGACGCGA ACGCTTCTAT
     ACCATAACAC CTCAGGCGT AAGAAACCGC ATTTTGGGTT GTACTAGTAG TTTCCGCCA AGCCAAATA CGATGCAAAC ATCACTTTG TGTCTCAAGC TGCCAAGATA
1401 CCCTACCCCA CAACCAGTTT ATTACAGAGA AATGTTCGCT CATCATGGTA CATCATGGTA AAGCCAAATA CGATGCAAAC ATCACTTTG TGTCTCAAGC GGCTTATGAC
     GGGATGGGGT GTTGGTCAAA TAATGTCTCT TTACAAGCGA AGACAAGTGT TGCCGGTAAA AAATTGCAGA AACATCACTA AAAAAGACAT GCAATTCAC GACACTACCG
1501 AAAGGCATTA AAGAAGAATT AGGGCTTGAA TCCCGAACTT TCTGTTCACA ACGGCCATTT TTTAACGTCT TTGTAGTGAT TTTTTCTGTA CGTTAAGTTG CTGTGATGGC
     TTTCCGTAAT TTCTTCTTAA AGTCAATCCT GAAACTTACC ATGTGTTCGT GGATGGCAAA GAAGTAACTT CTAAACCAGC CAATAAAGTG AGCTTGGCGC AACTCTTTAG
1601 CTCACATTGA AGTCAATCCT GAAACTTACC ATGTGTTCGT GGATGGCAAA GAAGTAACTT CTAAACCAGC CAATAAAGTG AGCTTGGCGC AACTCTTTAG
     GAGTGTAACT TCAGTTAGGA CTTTGAATGG TACACAAGCA CCTACCGTTT CTTCATTGAA GATTTGGTCG GTTATTTCAC TGAACCGCG TTGAGAAATC
1701 CATTTTCTAG GATTTTTCTAG GAGCAACGCT CCTTAAATCC TTAGTTTTTA GCTCTCTGAT TTTTTGTTA TCAAAAAATT GGGGGCTTTT TTTGT-AAGGA
```

FIGURE 8

```
      GTAAAGATC CTAAAAAATC CTCGTTGCGA GGAATTTAGG AATCAAAAAT CGAGAGACTA AAAAACAAAT AGTTTTTAA CCCCCGAAAA AAACA-TTCCT
1801  TACAAAATGG CAAAGAAAT CAAATTTCA GTTTAAAAGT GATAGCGCGA GAAACCTTTT ATTTGAAGGC GTGAGACAAC TCCATGACGC TGTTAAAGTA ACCATGGGGC
      ATGTTTACC GTTTCTTTA GAACGTGTTG ATCCAAAAAA GCTTATGCGC TCCAAGCATC ACTAAAGATG CACTCTGTTG AGGTACTGCG ACAATTTCAT TGGTACCCCG
1901  CAAGAGGCAG GAACGTGTTG ATCCAAAAAA GCTATGCGC TCCAAGCATC ACTAAAGATG GCGTGAGCGT CGCACTCGCA CCGATTTCTC TAACTTAATT GTTGCCGGT
      GTTCTCCGTC CTTGCACAAC TAGGTTTTT CGATACCGCG AGTTCGTAG TGATTTCTAC CGCACTCGCA CCGATTTCTC TAACTTAATT CAACGGGCA
2001  AGCTAACATG GGCGCTCAAC TCGTTAAAGA AGTACGGAGC AAAACCGCTG ATGCTGCCGG ATGCTGCCGG ACCACAGGCA CCGTGCTGGC TTATAGCATT
      TCGATGTAC CCGCGAGTTG AGCAATTTCT TCATCGCTCG TTTGGCGAC TACGACGGCC GCTACCGTGC TGGTGTCGCT GGCACGACCG AATATCGTAA
2101  TTTAAAGAAG GTTTGAGGAA CATCACGGCT GGGGCTAACC CTATTGAAGT GAAACGAGGC ATGGATAAAG CCGCTGAAGC CATTATTAAT GAGCTAAAA
      AAATTTCTTC CAAACTCCTT GTAGTGCCGA CCCCGATTGG GATAACTTCA CTTTGCTCCG TACCTATTTC GGCGACTTCG GTAATAATTA CTCGAATTT
2201  AAGCGAGCAA AAAAGTGGGC GGTAAAGAAG AAATCACCCA AGTGGCGACC ATTTCTGCAA ACTCCGATCA CAATATCGGG AAACTCATCG CTGACGCTAT
      TTCGCTCGTT TTTTACCCCG CCATTTCTTC TTTAGTGGGT TCACCGCTGG TAAAGACGTT TGAGGCTAGT GTTATAGCCC TTTGAGTAGC GACTCGATA
2301  GGAAAAAGTG GTAAAGACG GCGTGATCAC CGTTGAAGAA GCTAAGGGCA TTGAAGATGA ACTAGATGTT GTAGAAGGCA TGCAATTTGA TAGAGGCTAC
      CCTTTTCAC CCATTTCTGC CGCACTAGTG GCAACTTCTT CGATTCCCGT AACTTCTACT TGATCTACAA CATCTTCCGT ACGTAAACT ATCTCCGATG
2401  CTCTCCCCTT ATTTTGTAAC AAACGCTGAG AAAATGACCG CTCAATTGGA TAACGCTTAC ATTGCGAATG ATCCTTTTAA CGGATAAAAA AATCTCTAGC ATGAAAGACA
      GAGAGGGGAA TAAAACATTG TTTTGCGACTC TCATGCGCTT AGGGCAAACC GCTTTTAATC ATCGCTGAAG ACATTGAGGG GCAAGCTTTA ACGACTCTAG TGGTGAATAA
2501  TTCTCCCGCT ACTAGAAAAA ACCATGAAAG AGGGCAAACC TCCCGTTTGG CGAAAATTGA TAGCGACTTC TGTAACTCCC GCTTCGAAAT TGCTGAGATC ACCACTTATT
      AAGAGGGCGA TGATCTTTTT TGGTACTTTC TAAAGCTCCA ATTTCGAGGT CCGAAACCCC TGTCTTCTTT AAAGACATCG TTTCTGTAGC GATAAAATTG CGGCGTCAA
2601  ATTAAGAGGC GTGTTGAATA TCGCAGCGGT AGCGTCGCCA ATTTCGAGGT CCGAAACCCC TGTCTTCTTT AAAGACATCG TTTCTGTAGC GATAAAATTG CGGCCACTG
      TAATTCTCCG CACACACATT AAGAATTGGG CTTGAGTCTA GAAAACGCTG CTTTTGCGAC AAGACAGAGT TTCTGTCTCA GCGCGTTTAG TTTTGGGTT AACGTTCGTG CTGTTCGCTA ATACGTTTC TTTTAACGT
2701  GTTATTAGCG AAGAATTGGG CTTGAGTCTA GAAAACGCTG CTTTTGCGAC AAGACAGAGT TTCTGTCTCA GCGCGTTTAG TTTTGGGTT AACGTTCGTG CTGTTCGCTA ATACGTTTC TTTTAACGT
      CAATAATCGC TTCTTAACCC GAACTCAGAT AAGCTAGC CATGATGTCA AGACAGAGT TTCTGTCTCA GCGCGTTTAG TTTTGGGTT AACGTTCGTG CTGTTCGCTA ATACGTTTC TTTTAACGT
2801  TAGAATGCAA AGGCCATAGC CATGATGTCA GTACTACAGT TTCTGTCTCA GGCTGTGAT AAGTGGGCG CTGCAGTGA AGTGGAAATG TCACCTTAC TTTCTCTTT TTCTGGCCCA ACTACTACGC
      ATCTACCGTT TCCGGTATCG GTACTACAGT TTCTGTCTCA GGCTGTGAT AAGTGGGCG CTGCAGTGA AGTGGAAATG TCACCTTAC TTTCTCTTT TTCTGGCCCA ACTACTACGC
2901  AGAAAGGTTG GCTAAACTCT CTGGCCGGTG GACCGCCACA CCGACACTAA TTTCACCCGC GACGCTCACT ATTCGCGCGG CTCAAAAAGT GCATTTGAAT TTGCACGATG
      TCTTTCCAAC CGATTTGAGA GACCGCCACA CCGACACTAA TTTCACCCGC GACGCTCACT ATTCGCGCGG CTCAAAAAGT GCATTTGAAT TTGCACGATG
3001  TTGAGGCCGA CTAAAGCGGC TGTTGAAGAA GGTATTGTGA TTGGCGGCGG TGCGCTCTC ATTCGCGCGG CTCAAAAAGT GCATTTGAAT TTGCACGATG
      AACTCGCGCT GATTTGCGCG ACAACTCTTT CCATAACACT GGCGCCATTA AGCCCCATTA GCTCAAATCG CTATCAATGC CGGTTATGAT GGCGGGTGTGG TCGTGAATGA
3101  ATGAAAAAGT GGGCTATGAA ATCATCATGC GGCGCCATTA AGCCCCATTA GCTCAAATCG CTATCAATGC CGGTTATGAT GGCGGGTGTGG TCGTGAATGA
      TACTTTTCA CCCGATACTT TAGTAGTACG GGCGCCATTA AGCCCCATTA GCTCAAATCG CTATCAATGC CGGTTATGAT GGCGGGTGTGG TCGTGAATGA
3201  AGTAGAAAAA CACGAGGGGC ATTTTGGTTT TAACGCTAGC AATGGCAAGT ATGTGCAAGT TTAAAGAA GGCATTATTG ACCCCTTAAA AGTAGAAAGG
      TCATCTTTT GTGCTTCCCG TAAAACCAAA ATTGCCATCG GCCTGCTT TAACCACAGA AGCCACCGTG CATGAAATCA AAGAAGAAAA AGCGGCCCCA GCAATGCCTG
3301  ATCGCTTTAC AAAATGCGGT TTCGGTTTCA AGCCAAAGT TGGGACGAAA ATTGTGTCT TCGGTGGCAC GTACTTTAGT TTCTTCTTT CTCTCAACAT ATTGATTCTG CGTTACGAC
      TAGCGAAATG TTTTACGCCA CATGGGCGGT ATGGGAGGCA TGGGTGGCAT GATGGGCCCT AGCCTTGTGTG CTACCCGGGA TCGAACACC TTCGACGGACC GAGAGTTGTA AAAGAAAGC
3401  ATATGGGTGG CATGGGCGGT ATGGGAGGCA TGGGTGGCAT GATGGGCCCT AGCCTTGTGTG CTACCCGGGA TCGAACACC TTCGACGGACC GAGAGTTGTA AAAGAAAGC
      TATACCCACC GTACCCGCCA ACCCCTCCGT ACCCACCGTA CTACCCGGGA TCGAACACC TTCGACGGACC GAGAGTTGTA TAACTAAGAC TTTTCTTTCG
```

FIGURE 8 Cont.

```
3501 TTAAGCCCCC TTGCTTTTAT TTTTTGTCAA TTTACTATTT TCTTTTATGA TTAGCTCAAG CAACAAAAGT TATTCGTAAG GTGCGTTTGT TGTAAAAATT
     AATTCGGGGG AACGAAAATA AAAAACAGTT AAATGATAAA AGAAAATACT AATCGAGTTC GTTGTTTTCA ATAAGCATTC CACGCAAACA ACATTTTTAA
3601 TTTGTTTGGA AGGAAAAGGC AATGCTAGGA CTTGTATTGT TATATGTTGG GATTGTTTTA ATCAGCAATG GGATTTGCCG GTTAACCAAA GTCGATCCTA
     AACAAACCT TCCTTTTCCG TTACGATCCT GAACATAACA ATATACAACC CTAACAAAAT TAGTCGTTAC CCTAAACGCC CAATTGGTTT CAGCTAGGAT
3701 AAAGCACTGC GGTGATGAAC TTTTTTGTGG GCGGACTTTC CATTATTTGT AATATAGTTG TCATCACTTA TTCTGCACTC CACCCTACAG CCCCTGTAGA
     TTTCGTGACG CCACTACTTG AAAAAACACC CGCCTGAAAG GTAATAAACA TTATATCAAC AGTAGTGAAT AAGACGTGAG GTGGGATGTC GGGGACATCT
3801 AGGTGCTGAA GATATTGCTC AAGTATCGCA CCATTTGACT AGTTTCTATG GACCAGCGAC TGGGTTATTG TTTGGTTTCA CCTACTTGTA TGCCGCTATC
     TCCACGACTT CTATAACGAG TTCATAGCGT GGTAAACTGA TCAAAGATAC CTGGTCGCTG ACCCAATAAC AAACCAAAGT GGATGAACAT ACGCCGATAG
3901 AACCACACTT TTGGTTTGGA TTGGAGGCCC TACTCTTGGT ATAGCTTATT CGTAGCGATC AACACGATTC CTGCTGCGAT TTTATCCCAC TATAGCGATA
     TTGGTGTGAA AACCAAACCT AACCTCCGGG ATGAGAACCA GCATCGCTAG TTGTGCTAAG GACGACGCTA AAATAGGGTG ATATGCTAT
4001 TGCTTGATGA CCACAAAGTG TTAGGCATCA CTGAAGGCGA TTGGTGGGCG ATCATTTGGT TGGCTTGGGG TGTTTTGTGG CTTACCGCTT TCATTGAAAA
     ACGAACTACT GGTGTTTCAC AATCCGTAGT GACTTCCGCT AACCACCCGC TAGTAAACCA ACGAAACCC ACAAAACACC GAATGGCGAA AGTAACTTTT
4101 CATCTTGAAA ATCCCTTTAG GGAAATTCAC TCCATGGCTT GCTATCATTG AGGGTATTTT AACCGCTTGG ATCCCTGCTT GGTTGCTCTT TATCCAACAC
     GTAGAACTTT TAGGGAAATC CCTTTAAGTG AGTACCGAA CGATAGTAAC TCCCATAAAA TTGGCGAACC TAGGGACGAA CCAACGAGAA ATAGGTTGTG
4201 TGGGTGTGAG ATGATCATAG AGCGTTTAGT TGGCAATCTA AGGGATTTAA ACCCCTTGGA TTTCAGCGTG GATCATGTGG ATTTGGAATG GTTTGAAACG
     ACCCACACTC TACTAGTATC TCGCAAATCA ACCGTTAGAT TCCCTAAATT TGGGAACCT ACGCGTTAAA GACGCCAAAT CCTCAAGGG GATATTTTAT
4301 AGGAAAAAA TCGCTCGTTT TAAAACCAGG CAAGCAAAG ACATAGCCAT ACGCGTTAAA GACGCCAAAT CCTCAAGGG GATATTTTAT
     TCCTTTTTT AGCGAGCAAA ATTTTGGTCC GTTCCGTTTC TGTATCGGTA TTCTGAAGTC TAGATGTGGT TCAACCCCGA GAGAGTTCCC CTATAAATA
4401 TTAAAGAAGA GAAGGAAATT ATCGCCGTTA ATATCTTGAA TATAGAACCT AAGACTTCAG TAAGTGTAGG TTCGGTTCTC GCACCGTCTT CATCGCTTTT ATACGATACT
     AATTTCTTCT CTTCCTTTAA TAGCGGCAAT CTTTATACTA TGGCGAGTCT CAATTTGAAT TTAAACACC ATTTGAAAAG CCCACGCTAG CGTTATTAGA AAAGCTAGGG
4501 AATAGGAAAC CGCCATGCGG GCCGTACGCC GAAATATGAT ACCGCTCAGA GTTAAACTTA AATTTTGTGG TAAACTTTTC GGGTGCGATC GCAATAATCT TTTCGATCCC
     TTATCCTTTG GCGGTACGCC GAAATATGAT ACCGCTCAGA GTTAAACTTA AATTTTGTGG TAAACTTTTC GGGTGCGATC GCAATAATCT TTTCGATCCC
4601 GTTCAAAATC GTGTTTAAG TTCAAAATTG GATTCCAAAG AACGCTTAAC CGTGAGCATG CCCATAGTG AGCCTAATTT TAAGGTCTCA CTAGCGAGCG
     CAAGTTTTAG CACAAATTC AAGTTTTAAC CTAAGGTTTC TTGCGAATTG GCACTCGTAC GGGGTATCAC TCGGATTAAA ATTCCAGAGT GATCGCTCGC
4701 ATTTTAAAGT GGTCGTAAAA TAG - SEQ ID NO:3
     TAAAATTTCA CCAGCATTTT ATC - SEQ ID NO:4
```

FIGURE 8 Cont.

HcpA-3M2-HA$_{tag}$

| 1 | 2 | 3 | 5 |

SYNTHETIC OPERON

CROSS-REFERENCE TO RELATED APPLICATIONS

This application is the U.S. national stage application under 35 U.S.C. §371 of International Application Number PCT/AU2010/000806, filed on Jun. 25, 2010, which claims the benefit of priority to Australian Application No. 2009902990, filed on Jun. 26, 2009. The contents of each of these applications are hereby incorporated by reference in their entireties.

FIELD

The present invention relates to synthetic operons. In particular, the present invention relates to the construction and use of synthetic operons in bacterial delivery systems, methods, constructs and cells for use therein.

BACKGROUND

Live bacteria, such as probiotic bacteria or live attenuated pathogens, represent attractive systems for the delivery of biologically active agents as they generally allow oral administration and the sustained release of the agent over a protracted period of time, eliminating the need for repeat doses.

As the therapeutic potential of bacterial delivery systems has been recognised a need to develop expression cassettes for the delivery of the active agents has also developed. These expression cassettes have mainly focused on the use of replicative plasmids; however, as these plasmids are essentially unstable ie often being lost by the bacterium over time, research to date has concentrated on plasmid stabilization. Most of the research in this area has been based on auxotrophy or gene essentiality using the expression in trans of the corresponding missing gene. For example, plasmid expression vectors have been developed harbouring the gene encoding aspartate β-semialdehyde dehydrogenase, an enzyme essential for the viability of bacteria (Galan et al., (1990), *Gene*, 94:29-35). These vectors were used in *Salmonella* vaccine strains harbouring lesions in the host asd gene encoding the enzyme. Thus, loss of the plasmid resulted in cell death and prevented selection of bacteria without the plasmid.

Accordingly, there remains a need for a delivery system that provides the stable, constitutive expression of vaccine antigens or biologically active molecules at sufficient levels to enable their use in clinical practice.

SUMMARY

The inventors of the present invention have developed a bacterial delivery system based on the construction of synthetic operon that results in the co-transcription of a gene of interest with a gene essential to the bacterium.

Accordingly, in a first aspect, the present invention provides a synthetic operon for integration into a bacterial chromosome of a bacterium comprising a promoter operably-linked to at least two genes, wherein at least one gene is a gene of interest and at least one gene is a gene essential to said bacterium, and wherein the promoter is arranged such that the gene of interest and the essential gene are co-transcribed.

In some embodiments, the integration of the synthetic operon into the bacterial chromosome is stable integration.

Suitable bacteria for use in the present invention include those that are capable of establishing an infection within a eukaryotic host. In some embodiments, the bacterium is invasive, e.g., it attaches to a cell of the eukaryotic host and enters the cytoplasm of the cell or resides in close communication with the outside of the host cell.

Preferably the bacterium is one capable of forming a chronic infection in an animal. Accordingly, suitable bacteria include, but are not limited to, *Aeromonas* spp., *Bacillus* spp., *Bacteroides* spp., *Bartonella* spp., *Bifidobacteria* spp., *Bordetella* spp., *Brucella* spp., *Campylobacter* spp., *Chlamydia* spp., *Citrobacter* spp., *Clostridium* spp., *Corynebacterium* spp., *Erysipelothrix* spp., *Escherichia* spp., *Francisella* spp., *Fusobacteria* spp., *Helicobacter* spp., *Hemophilus* spp., *Klebsiella* spp., *Legionella* spp., *Listeria* spp., *Mycobacterium* spp., *Neisseria* spp., *Pasteurella* spp., *Pneumococcus* spp., *Pseudomonas* spp., *Rhodococcus* spp., *Rickettsia* spp., *Salmonella* spp., *Shigella* spp., *Staphylococcus* spp., *Streptococcus* spp., *Vibrio* spp. and *Yersinia* spp. Any of these strains can be attenuated, if needed, using known methods.

In some embodiments, the bacterium is *Helicobacter pylori*. *H. pylori* is particularly useful in the present invention as it is able to colonize and form a chronic infection within the human gastric mucosa. This characteristic renders *H. pylori* a suitable candidate for the delivery of agents though the mucosa. In some embodiments, the *H. pylori* strain is one of the strains deposited under terms in accordance with the Budapest Treaty with the National Measurement Institute (NMI), 1/153 Bertie Street, Port Melbourne, Victoria, Australia on Apr. 22, 2009 (OND737, OND738, OND739 and OND740) and May 28, 2010 (OND248 and OND256). These strains of *H. pylori* have been assigned the following accession numbers: V09/009,101 (OND737); V09/009,102 (OND738); V09/009,103 (OND739); V09/009,104 (OND740); V10/014,059 (OND248) and V10/014,060 (OND256).

The gene essential to the bacterium may be a gene that is essential in vitro or in vivo. For example, the gene essential to the bacterium may be essential to a function selected from the group consisting of survival, colonisation, proliferation and growth.

An essential gene may be used in the de novo construction of a synthetic operon according to the present invention. Alternatively, the synthetic operon may be constructed by inserting the gene of interest into a naturally-occurring operon that encodes a gene essential to the bacterium in situ. In some embodiments, the synthetic operon is constructed from the urease operon of *H. pylori*. The urease operon of *H. pylori* is essential for colonisation of the stomach and allows the bacteria to survive in the acidic gastric environment.

In some embodiments, the gene of interest is encoded by an isolated nucleic acid molecule. It will be appreciated by those skilled in the art that the isolated nucleic acid molecule of the present invention may be a cDNA, a genomic DNA or a hybrid molecule thereof. Preferably, the isolated nucleic acid is a cDNA.

The isolated nucleic acid encoding the gene of interest may be homologous or heterologous to the genus or species of bacterium used for delivery.

In some embodiments, the isolated nucleic acid encodes a biologically active agent such as an antigen, an organic molecule, or a pharmacologically-active agent like a therapeutic agent or prophylactic agent.

In a second aspect, the present invention provides a method for producing a synthetic operon to effect expression of a gene of interest in a bacterium comprising the steps of: (i) identifying an operon in the chromosomal DNA of a bacterium that encodes at least one gene essential to said bacterium and (ii) inserting a gene of interest into said operon to produce a synthetic operon, wherein the gene of interest is co-transcribed with the at least one essential gene.

In a third aspect, the present invention provides a method for expressing a gene of interest in a bacterium comprising the steps of: (i) constructing a synthetic operon comprising a promoter operably-linked to at least two genes, wherein at least one gene is a gene of interest and at least one gene is a gene essential to said bacterium, and wherein the promoter is arranged such that the gene of interest and the essential gene are co-transcribed; (ii) integrating the synthetic operon into the chromosomal DNA of a bacterium; and (iii) culturing said bacterium in order to express said gene of interest.

BRIEF DESCRIPTION OF THE FIGURES

FIG. 4: The sequence of the pAB plasmid (SEQ ID NO:1).

FIG. 6: The sequence of the pBI plasmid (SEQ ID NO:2).

FIG. 8: DNA sequence of the synthetic urease operon containing the groEL gene tagged with the cholera toxin CTP3 epitope after the ureB gene (SEQ ID NO:3 & SEQ ID NO:4).

FIG. 17: Western analysis of recombinant bacteria. Western blot, lane 1, 2, 3, 5 recombinant clones expressing the fusion of 36 kDa. Wild type bacteria did not exhibit any signal (data not shown). Antibody: anti-haemagglutinin.

Figure 1:
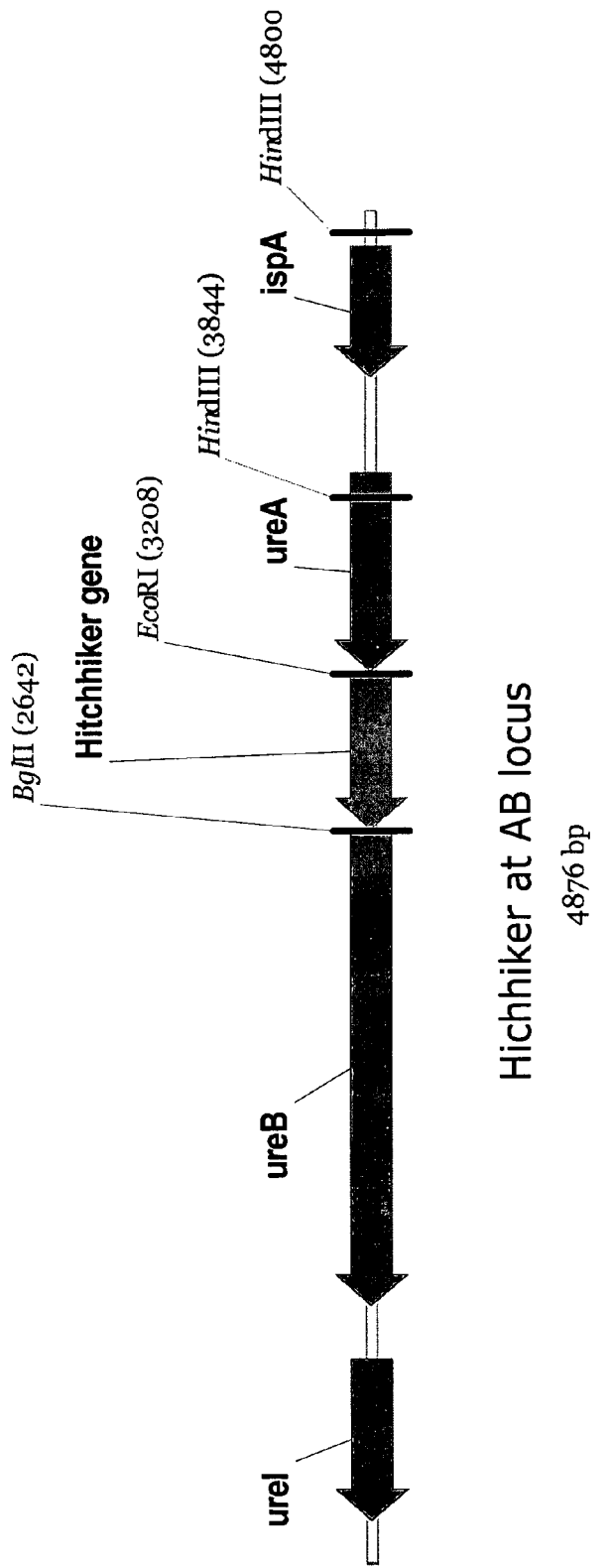
FIG. 1: Genomic map of the urease synthetic operon with the gene of interest inserted between ureA and ureB.
Figure 2:
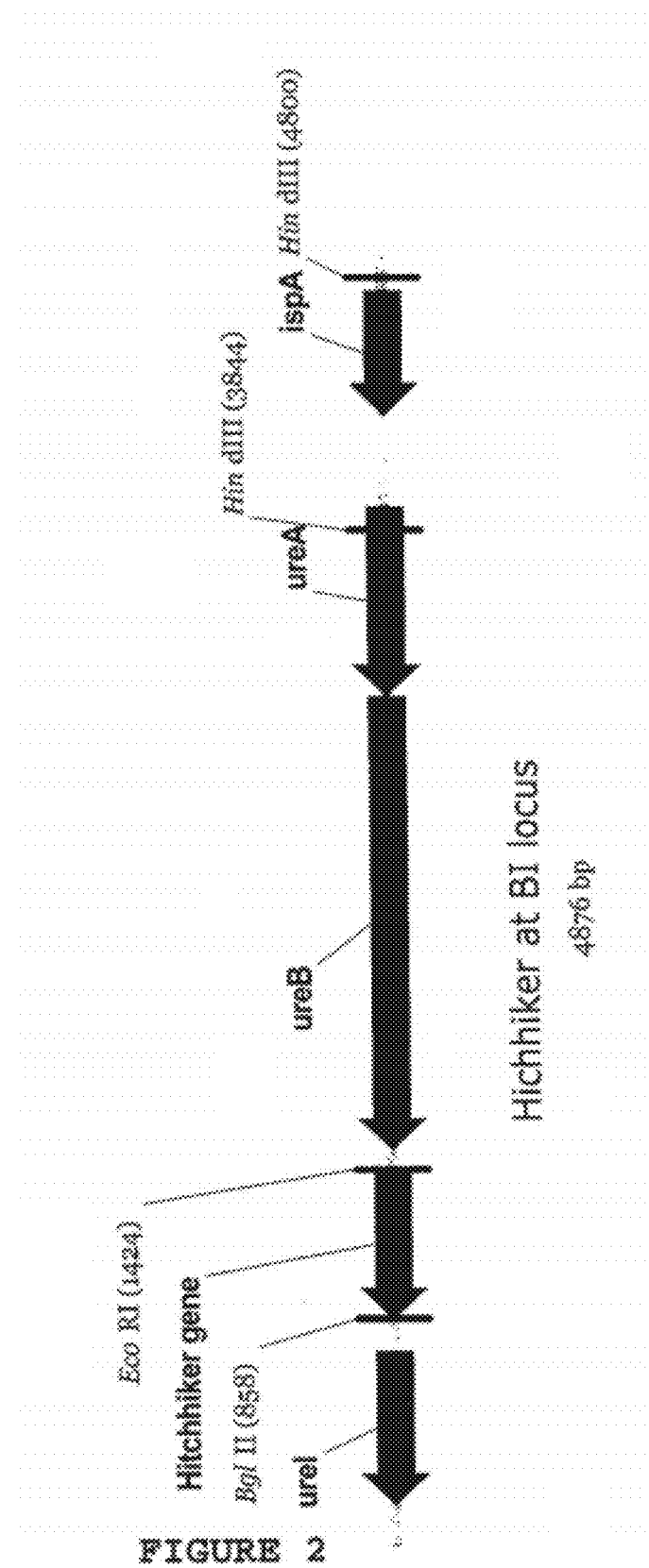
FIG. 2: Genomic map of the urease synthetic operon with the gene of interest inserted after the ureB.
Figure 3:
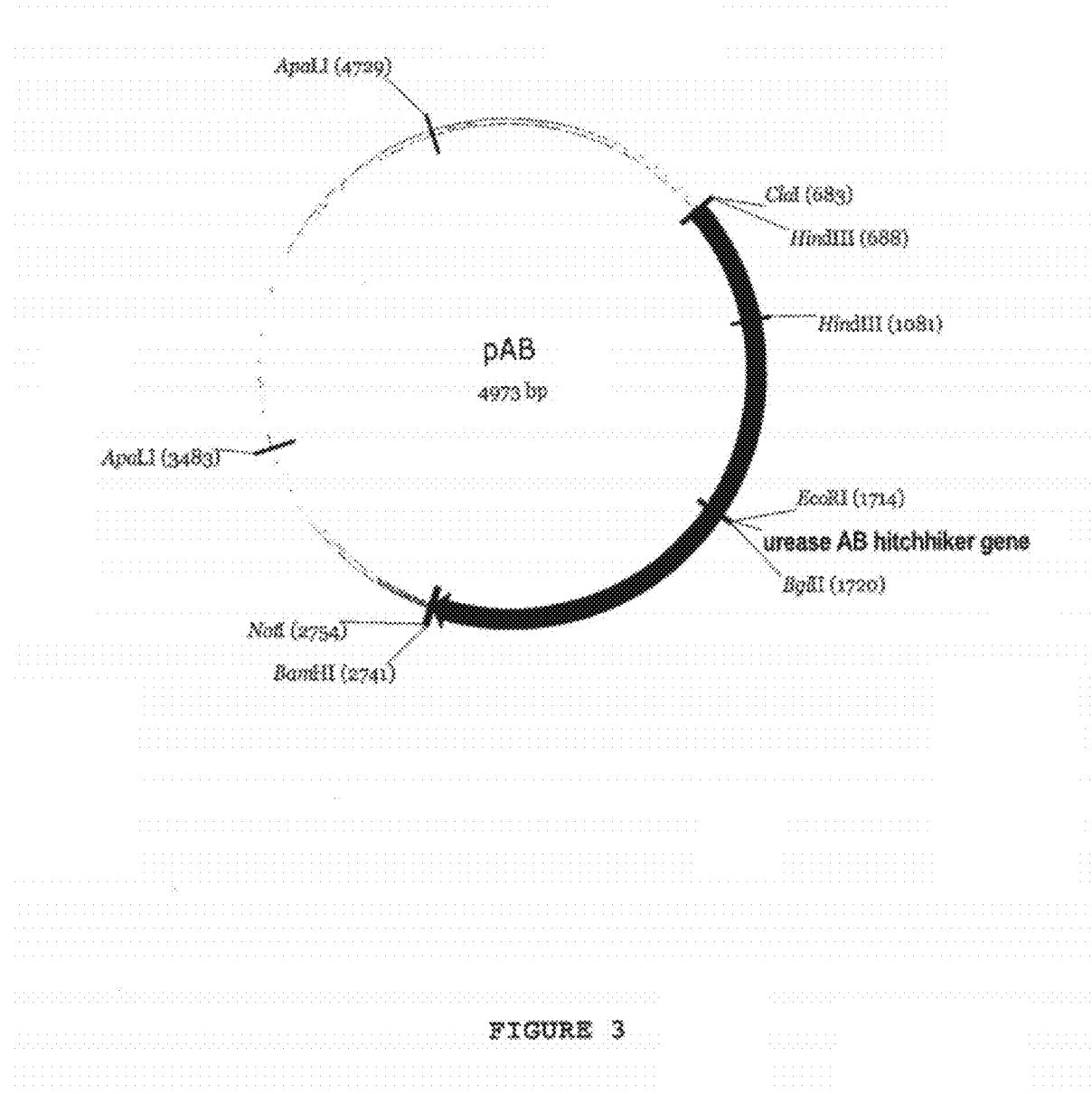
FIG. 3: Plasmid map of pAB.
Figure 5:
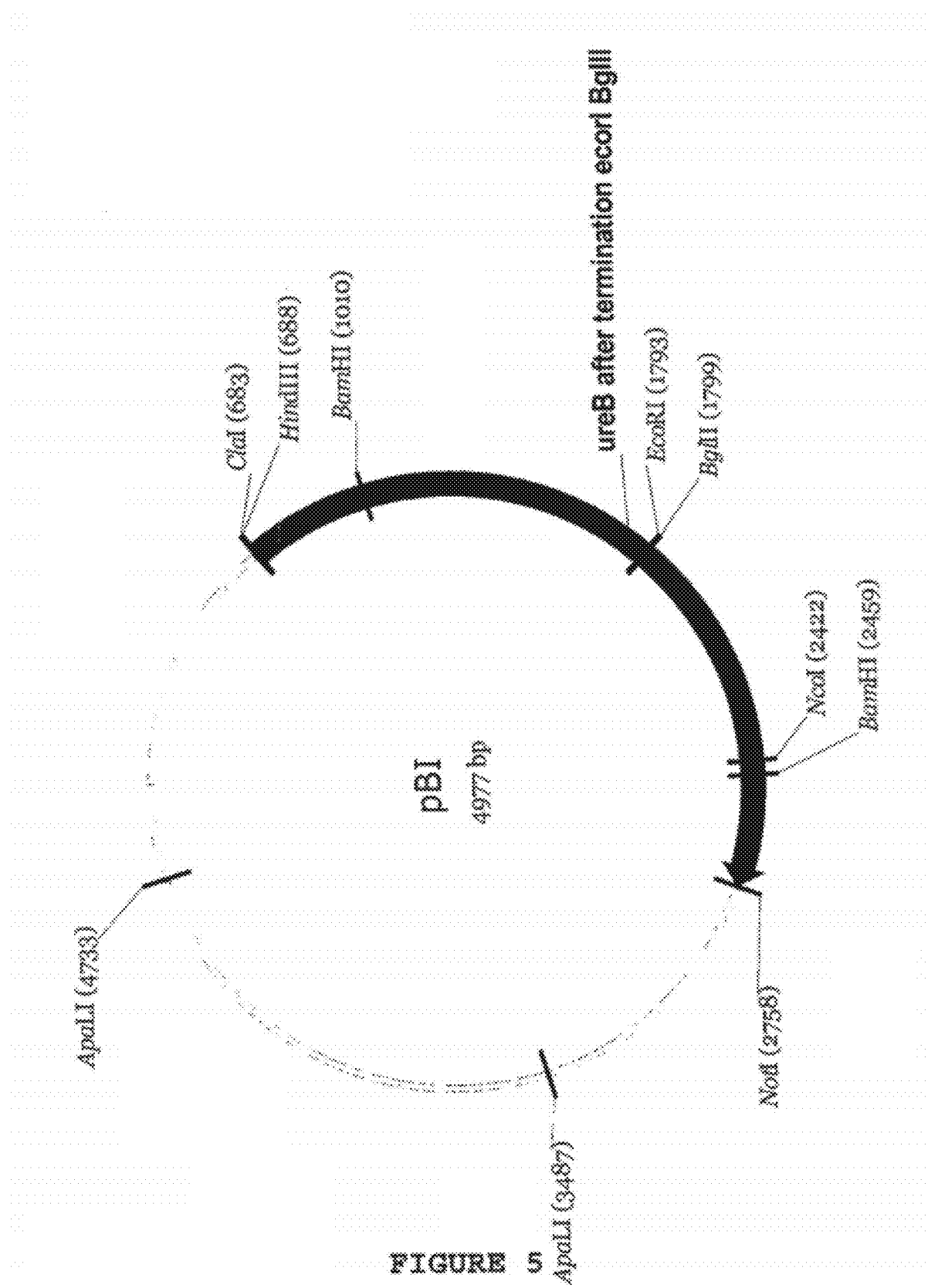
FIG. 5: Plasmid map of pBI.

DESCRIPTION OF THE PREFERRED
EMBODIMENTS OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional techniques of pharmacology, molecular biology (including recombinant techniques), cell biology, biochemistry, and immunology, which are within the skill of the art. Such techniques are well known to the skilled worker, and are explained fully in the literature. See, eg., Coligan et al. "Current protocols in Protein Science" (1999) Volume I and II (John Wiley & Sons Inc.); Sambrook et al., (Molecular Cloning: A Laboratory Manual, $2^{nd}$ & $3^{rd}$ Editions, Cold Spring Harbor Laboratory press (1989) (2001); and Bailey, J. E. and Ollis, D. F., Biochemical Engineering Fundamentals, McGraw-Hill Book Company, NY, 1986; "Oligonucleotide Synthesis" (M. J. Gait, ed., 1984); "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodicals) "Polymerase Chain Reaction" (Mullis et al., eds., 1994); and "Current Protocols in Immunology" (J. E. Coligan et al., eds., 1991).

It must be noted that as used herein and in the appended claims, the singular forms "a," "an", and "the" include plural reference unless the context clearly dictates otherwise. Thus, for example, a reference to "a nucleic acid" includes a plurality of such nucleic acids, and a reference to "an isolated peptide" is a reference to one or more peptides, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The prolonged, effective delivery of biologically active agents directly to an animal by administering a single dose of bacteria that produce the biologically active agent represents a valuable delivery system. However, in order to utilize bacteria in this way there is a requirement to have a useable expression system. Accordingly, in the broadest aspect, the present invention relates to a synthetic operon comprising a gene of interest and a gene essential to a bacterium, which operon provides stable expression of the gene of interest.

The term "bacteria," "bacterium" and "bacterial host" are used herein interchangeably and refer to the bacterium used as the delivery system described herein. Suitable bacteria for use in the present invention include those that are capable of establishing an infection within a eukaryotic host. In some embodiments, the bacterium is invasive, e.g., it attaches to a cell of the eukaryotic host and enters the cytoplasm of the host cell or resides in close communication with the outside of the host cell, preferably within the lumen of the stomach.

Thus, in some embodiments, the bacterium is one capable of forming a chronic infection in an animal. Suitable bacteria include, but are not limited to, *Aeromonas* spp., *Bacillus* spp., *Bacteroides* spp., *Bartonella* spp., *Bifidobacteria* spp., *Bordetella* spp., *Brucella* spp., *Campylobacter* spp., *Chlamydia* spp., *Citrobacter* spp., to *Clostridium* spp., *Corynebacterium* spp., *Erysipelothrix* spp., *Escherichia* spp., *Francisella* spp., *Fusobacteria* spp., *Helicobacter* spp., *Hemophilus* spp., *Klebsiella* spp., *Legionella* spp., *Listeria* spp., *Mycobacterium* spp., *Neisseria* spp., *Pasteurella* spp., *Pneumococcus* spp., *Pseudomonas* spp., *Rhodococcus* spp., *Rickettsia* spp., *Salmonella* spp., *Shigella* spp., *Staphylococcus* spp., *Streptococcus* spp., *Vibrio* spp. and *Yersinia* spp.

Any of these strains can be attenuated, if needed, using known methods. Methods for attenuating bacteria are well known in the field. For example, attenuated *Salmonella* strains (Germanier & Furer, (1975), *J. Infect. Dis.*, 141, 553-558; Hone et al., (1991), *Vaccine*, 9, 810-816; Tacket et al., (1992), Vaccine, 10, 443-446; Tacket et al., (1992), *Infect. Immun.* 60, 536-541); *Vibrio cholerae* (Mekalanos et al., (1983), *Nature*, 306, 551-557), *Shigella* species such as *S. flexneri* (Sizemore et al., (1995), *Science*, 270, 299-302; Mounier et al., (1992), *EMBO J.*, 11 1991-1999); *Listeria* such as *L. monocytogenes* (Milon & Cossart, (1995), *Trends in Microbiology*, 3, 451-453); *Streptococcus*, such as *S. gordonii* (Medaglini et al., (1995), *Proc. Natl. Acad. Sci. USA*, 92, 6868-6872); *Mycobacterium*, such as *Bacille Calmette Guerin* (Flynn, (1994), *Cell. Mol. Biol.*, 40 Suppl. 1 31-36); *Helicobacter* (US Pat. Applic. No. 20020161192 to Meyer et al.); Pasteurellaceae family including Pasteurella multocida, Mannheimia haemolytica, Actinobacillus pleuropneumoniae, Haemophilus somnus, Actinobacillus suis, and Haemophilus parasuis; (US Pat. Applic. No. 20070082009 to Lawrence et al.).

Essentially, attenuating mutations can be introduced into bacterial species using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, λ phage mediated crossover, and conjugational transfer; or site-directed mutagenesis using recombinant DNA techniques. Recombinant DNA techniques are preferable since strains constructed by recombinant DNA techniques are far more defined. Examples of such attenuating mutations include, but are not limited to:

(i) auxotrophic mutations, such as aro (Hoiseth et al. Nature, 291:238-239 (1981)), gua (McFarland et al. Microbiol. Path., 3:129-141 (1987)), nad (Park et al. J. Bact., 170:3725-3730 (1988), thy (Nnalue et al. Infect. Immun., 55:955-962 (1987)), and asd (Curtiss et al. Infect. Immun., 55:3035-3043 (1987)) mutations;

(ii) mutations that inactivate global regulatory functions, such as cya (Curtiss et al. (1987) supra), crp (Curtiss et al. (1987), supra), phoP/phoQ (Groisman et al. Proc. Natl. Acad. Sci., USA, 86:7077-7081 (1989); and Miller et al. Proc. Natl. Acad. Sci., USA, 86:5054-5058 (1989)), $phop_c$ (Miller et al. J. Bact., 172:2485-2490 (1990)) or ompR (Dorman et al. Infect. Immun., 57:2136-2140 (1989)) mutations;

(iii) mutations that modify the stress response, such as recA (Buchmeier et al. Mol. Micro., 7:933-936 (1993)), htrA (Johnson et al. Mol. Micro., 5:401-407 (1991)), htpR (Neidhardt et al. Biochem. Biophys. Res. Com., 100:894-900 (1981)), hsp (Neidhardt et al. Ann. Rev. Genet., 18:295-329 (1984)) and groEL (Buchmeier et al. Sci., 248:730-732 (1990)) mutations;

(iv) mutations in specific virulence factors, such as IsyA (Libby et al. Proc. Natl. Acad. Sci., USA, 91:489-493 (1994)), pag or prg (Miller et al. (1990), supra; and Miller et al. (1989), supra), iscA or virG (d'Hauteville et al. Mol. Micro., 6:833-841 (1992)), plcA (Mengaud et al. Mol. Microbiol., 5:367-72 (1991); Camilli et al. J. Exp. Med, 173:751-754 (1991)), and act (Brundage et al. Proc. Natl. Acad. Sci., USA, 90:11890-11894 (1993)) mutations;

(v) mutations that affect DNA topology, such as topA (Galan et al. Infect. Immun., 58:1879-1885 (1990));

(vi) mutations that disrupt or modify the cell cycle, such as min (de Boer et al. Cell, 56:641-649 (1989)).

(vii) introduction of a gene encoding a suicide system, such as sacB (Recorbet et al. App. Environ. Micro., 59:1361-1366 (1993); Quandt et al. Gene, 127:15-21 (1993)), nuc (Ahrenholtz et al. App. Environ. Micro., 60:3746-3751 (1994)), hok, gef, kil, or phlA (Molin et al. Ann. Rev. Microbiol., 47:139-166 (1993));

(viii) mutations that alter the biogenesis of lipopolysaccharide and/or lipid A, such as rFb (Raetz in Esherishia coli and *Salmonella typhimurium*, Neidhardt et al., Ed., ASM Press, Washington D.C. pp 1035-1063 (1996)), galE (Hone et al. J. Infect. Dis., 156:164-167 (1987)) and htrB (Raetz, supra), msbB (Reatz, supra) and (ix) introduction of a bacteriophage lysis system, such as lysogens encoded by P22 (Rennell et al. Virol, 143:280-289 (1985)), λ murein transglycosylase (Bienkowska-Szewczyk et al. Mol. Gen. Genet., 184:111-114 (1981)) or S-gene (Reader et al. Virol, 43:623-628 (1971)).

The attenuating mutations can be either constitutively expressed or under the control of inducible promoters, such as the temperature sensitive heat shock family of promoters (Neidhardt et al. supra), or the anaerobically induced nirB promoter (Harborne et al. Mol. Micro., 6:2805-2813 (1992)) or repressible promoters, such as uapA (Gorfinkiel et al. J. Biol. Chem., 268:23376-23381 (1993)) or gcv (Stauffer et al. J. Bact., 176:6159-6164 (1994)).

In some embodiments, the bacteria is a *Helicobacter* strain. Examples of *Helicobacter* strains which can be employed in the present invention include *H. mustelae* (ATCC No. 43772). In some embodiments, the bacterium is *Helicobacter pylori*. *H. pylori* is particularly useful in the present invention as it is able to colonize and form a chronic infection within the human gastric mucosa. The term "chronic infection" refers to an infection that is ongoing for 6 months or more. This characteristic renders *H. pylori* a suitable candidate for the delivery of agents though the mucosa. In some embodiments, the strains of *H. pylori* are those deposited under terms in accordance with the Budapest Treaty with the National Measurement Institute (NMI), 1/153 Bertie Street, Port Melbourne, Victoria, Australia on Apr. 22, 2009 (OND737, OND738, OND739 and OND740) and May 28, 2010 (OND248 and OND256). The strains of *H. pylori* have been assigned the following accession numbers: V09/009,101 (OND737); V09/009,102 (OND738); V09/009,103 (OND739); V09/009,104 (OND740); V10/014,059 (OND248) and V10/014,060 (OND256).

In some embodiments, the *H. pylori* have been manipulated so that some of the pathogenic features have been removed and/or attenuated. For example, the vacuolating cytotoxin and the cag pathogenicity island genes can be removed so that the *H. pylori* are less pathogenic. Attenuating mutations can be introduced into *Helicobacter pylori* as described supra, for example, using non-specific mutagenesis either chemically, using N-methyl-N-nitro-N-nitrosoquanidine, or using recombinant DNA technologies.

Once the bacterial host has been identified and, if required, attenuated, an appropriate synthetic operon is constructed. The term "synthetic operon", as used herein, refers to an operon that has been artificially constructed to express a gene of interest as part of an operon. The term "operon", as used herein, refers to a transcriptional unit that contains one or more structural genes (i.e. a gene that codes for any RNA or protein product), which are transcribed into one polycistronic mRNA, i.e., a single mRNA molecule that codes for more than one protein (co-transcription). Each gene coding sequence contains its own suitably positioned ribosome binding site upstream.

Thus, an important aspect of the present invention is the co-transcription of a gene essential to the bacterial host and a gene of interest. As eluded to above, the term "co-transcribed" and "co-transcription" or grammatical equivalents thereof, as used herein, describes transcription of two or more genes from a single promoter into one polycistronic mRNA. Each gene coding sequence contains its own suitably positioned ribosome binding site facilitating the translation of multiple, different, complete, functional proteins from the polycistronic mRNA. This process is distinct from "fusion genes", which result in a single polypeptide ("fusion protein") with functional properties derived from each of the original proteins, i.e. does not result in the production of multiple, different, complete, functional proteins.

Consequently, the synthetic operon of the present invention must contain at least one gene essential to the bacterial host. The terms "essential" and "non-essential" are classic molecular genetic designations that relate to the functional significance of a gene with respect to its effect on the viability of an organism. The term "essential", "essential gene" or "gene essential to", as used herein, refers to a gene that if deleted, or rendered non-functional, will result in lethality. Lethality refers to both absolute lethality, i.e. death of the bacterium under any condition and conditional lethality, i.e. death of the bacterium only under certain conditions, for example in vivo conditions. In contrast, "non-essential genes" are those that if deleted, or rendered non-functional, will still result in viable bacteria.

Essential genes typically include those required for survival, colonisation, proliferation and growth. For example, an enzyme, a chaperone, a cell envelope protein, a chromosome-associated protein, a purine, a pyrimidine, a nucleoside and a nucleotide, a transcription factor, a translation factor, a transport protein, a binding protein, an amino acid, a peptide or an amine. Further, essential genes may have roles in biosynthesis of amino acids, biosynthesis of cofactors, biosynthesis of prosthetic groups, biosynthesis of carriers, biosynthesis of surface polysaccharides, biosynthesis of liposaccharides, biosynthesis of murein sacculus, biosynthesis of peptidoglycan, cell division, protein secretion, peptide secretion, DNA metabolism, DNA replication, DNA recombination, DNA repair, pentose phosphate pathway, glycolysis, gluconeogenesis, fatty acid metabolism, lipid metabolism, sterol metabolism, protein synthesis, tRNA aminoacylation, purine ribonucleotide biosynthesis, sugar-nucleotide biosynthesis, sugar-nucleotide conversion, regulatory function, transcription, translation, and degradation of protein, degradation of peptide and degradation of glycopeptide.

Methods for identifying a gene essential to bacteria are well known to those skilled in the art. For example, inactivation of a candidate gene may be used to indicate whether the gene codes for a gene essential to the bacterium, i.e. if a gene is inactivated and no growth is observed under certain conditions, compared to a wild-type control, this indicates the gene is essential to the bacteria in those conditions. For example, to determine whether the gene is essential for in vivo survival of bacteria, an animal may be administered with the modified bacteria and, after a sufficient period of time, bacterial cell numbers can be counted and compared to the number of bacterial cell in an animal administered with a wild-type control. Again, growth of the bacteria and high bacterial load in the animal administered wild-type bacteria, compared to the modified bacteria will indicate that the gene is essential to the survival of the bacteria in vivo.

By way of example, inactivation of a gene may be accomplished by the introduction, substitution, or removal of one or more (or several) nucleotides in the gene or a regulatory element required for the transcription or translation thereof. For example, nucleotides may be inserted or removed so as to result in the introduction of a stop codon, the removal of the start codon, or a change in the open reading frame. Such modifications or inactivation may be accomplished by site-directed mutagenesis or PCR generated mutagenesis in accordance with methods known in the art.

Examples of essential genes include, but are not limited to, murA, murB, murC, murD, murE, murF, murG, murH and, murI (which are necessary for synthesis of the murein rigid cell wall layer), dapA, dapB, dapC, dapD, dapE, dapF and asd (which are necessary for synthesis of diaminopimelic acid (DAP)), air and dadB (which are necessary for synthesis of D-alanine), ddlA, and ddlB (which are necessary for synthesis of D-alanyl-D-alanine). Muramic acid, DAP and D-alanine are unique constituents of the rigid layer of the cell wall and are not incorporated into any other bacterial structure or component.

Once the gene essential to the bacteria has been identified, in some embodiments, it is isolated and used to construct a synthetic operon. The techniques used to isolate or clone a gene (polynucleotide) encoding a polypeptide are known in the art and include isolation from genomic DNA, preparation from cDNA, or a combination thereof. The cloning of a gene from the chromosomal DNA of the bacteria can be effected, e.g., by using the well known polymerase chain reaction (PCR) techniques. See, e.g., Innis et al., (1990), *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may also be applicable.

The gene essential to the bacteria is then operably linked to a gene of interest. The gene of interest employed in the present invention will generally be in the form of an isolated nucleic acid molecule. The term "isolated nucleic acid", as used herein, is a nucleic acid, the structure of which is not identical to that of any naturally occurring nucleic acid or to that of any fragment of a naturally occurring genomic nucleic acid spanning more than three separate genes. The term therefore covers, for example, (a) a DNA molecule which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Thus, in the present case, the gene of interest might be a coding region for a biologically active molecule that has been isolated. As discussed elsewhere, the coding region of the gene of interest might differ from naturally occurring genes; however, the amino acid sequence of the gene of interest will have a high degree of percent identify.

"Percent identity (homology)" of two amino acid sequences or of two nucleic acids is determined using the algorithm of Karlin and Altschul, 1990, Proc. Natl. Acad. Sci. USA, 87:2264-2268, 1990, modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, word length=12, to obtain nucleotide sequences homologous to a nucleic acid molecule of the invention. BLAST protein searches are performed with the XBLAST program, score=50, word length=3, to obtain amino acid sequences homologous to a reference polypeptide (eg., SEQ ID NO: 2). To obtain gapped alignments for comparison purposes, Gapped BLAST is utilised as described in Altschul et al. (Nucleic Acids Res. 25:3389-3402, 1997). When utilising BLAST and Gapped BLAST programs, the default parameters of the respective programs (eg. XBLAST and NBLAST) are used. These may be found on the World Wide Web at the URL "ncbi.nim.nih.gov".

Methods for isolating nucleic acids are well known to those skilled in the art and have also been discussed supra.

The isolated nucleic acid will generally code for a "heterologous" polypeptide, i.e., not expressed by the host bacterium in nature or prior to the introduction into the bacteria, or an ancestor thereof.

In some embodiments, the heterologous polypeptide is a biologically active agent. The skilled person will appreciate that the methods of the present invention could be used to deliver a range of biologically active agents. Examples of suitable biological agents include ones which are capable of functioning locally or systemically, e.g. an agent capable of exerting an endocrine activity affecting local or whole-body metabolism and/or an agent which is capable of regulating the activities of cells belonging to the immuno/haemopoeitic system and/or an agent which is capable of affecting the viability, growth and differentiation of a variety of normal or neoplastic cells in the body or affecting the immune regulation or induction of acute phase inflammatory responses to injury and infection and/or an agent which is capable of enhancing or inducing resistance to infection of cells and tissues mediated by chemokines acting on their target cell receptors, or the proliferation of epithelial cells or the promotion of wound healing and/or an agent which modulates the expression or production of substances by cells in the body.

Specific examples of such biologically active agents include insulin, growth hormone, prolactin, calcitonin, luteinising hormone, parathyroid hormone, somatostatin, thyroid stimulating hormone, vasoactive intestinal polypeptide, a structural group 1 cytokine adopting an antiparallel 4 α helical bundle structure such as groEL, *Vibrio cholerae* toxin (ctxB), Pertussis toxoid, IL-2, IL-3, IL-4, IL-5, IL-6, IL-7, IL-9, IL-10, IL-11, IL-12, IL-13, GM-CSF, M-CSF, SCF, IFN-γ, EPO, G-CSF, LIF, OSM, CNTF, GH, PRL or IFN α/β, a structural group 2 cytokine which are often cell-surface associated, form symmetric homotrimers and the subunits take up the conformation of β-jelly roll described for certain viral coat proteins such as the tumour necrosis factor (TNF) family of cytokines, eg TNF α, TNF β, CD40, CD27 or FAS ligands, the IL-I family of cytokines, the fibroblast growth factor family, the platelet derived growth factors, transforming growth factor β and nerve growth factors, a structural group 3 cytokine comprising short chain α/β molecules, which are produced as large transmembrane pre-cursor molecules which each contain at least one epidermal growth factor (EGF) domain in the extracellular region, e.g., the EGF family of cytokines, the chemokines characterised by their possession of amino acid sequences grouped around conserved cysteine residues (the C-C or C-X-C chemokine subgroups) or the insulin related cytokines, a structural group 4 cytokine which exhibit mosaic structures such as the heregulins or neuregulins composed of different domains, e.g., EGF, immunoglobulin-like and kringle domains.

Alternatively, the biologically active agent can be a receptor or antagonist for a biologically active agent, as defined above.

The essential gene and the gene of interest are operably-linked to a promoter. The term "operably-linked" refers to a functional linkage between the regulatory sequence and a coding sequence. The components so described are thus in a relationship permitting them to function in their intended manner. By placing a coding sequence under regulatory control of a promoter means positioning the coding sequence such that the expression of the coding sequence is controlled by the promoter.

The synthetic operon of the present invention contains a promoter, which provides a site for RNA polymerase to bind and initiate transcription. The promoter may be homologous to the bacterial strain employed, i.e., one found in that bacterial strain in nature or may be heterologous. Typically, the promoter will be the same as the promoter used in the natural operon, for example, the T7 RNA polymerase promoter or the flagellin promoter. Other promoters include FlaB sigma 54 promoter (Josenhans et al., 1998, FEMS Microbiol Lett, 161 (2): 263-73), T7 promoter, arabinose inducible promoter, and nirB promoter of *Salmonella* (Chatfield et al., 1992, Biotechnology, 10(8): 888-92).

In another embodiment the promoter is inducible. Inducible promoters that may be used with the clinical grade vectors include, but are not limited to, a pH inducible promoter as described in U.S. Pat. No. 6,242,194 issued to Kullen et al., a lactose inducible promoter such as that used in *E. coli* plasmids (e.g., pBluescript™ from Stratagene) or the endogenous lactose promoter in *Lactobacillus*; promoters induced during anaerobic growth such as the promoter for alcohol dehydrogenase (adhE), as described in Aristarkhov et al., (1999), *J. Bacteriology*, Vol. 178(14), 4327-4332. A preferred promoter is the urease promoter from *Helicobacter*.

As described above, the present invention provides a synthetic operon that expresses a gene of interest that typically will encode a biologically active agent. The synthetic operon may be constructed de novo, or alternatively, be created from an existing operon. Accordingly, in some embodiments, a synthetic operon is created by inserting a gene of interest into a naturally-occurring operon in situ that encodes a gene essential to the bacterium. The term "naturally-occurring operon", as used herein, refers to an operon that is native to the bacteria. For example, the eight-gene operon yaeT-hlpA-lpxD-fabZ-lpxA-lpxB-rnhB-dna of *Escherichia coli* or the yycFG operon of *Bacillus subtilise* or the groES-groEL operon of *Escherichia coli* are all useful naturally-occurring operons that would be useful in the present invention.

In some embodiments, the operon is the urease operon, which is expressed constitutively in *Helicobacter pylori*. The urease operon of *H. pylori* is essential for colonisation of the stomach and allows the bacteria to survive in the acidic gastric environment. The corresponding gene product is the urease enzyme complex. The endogenous constitutive promoter of the urease operon avoids the need to supply an inducer or other regulatory signal for expression to take place. Preferably, the promoter directs expression at a level at which the *H. pylori* host cell remains viable, i.e., retains some metabolic activity, even if growth is not reduced. Advantageously, expression may be at a lower level. For example, where the expression product accumulates intracellularly, the level of expression may lead to accumulation of the expression product at less than about 10% of cellular protein, preferably about or less than about 5%, for example about 1-3%.

Urease is constitutively produced at high level, is up-regulated by acidic conditions and accounts for up to 10% of the wet weight of the bacteria. Urease also allows for neutralization of the acidic pH of the stomach by cleavage of urea into ammonia and carbonate. The ammonia in turn protects the bacteria from acidic killing and provides a buffer so the bacteria can swim to the more pH neutral acidic mucus layer of the stomach. Therefore, the urease operon represents an ideal candidate for use in the present invention.

Whether the synthetic operon is created de novo or created by inserting the gene of interest into a naturally-occurring operon, the synthetic operon is integrated into the chromosome of the bacterial host cell. Integration of the synthetic operon into the chromosome of the bacteria provides greater stability of expression than expression from a plasmid.

An expression vector and/or vector plasmid (hereinafter referred to collectively as "vector(s)") will generally be employed to insert the synthetic operon (or the gene of interest in the form of an isolated nucleic acid) into the bacterial chromosome.

The vector may comprise one or more sequences that promote integration and expression in the bacterial host cell. Suitable vectors comprising nucleic acid for introduction into a bacterial host cell chromosome can be chosen or constructed, to contain appropriate regulatory sequences, including terminator fragments, enhancer sequences, marker genes and other sequences as appropriate. Vectors may be plasmids, viral eg. phage or phagemid, as appropriate. For further details see, for example, Sambrook et al., supra. There are many known techniques and protocols for the manipulation of nucleic acid, for example in preparation of nucleic acid constructs, mutagenesis, sequencing, introduction of DNA into cells and gene expression, and analysis of proteins, are described in detail in "Short Protocols in Molecular Biology", Second Edition, Ausubel et al. eds., John Wiley & Sons, 1992. The disclosures of Sambrook et al. supra and Ausubel et al. are incorporated herein by reference.

By way of example, genetic manipulation of *H. pylori* may involve the construction of a novel synthetic urease operon by inserting the gene of interest between the ureA and ureB genes or after ureB such that the transcription of the gene of interest is linked to subunits A and B of the urease complex that are essential for *H. pylori* colonization and in vivo survival.

In some embodiments, the vectors of the present invention also include a toxic gene. These toxic genes are preferably under the control of inducible promoters so that, on completion of treatment, the bacteria can be readily eliminated by inducing the expression of the toxic gene. Non-limiting examples of toxic genes include bacterial autolysins under the control of an inducible promoter.

The vectors of the present invention may further comprise a secretory signal sequence. Thus, in some embodiments the nucleic acid encoding the biologically active agent may provide for secretion of the agent at a cell membrane by appropriately coupling a nucleic acid sequence encoding a secretory signal sequence to the nucleic acid sequence encoding the molecule (polypeptide). The ability of bacteria harbouring the nucleic acid to secrete the polypeptide may be tested in vitro in culture conditions.

Secretory signal sequences may include the secretion leader of the Staphylokinase enzyme secreted by some strains of *Staphylococcus*, which is known to function in both Gram-positive and Gram-negative hosts (see Rapoport (1990) Curr Opin Biotech 1:21-27).

Other secretory signal sequences that can be used include, for example, the β-lactamase gene (Talmadge et al., 1980, Proc. Natl. Acad. Sci. USA 77:3369-3373) or the enteroinvasive *E. coli* hemolysin A (hlyA) (Su et al., 1992, Microbial Pathogen, 13:465-476). An illustrative list of secretory signal sequences is presented in Pugsley, 1988, "Protein secretion across the outer membrane of gram-negative bacteria." In: "Protein Transfer and Organelle Biogenesis", R. C. Dand and P. W. Robbins (eds), Academic Press, Inc., San Diego, pp 607-652.

Selectable markers provide researchers and technicians a convenient means for distinguishing transformed microorganisms from non-transformed ones in a mixed population.

One means of identifying transformed organism is to incorporate a selectable marker nucleic acid sequence into the plasmid containing the gene of interest. The selectable marker sequence is generally inserted downstream of the gene of interest and is driven off the same promoter. As a result, cells successfully transformed with the gene of interest will also be transformed with selectable marker nucleic acid sequence.

Alternatively, an essential "house-keeping" gene may be inserted into a vector encoding for a gene of interest allowing for the rapid isolation and identification of transformants.

Examples of essential "house-keeping" genes include genes that encode for any number of metabolic regulators and/or enzymes including, but not limited to kinases, proteases, synthetases, dehydrogenases and others.

Other non-limiting examples of reporter genes used in accordance with the teachings of the present invention include green fluorescent Protein (GFP), β-galactosidase and amylase.

In some embodiments, the vector comprising a synthetic operon or an isolated nucleic acid, as described above, is introduced into a bacterium or other suitable bacterial host cell, to provide transformed cells.

The transformation of a culture of bacterial cells may employ any available technique. In one embodiment, $H.$ $pylori$ are naturally transformed overnight.

The introduction of the vector into a bacterial host cell may be followed by causing or allowing expression of the isolated nucleic acid, e.g., by culturing the bacteria under conditions for expression of the gene. Growing the bacteria in culture under conditions for expression of the biologically active agent may be employed to verify that the bacteria contain the encoding nucleic acid and is able to produce the encoded material.

Transformed cells expressing the biologically active agent may be administered to any animal in need of the biologically active agent expressed by the transformed cells. Specifically, animal includes, but is not limited to, primates (including humans), bovine, equine, canine, feline, porcine, ovine, rabbits, rodents, birds and fish.

After administration of the transformed bacteria, the bacteria will begin to express the biologically active agent. As such, the present invention provides a method of expressing a gene of interest in a bacterium involving the following steps: (i) constructing a synthetic operon according to the present invention; (ii) integrating the synthetic operon into the chromosomal DNA of a bacterium; and (iii) culturing the bacterium in order to express the gene of interest.

Alternatively, the present invention provides a method of expressing a gene of interest in a bacterium involving the following steps: (i) identifying an operon that encodes an essential gene; (ii) inserting a gene of interest into the chromosomal DNA of a bacterium into said operon to produce a synthetic operon such that the gene of interest is co-transcribed with the essential gene; and (iii) culturing said bacterium in order to express said gene of interest.

The expression of the gene of interest may be in vitro or in vivo expression.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The invention will now be further described by way of reference only to the following non-limiting examples. It should be understood, however, that the examples following are illustrative only, and should not be taken in any way as a restriction on the generality of the invention described above.

Example 1

Bacterial Cultures

A streptomycin resistant mutant of $H.$ $pylori$ strain X47 was used for all experiments. Bacteria were grown on Brain Heart Infusion (BHI) based agar plates supplemented with 5% horse blood and when appropriate, erythromycin (10 µg/mL) or streptomycin (10 µg/mL) in an atmosphere containing 5% $CO_2$. $H.$ $pylori$ producing functional urease were selected on BHI based agar plates supplemented with 7% (v/v) horse serum, phenol red (100 mg/L), and urea (600 mg/L). Media was acidified using 1M HCl to a yellow colouration.

Example 2

Natural Transformation of $H.$ $pylori$

Overnight cultures of $H.$ $pylori$ grown on BHI based agar plates were sub-cultured onto plates supplemented with DENT (Oxoid) in lawns of approximately 2 cm in diameter. Transformation was performed by the addition of approximately 1 µg of purified PCR product after growth of bacterial lawns for 6-8 hrs. After overnight incubation putative transformants were streaked on selective media.

Example 3

DNA Constructs

All DNA constructs were made by PCR. However, to facilitate the construction of the recombinant $H.$ $pylori$, two plasmids were constructed to insert the gene of interest in the urease locus by natural transformation and homologous recombination. The flanking sequences of the urease operon were amplified by PCR and EcoRI/BglII restriction sites were introduced. In brief, flanking urease sequences were produced by fusion and cloning in pBluescript SK(−) and involved performing a 2 way fusion PCR by i) amplification of two products for splicing by overlapping extension PCR (Table 1), ii) fusion PCR iii) cloning as a ClaI/NotI fragment in modified pBluescript SK(−) with XhoI and SalI sites deleted by restriction endonuclease digestion and religation. The resulting plasmid was the recipient for the heterologous gene of interest or the RpsI-CAT counter-selection cassette to construct the $H.$ $pylori$ recipient strain.

Example 4

Insertion of the Gene of Interest Between Urease A and B Subunits: pAB Plasmid

Flanking urease gene sequences were fused by PCR in order to insert an EcoRI and BglII restriction sites between the ureA and ureB (Table 1).

TABLE 1

PRIMERS AND TEMPLATES

| Purpose | Product | Primer 1 | Primer 2 | Annealing temperature | Fragment length | Template |
|---|---|---|---|---|---|---|
| Ure AB gene of interest, ureA | A | UreA for AB F MB180908 ACGGTATCGATAAGCTTAGCACTAC CTTGACATGGTAGTG (SEQ ID NO: 5) | UreA for AB R MB180908 TTCAGATCTGAATTCTTACTCCTTAA TTGTTTTTACATAGTTG (SEQ ID NO: 6) | 52 | 1031 | Genomic DNA |
| Ure AB gene of interest, ureB | B | UreB for AB F MB180908 GAGTAAGAATTCAGATCTGAAATG AAAAAGATTAGCAGAAAAGAATATG (SEQ ID NO: 7) | UreB for AB R MB180908 AACTGATCTAGAGGATCCTTGAATC AGCGAACTGAAC (SEQ ID NO: 8) | 52 | 1034 | Genomic DNA |
| | FUSION | UreA for AB F MB180908 | UreB for AB R MB180908 | 55 | 2065 | Products A and B |
| After ureB gene of interest, ureB | A | UreB for BI F MB180908 GACGGTATCGATAAGCTTCATGCGT TAGATGTTGCAGACAAATAC (SEQ ID NO: 9) | UreB for BI R MB180908 GACAAAAAATAAAAAGATCTGAATT CACAAAAAAAGCCCCCAATTTTTG (SEQ ID NO: 10) | 52 | 1110 | Genomic DNA |
| After ureB gene of interest, ureI | B | UreI for BI F MB180908 GTGAATTCAGATCTTTTTATTTTTTG TCAATTTACTATTTTTCTTTATG (SEQ ID NO: 11) | UreI for BI R MB180908 AACTATCTAGAGGATGTGAATGACT TCAGAATCCAAG (SEQ ID NO: 12) | 52 | 952 | Genomic DNA |
| | FUSION | UreB for BI F MB180908 | UreI for BI R MB180908 | 55 | 2062 | Products A and B |

EcoRI and BglII restriction sites were used to clone the gene of interest for expression from the urease operon. Neither the ribosome binding site nor termination sequence were added to allow the ribosome to read through the urease operon: ureA, the cloned gene of interest and ureB. The rpsL-CAT cassette was cloned as a BamHI DNA fragment in pAB and the resulting plasmid was used to transform *H. pylori* to insert the rpsL-CAT cassette at the urease operon in order to construct the urease negative recipient. Replacement of the rpsl-CAT counter-selection cassette was performed by natural transformation of the latter recipient strain with the gene of interest of interest. Urease selection plates were used to recover the recombinant strains harbouring the gene of interest and determine urease activity.

Example 5

Insertion of the Gene of Interest after the Urease B Subunit: pBI Plasmid

Flanking urease genes sequences were fused by PCR in order to insert an EcoRI and BglII restriction sites after ureB (Table 1). EcoRI and BglII restriction sites were used to clone the gene of interest for expression from the urease operon. No ribosome binding sequence (RBS) was added and the following RBS sequence (AGGATACAAA) (SEQ ID NO:13) was included in the primer for amplification and cloning of the gene of interest. The additional RBS will ensure the efficient transcription of the heterologous gene of interest after termination of ureB. The rpsL-CAT cassette was clone as a BamHI DNA fragment in pBI and the resulting plasmid used to transform *H. pylori* to insert the rpsL-CAT cassette at the urease operon in order to construct the urease negative recipient. Replacement of the rpsl-CAT counter-selection cassette was performed by natural transformation of the latter recipient strain with the gene of interest. Urease selection plates were used to recover the recombinant strains harbouring the gene of interest and determine urease activity.

Example 6

DNA Sequencing of pAB and pBI

DNA sequencing of pAB and pBI plasmids confirmed the correct assembly of the urease operon flanking sequences by fusion PCR. The EcoRI/BglII restriction sites for cloning of the gene of interest were also confirmed (FIGS. 4 and 6).

Example 7

Insertion of Genes of Interest at the AB and BI Loci

1) GFP at the AB Locus

DNA coding GFP mut-2 was amplified with Accuprime™ polymerase supermix and fused to the signal sequence of vacA for periplasmic targeting. Amplicons and plasmid pAB were digested sequentially with BglII and EcoRI. Plasmid was additionally treated with calf intestine alkaline phosphatase and proteinase K. Both digested plasmid and amplicon were purified using a PureLink™ PCR purification kit (Invitrogen), ligated and transferred to *E. coli* DH5-alpha via the heat shock method. The resulting plasmid pABGFP (FIG. 7) harboured gfp-mut2 (including a sec-dependent secretion signal) flanked by two regions for homologous recombination at the ureAB locus (between ureA and ureB).

2) groEL at the BI Locus

The *H. pylori* groEL gene was tagged with the CTP3 Cholera toxin epitope and flanking sequences of the urease operon were fused to it by PCR. The resulting DNA fragment (FIG. 8) was used to transform *H. pylori* and urease positive clones were recovered.

3) GFP at the BI Locus

Figure 7:
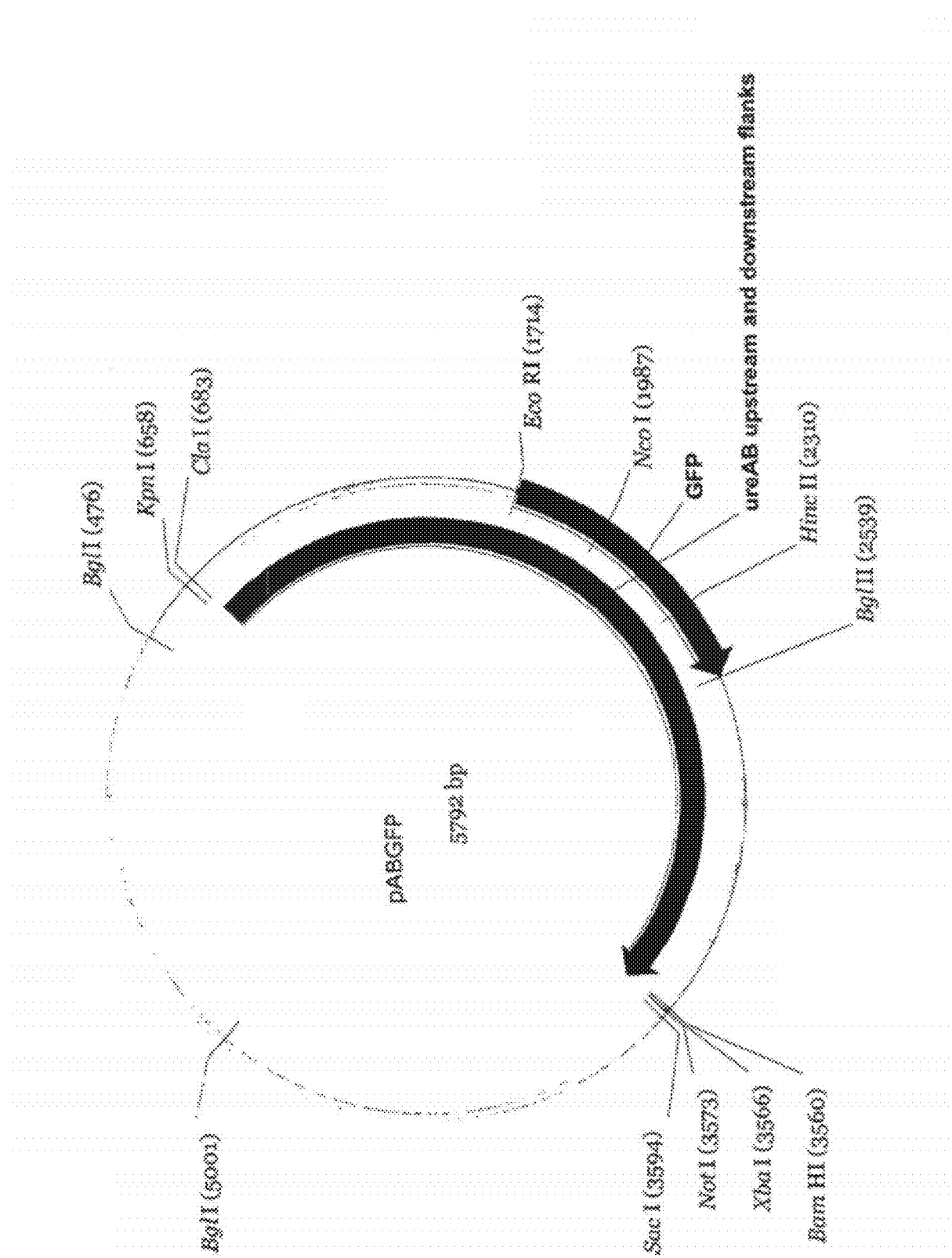
FIG. 7: A plasmid map of pABGFP.

DNA coding GFP mut-2 was amplified with Accuprime polymerase supermix and fused to the signal sequence of vacA for periplasmic targeting. Amplicons and plasmid pBI were digested sequentially with BglII and EcoRI. Plasmid was additionally treated with calf intestine alkaline phosphatase and proteinase K. Both digested plasmid and amplicon were purified using a PureLink™ PCR purification kit (Invitrogen), ligated and transferred to *E. coli* DH5-alpha via the heat shock method. The resulting plasmid pBIGFP harboured gfp-mut2 (including sec dependent secretion signal) flanked by two regions for homologous recombination at the ureAB locus after ureB (FIG. 7).

The two plasmids, pAB and pBI, were used to clone the GFP gene in the EcoRI/BglII restriction sites. Natural transformation of the urease negative recipient strain of *H. pylori* (harbouring the rpsl-CAT cassette between ureA and ureB and after the ureB, respectively) with plasmids pABGFP and pBGFP gave rise to many colonies on urease selective plates, indicating that the homologous recombination event took place producing a functional urease synthetic operon. Diagnostic PCR, performed with genomic DNA of recombinant strains, demonstrated that GFP had been inserted in between ureA and ureB and after ureB, respectively (data not shown). Similar results were obtained when the groEL CTP3 fusion was inserted after the ureB gene, demonstrating that the synthetic urease operon can accommodate different genes of interest and retain ureA and ureB expression for functional urease complex assembly.

Example 9

Western Blot Analyses

To determine if recombinant *H. pylori* strains expressed groEL fused to CTP3 or GFP, Western Blot analysis was performed. Fused proteins were detected with an anti-Cholera toxin and anti-GFP antibody by using standard Western Blot protocols.

Figure 9:
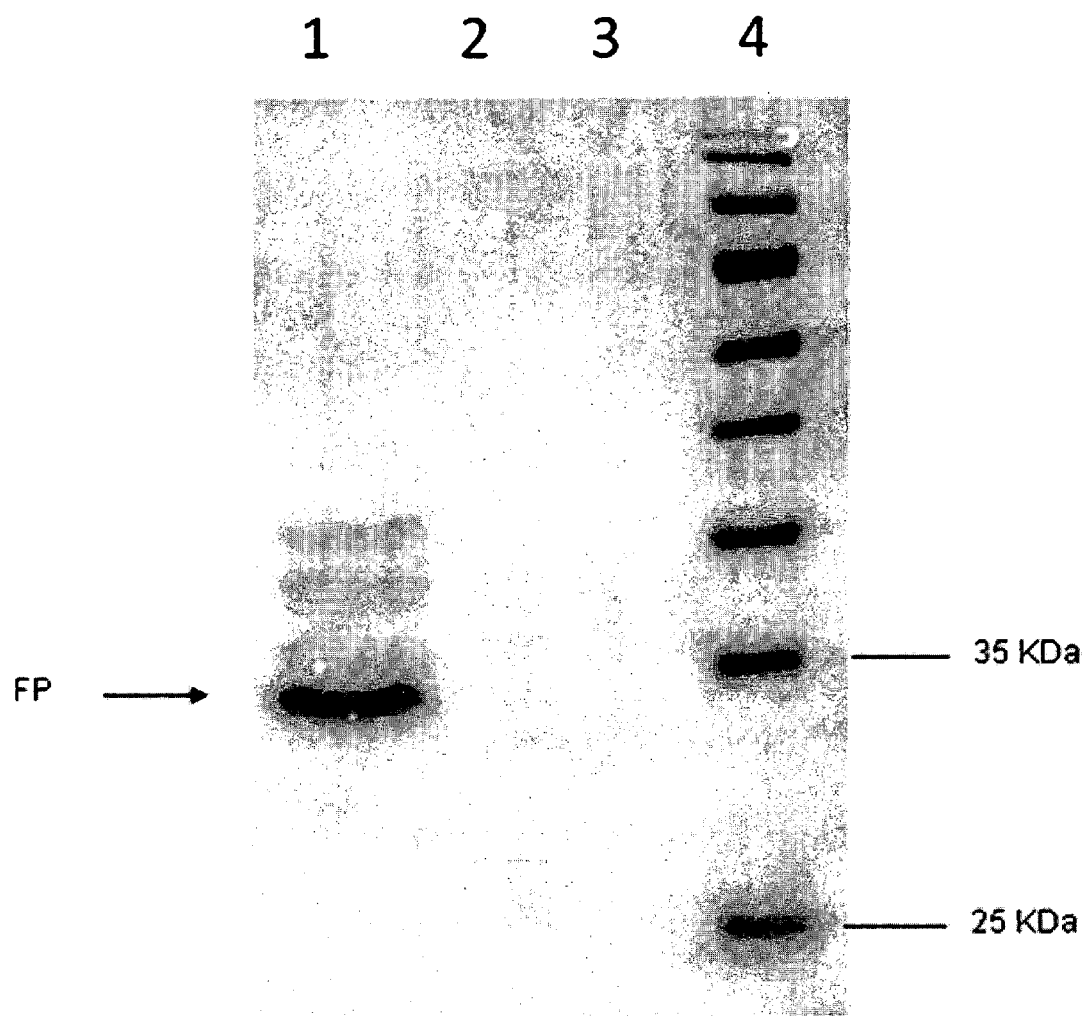
FIG. 9: Western blot analysis of *H. pylori* expressing GFP inserted between ureA and ureB. Lane 1: X47 pABGFP; Lane 2: no sample; Lane 3: X47 (wild type); Lane 4: Marker.
Figure 10:
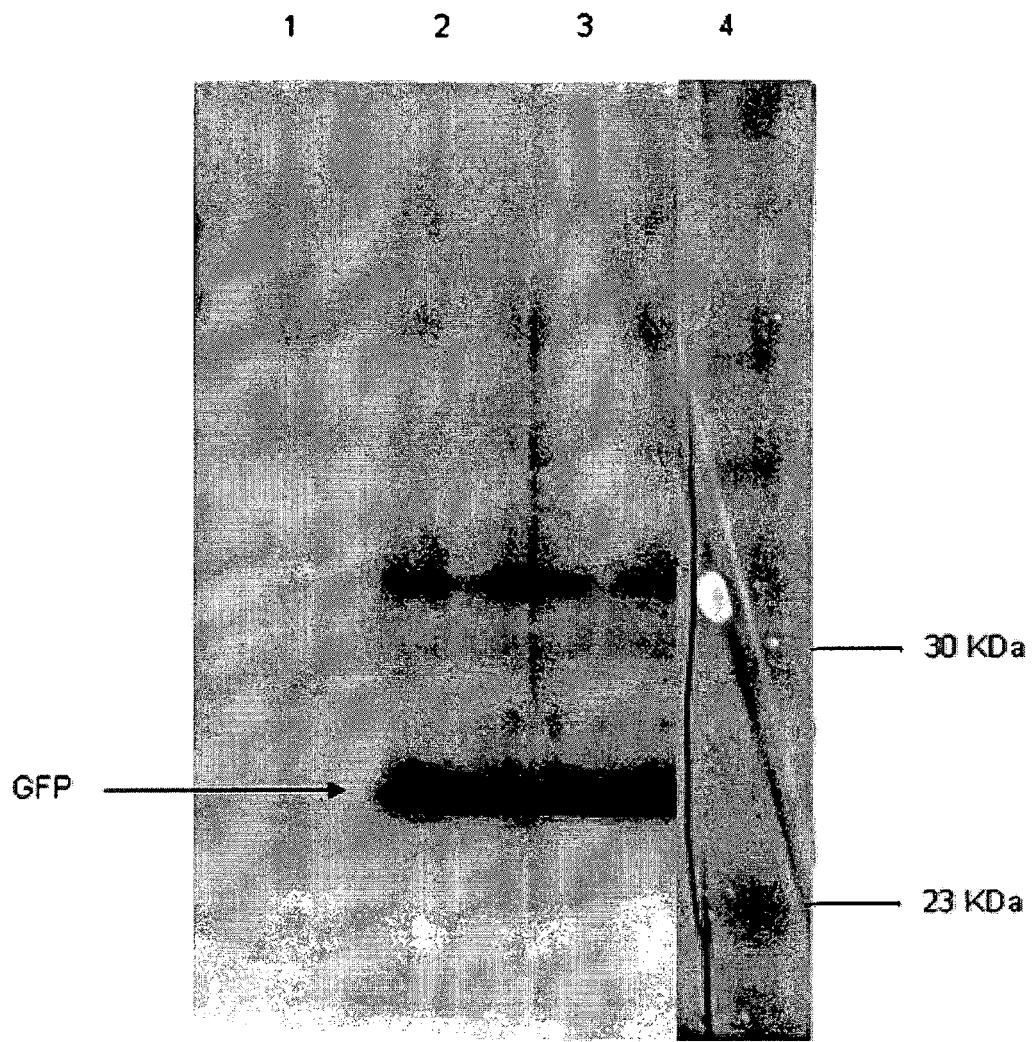
FIG. 10: Western blot analysis of *H. pylori* expressing GFP inserted after the ureB. Lane 1: X47; Lane 2: X47 pBI GFP; Lane 3: X47 pBI GFP; Lane 4: Marker.
Figure 11:
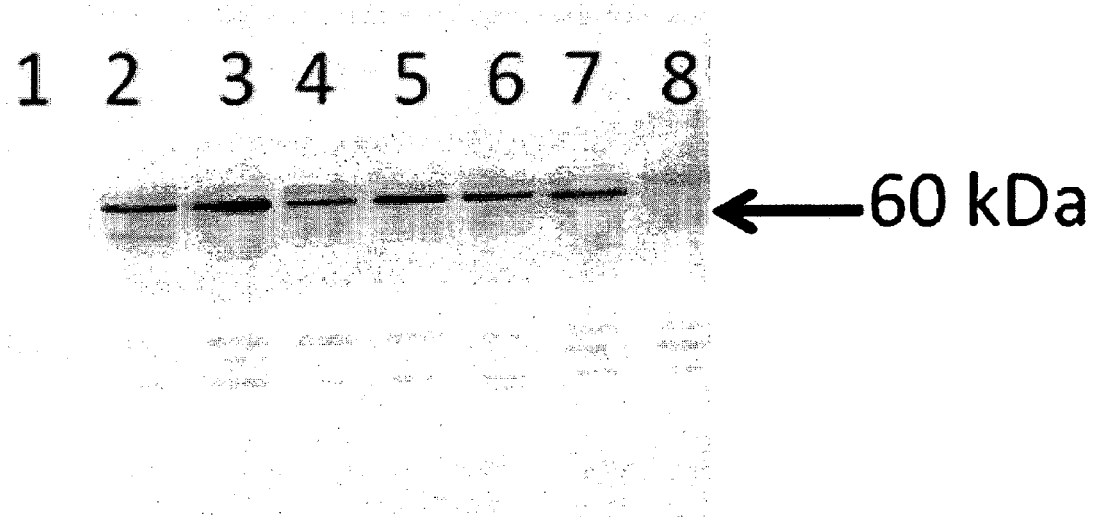
FIG. 11: Western blot analysis of *H. pylori* expressing groEL CTP3 after ureB. Lane 2 to 7: 6 clones of X47 groEL CTP3; Lane 8: X47 (wild type); Lane 1: Marker.

Western blot analysis of both the GFP and groEL fusions demonstrated that all fusions were expressed. A strong expression level was observed when the GFP was inserted between ureA and ureB (FIG. 9) and a slightly lower expression level was observed when GFP was inserted after ureB (FIG. 10). A similar expression level of the groEL CTP3 fusion was observed when inserted after ureB (FIG. 11).

Example 10

Experimental Infection of Mice

Female C57BL/6, *Helicobacter* free mice were purchased from the Animal Resource Centre (Perth, Western Australia). Studies were performed with approval from the UWA Animal Ethic Committee (approval no. RA 3/100/598). Eight week old mice were orogastrically inoculated with approximately $1.0 \times 10^9$ *H. pylori* harvested from an overnight agar plate based culture in BHI broth (Oxoid). To determine the level of colonization, stomachs were harvested from sacrificed animals, opened, and residual food removed. Opened stomachs were suspended in 500 μL PBS and homogenized using 5 mm stainless steel beads for 30 seconds at setting of 30 (Qiagen Tissue Lyser). Samples were then homogenized for a further 2 minutes at setting of 10. Serial dilutions of homogenates were plated on BHI based agar plates supplemented amphotericin B (8 μg/mL), trimethoprim (5 μg/mL) and vancomycin (6 μg/mL), Nalidixic acid (10 μg/mL), polymyxin B (10 μg/mL) and bacitracin (200 μg/mL). Bacterial growth was determined 5-7 days post plating.

96 well plates (Nunc Maxisorb®) were coated with 10 μg/ml of Cholera CTP3 peptide and incubated O/N at 4° C. Plates were then washed 5 times in PBS/0.05% Tween-20 and blocked with 2% BSA for 2 hours at 37° C. Plates were washed twice and serum samples (1/20 dilution) were added to the well in duplicate. The plates were then incubated for 1 hour at room temperature, subsequently washed and detection antibody (anti-mouse IgG conjugated to alkaline phosphatase, 1/1000, Sigma) was added. Plates were further incubated for 1 hour at room temperature then washed. Plates were developed using p-NPP for 40 minutes before the reaction was stopped with 2M NaOH. Optical density values were measured at 405 nm.

In vivo experiments in a *H. pylori* mouse model showed that recombinant *H. pylori* strains expressing the CTP3 epitope fused to groEL in the synthetic urease operon after ureB were able to colonise the gastric mucosa. Five out of five clones tested colonised mice in vivo (Table 2).

TABLE 2

COLONISATION OF *H. PYLORI* STRAINS HARBORING THE SYNTHETIC UREASE OPERON: GROEL CTP3 AFTER UREB

| Hp strain | Description | Mouse strain | mouse 1 | Mouse 2 | mouse 3 |
|---|---|---|---|---|---|
| groEL CTP3 | Clone 1 | C57BL/6J | colonised | colonised | colonised |
| groEL CTP3 | Clone 2 | C57BL/6J | colonised | colonised | colonised |
| groEL CTP3 | Clone 3 | C57BL/6J | colonised | colonised | colonised |
| groEL CTP3 | Clone 4 | C57BL/6J | colonised | colonised | colonised |
| groEL CTP3 | Clone 5 | C57BL/6J | colonised | colonised | colonised |

Bacteria recovered from the mice were tested for expression of the gene of interest (groEL CTP3 or GFP, respectively).

Figure 12:
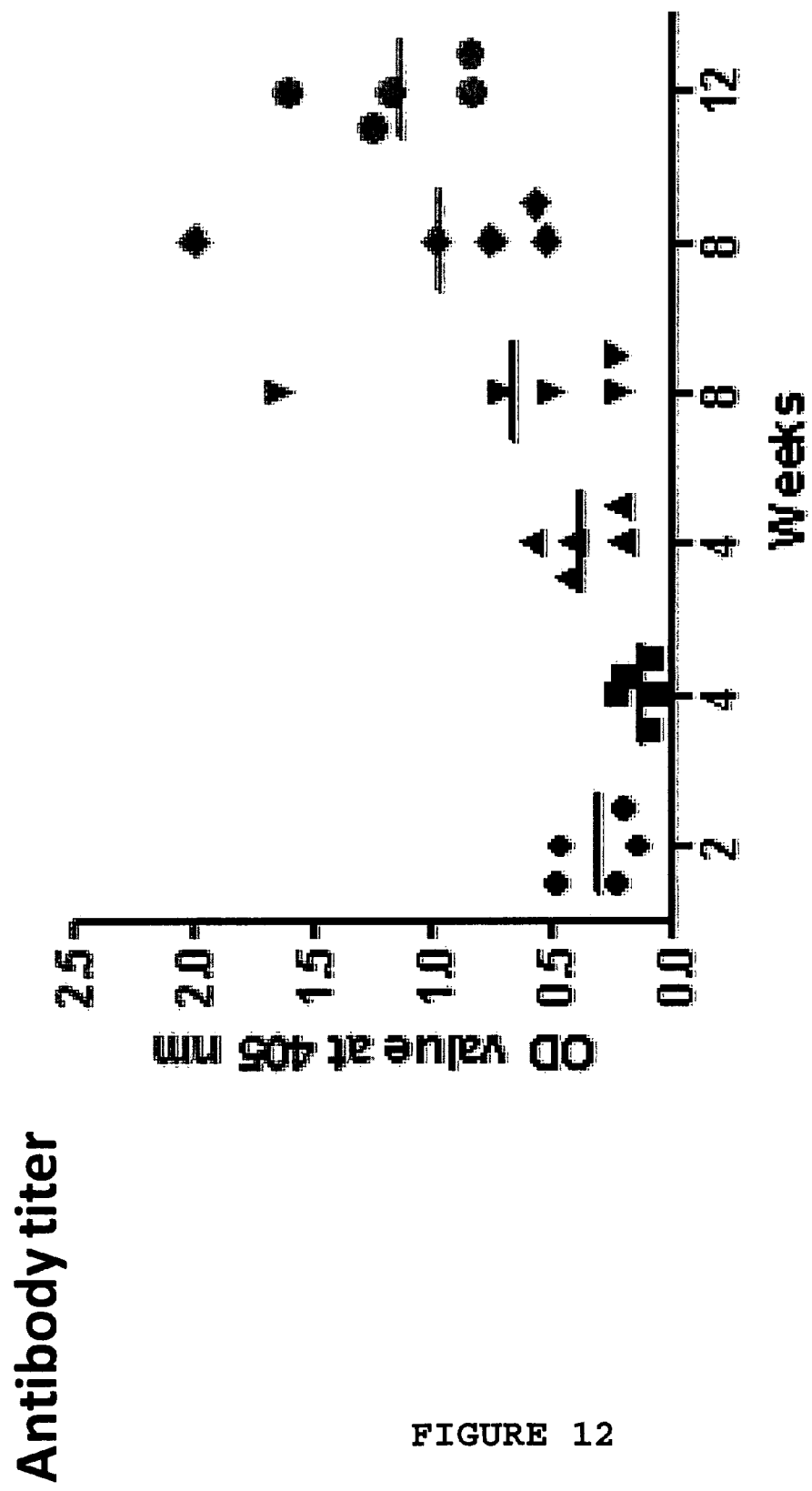
FIG. 12: Cholera toxin-specific antibody titres measured by ELISA.

Mice challenged with recombinant *H. pylori* expressing the CTP3 epitope fused to groEL were bled at week 2, 4, 8 and 12 weeks after challenge. The CTP3-specific antibody response was determined by standard ELISA. A CTP3-specific antibody response was detectable and increased over the course of the experiment (FIG. 12). This demonstrated that the synthetic operon is sufficient to sustain an expression level of the gene of interest over a long period of time, which is compatible for the induction and maintenance of a strong antibody response against a model antigen such as CTP3.

Example 11

Expression of Toxoids in *H. Pylori* and Use as Mucosal Adjuvants

The use of attenuated bacterial toxins (toxoid) that have lost their toxicity and retained their immunogenicity has been widely used in vaccine development. We investigated the use of toxoids as mucosal adjuvants by expressing them in *H. pylori*.

Figure 13:
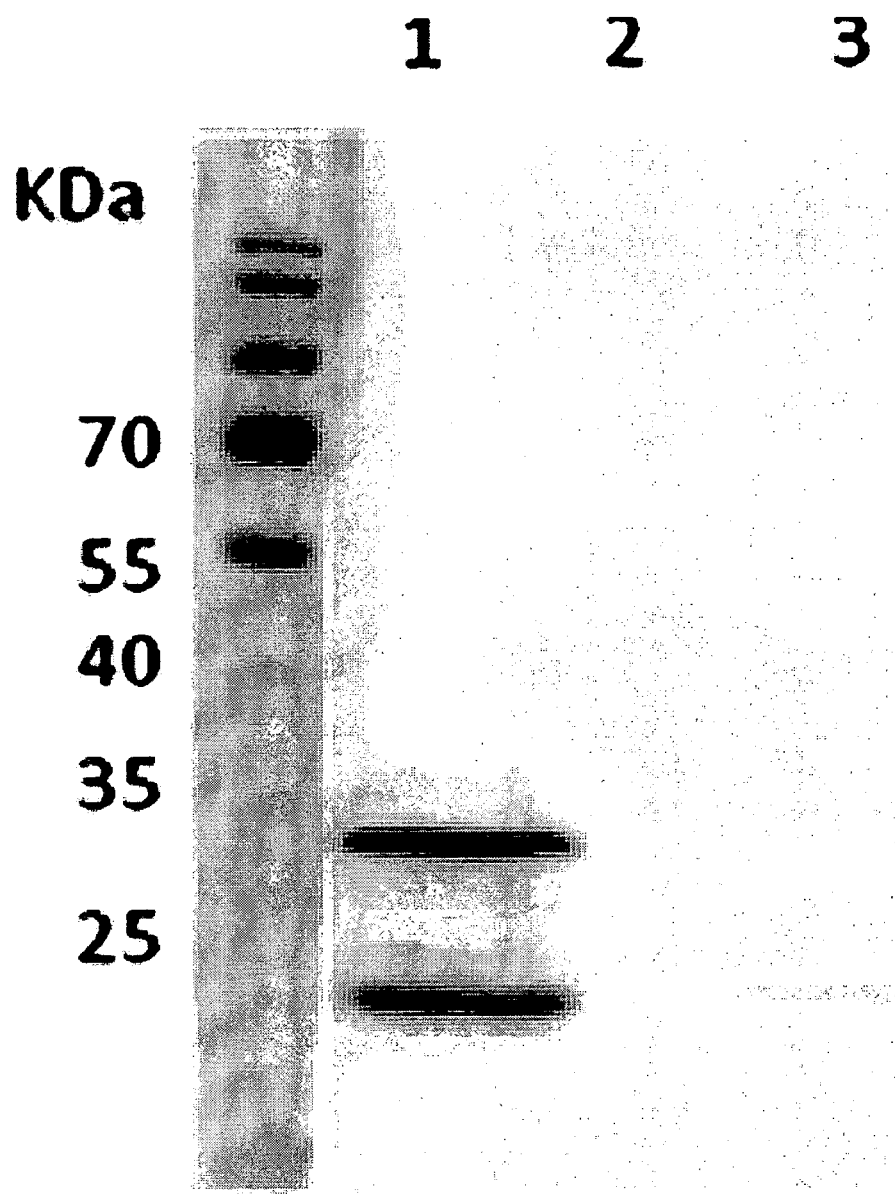
FIG. 13: Expression of the secreted S1 Pertussis toxoid. Anti-Pertussis toxoid antibodies detected the S1 fragment of the Pertussis toxoid (28 kDa) in recombinant *Helicobacter pylori* lane 1. A smaller protein band was also detected, corresponding to proteolytic cleavage. Lane 3 is the Wild type recipient strain. Lane 2 is an empty lane.

The S1 fragment of the Pertussis toxin (SEQ ID NO:14) was inserted between the urease A and B subunit using pAB plasmid for the construction of a synthetic operon and expression from the strong urease promoter. In order to promote secretion of the toxoid, the vacA signal peptide was added at the N-terminus. FIG. 13 shows the sequence of the S1 fragment fusion and its expression in *H. pylori*.

Figure 14:
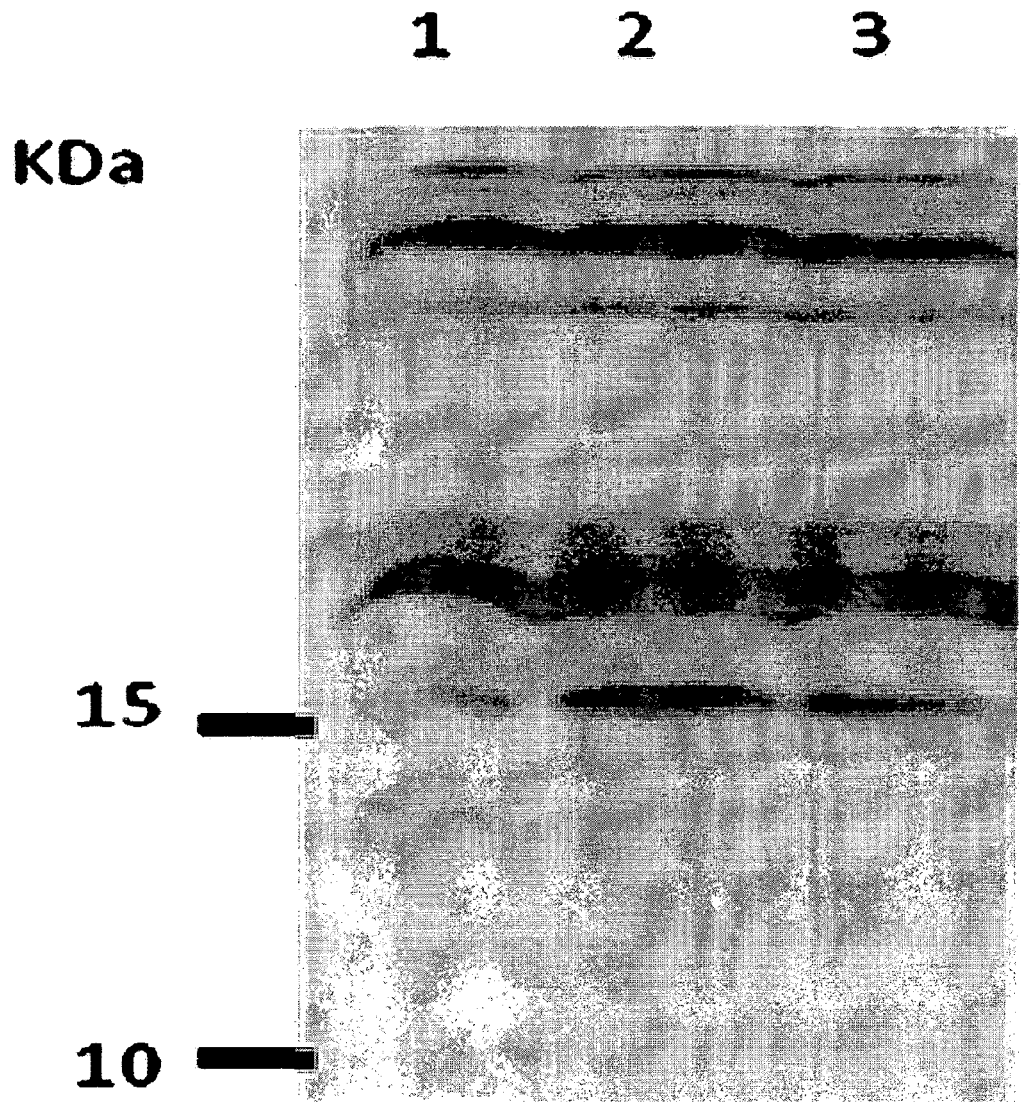
FIG. 14: Expression of the ctxB toxoid fusion. Anti-ctxB antibodies detected ctxB (13.5 kDa) in recombinant bacteria lane 1 and 2. Background protein bands were also detected in the Wild type recipient strain (lane 3).

The subunit B of the *Vibrio cholerae* toxin (ctxB) (SEQ ID NO:15) was inserted between the urease A and B subunits using pAB plasmid for the construction of a synthetic operon and expression from the strong urease promoter. In order to promote secretion of the toxoid, the vacA signal peptide was added at the N-terminus. FIG. 14 shows the ctxB fusion and its expression in *H. pylori*.

Example 12

Expression of Carrier Proteins and Antigens in *H. Pylori* and Use Thereof

Figure 15:
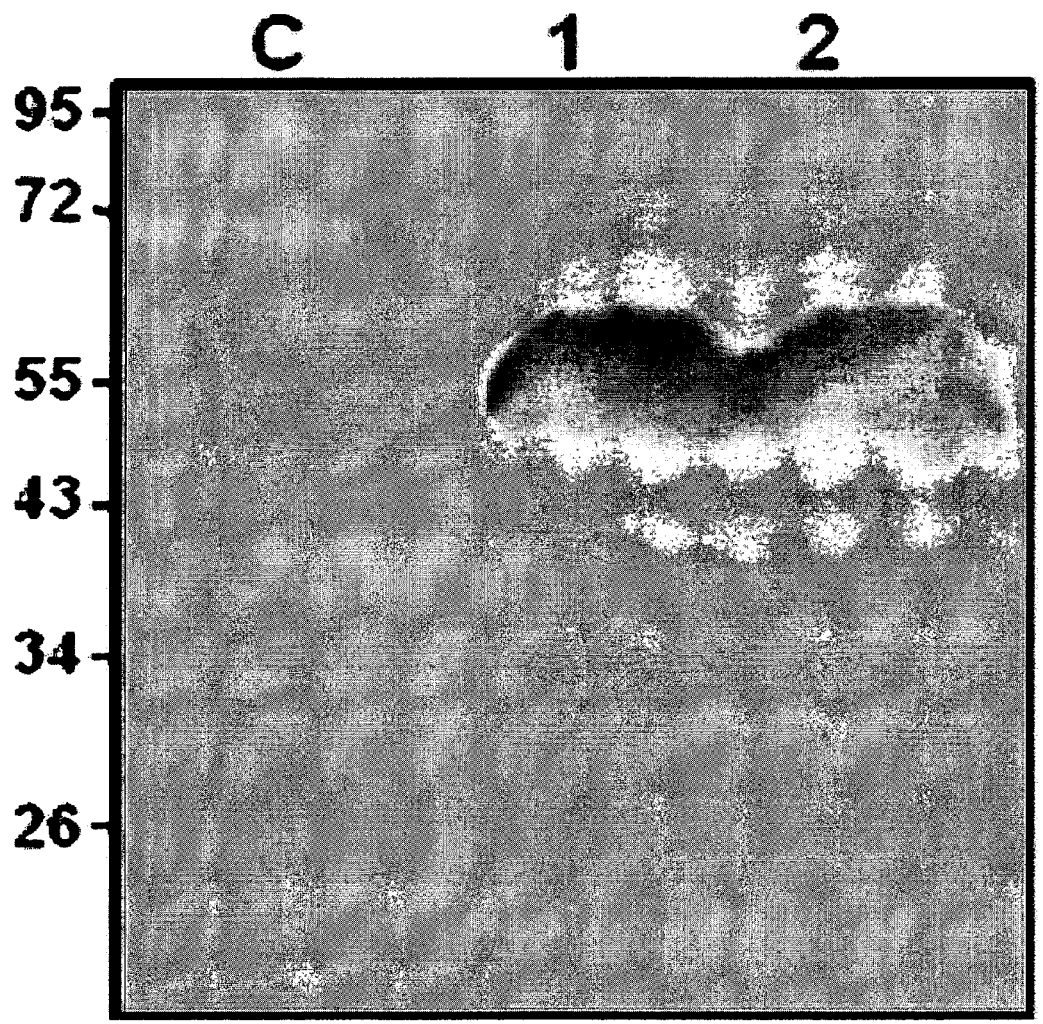
FIG. 15: Western analysis of recombinant bacteria. The CTP3 epitope was inserted between the signal peptide and the mature htrA protein. Western blot, lane 1 and 2 recombinant clones expressing the fusion of 51.6 kD between ureA and ureB. C; negative control. Antibody: anti-ctxB.

*H. pylori* htrA is highly immunogenic both in humans and mice and represents a protein carrier candidate for delivery of foreign antigens. The CTP3 model antigen was fused to the N-terminus of the mature protein and was inserted between the urease A and B subunits using pAB plasmid for the construction of a synthetic operon and expression from the strong urease promoter. FIG. 15 shows the expression of the CTP3-htrA fusion (SEQ ID NO:16) in *H. pylori*.

Figure 16:
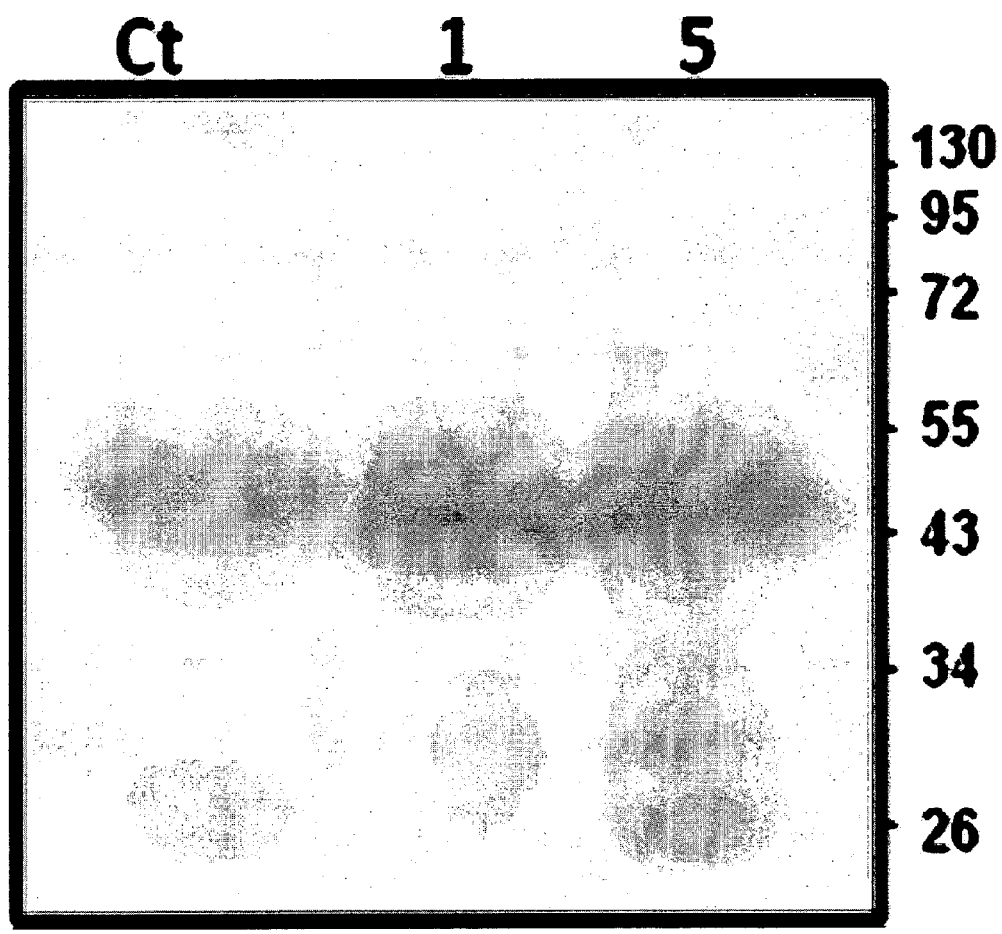
FIG. 16: Western analysis of recombinant bacteria. Western blot, lane 1 and 2 recombinant clones expressing the fusion of 48.6 kDa between ureA and ureB. Ct, negative control. Antibody: anti-haemagglutinin.

Lpp20 is a lipoprotein present of the surface of *H. pylori*. Additionally, *H. pylori* lpp 20 is highly immunogenic both in humans and mice. The haemagglutinin (HA) head of the Influenza virus (the main protective antigen for the Influenza vaccine) and 2 copies of the M2e epitope from the conserved M2 protein (HAM2) were fused to the C-terminus of lpp 20 and the fusion was inserted between the urease A and B subunits using plasmid pAB for the construction of a synthetic operon and expression from the strong urease promoter. FIG. 16 shows the expression of the lpp 20-HAM2 fusion (SEQ ID NO:17) in *H. pylori*.

Figure 17:
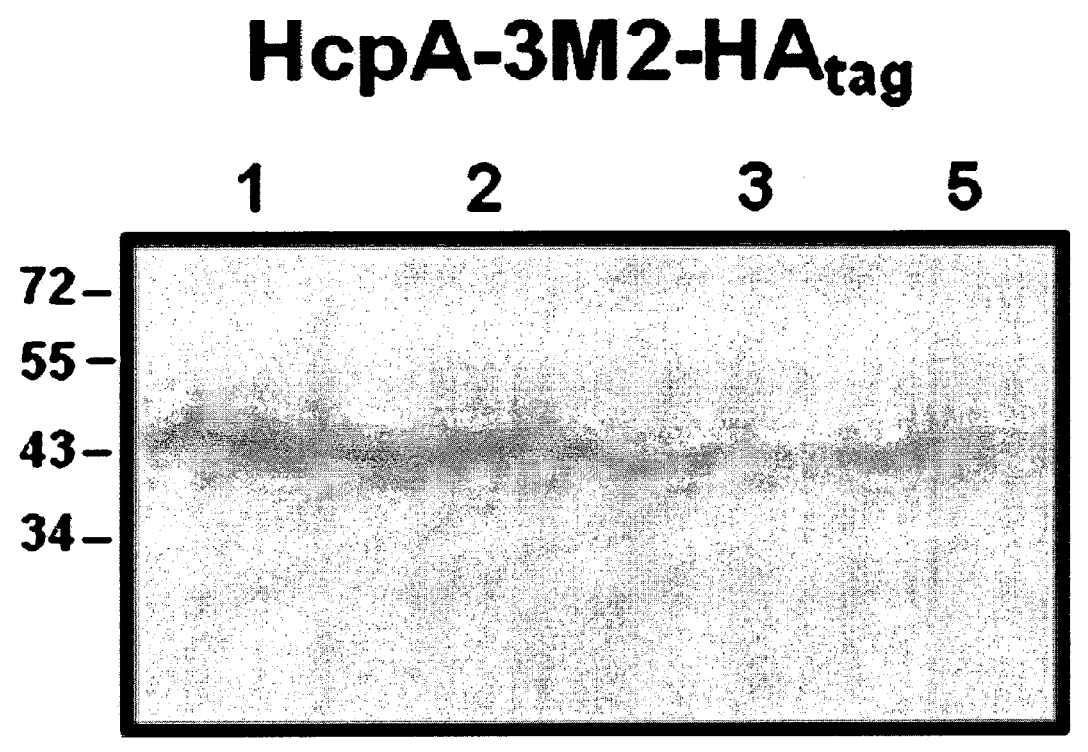

HcpA is a secreted protein that is highly stable and immunogenic. Epitopes from the haemagglutinin and M2e proteins (termed 3M2-HA tag) were inserted at the c-terminus of hcpA and the fusion was inserted between the urease A and B subunits using pAB plasmid for the construction of a synthetic operon and expression from the strong urease promoter. FIG. 17 shows the expression of the hcpA-3M2eHA tag fusion (SEQ ID NO:18) and its expression detected by Western blot using anti-Influenza antibodies.

Figure 18:
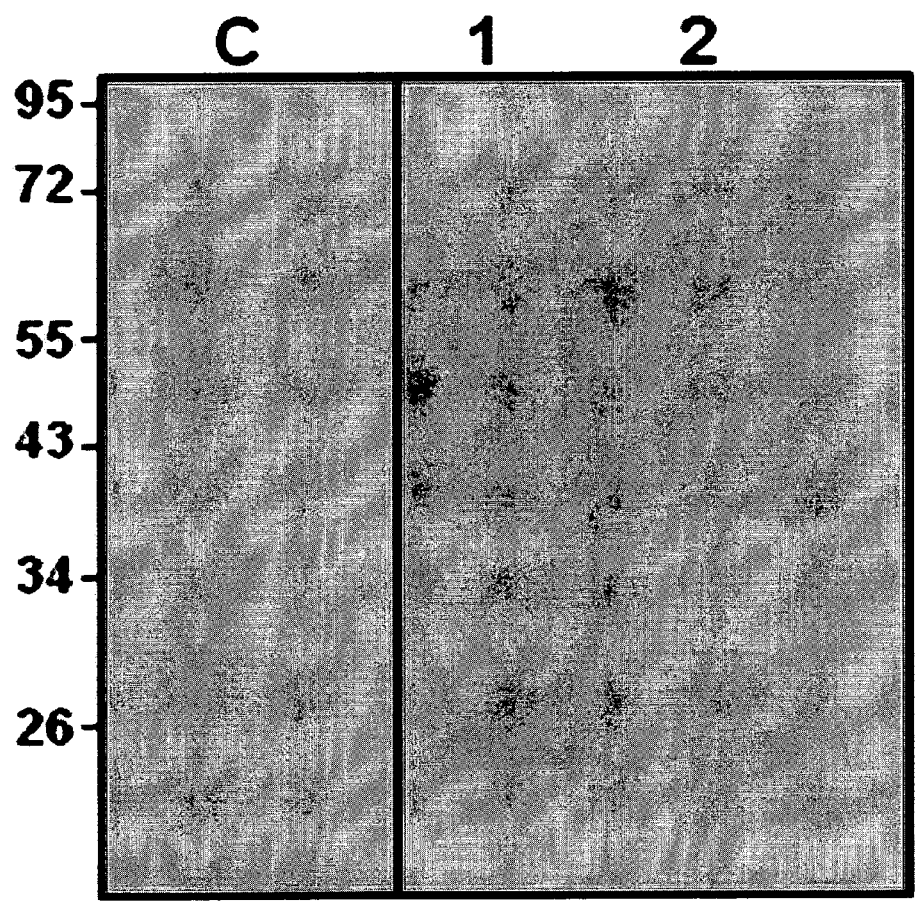
FIG. 18: Western analysis. Recombinant bacteria displayed a signal at 26.7 kD, lane 1 and 2. Lane c; negative control corresponding to the Wild type recipient strain. Antibody: anti-ctxB.

The CTP3 epitope was inserted at the C-terminus of hcpA and the fusion was inserted between the urease A and B subunits using pAB plasmid for the construction of a synthetic operon and expression from the strong urease promoter. FIG. 18 shows the expression of the CTP3-hcpA fusion (SEQ ID NO:19) detected by Western blot using anti-ctxB antibodies.

Example 13

Expression of Cell Binding Factors in *H. Pylori* and Use Thereof

Figure 19:
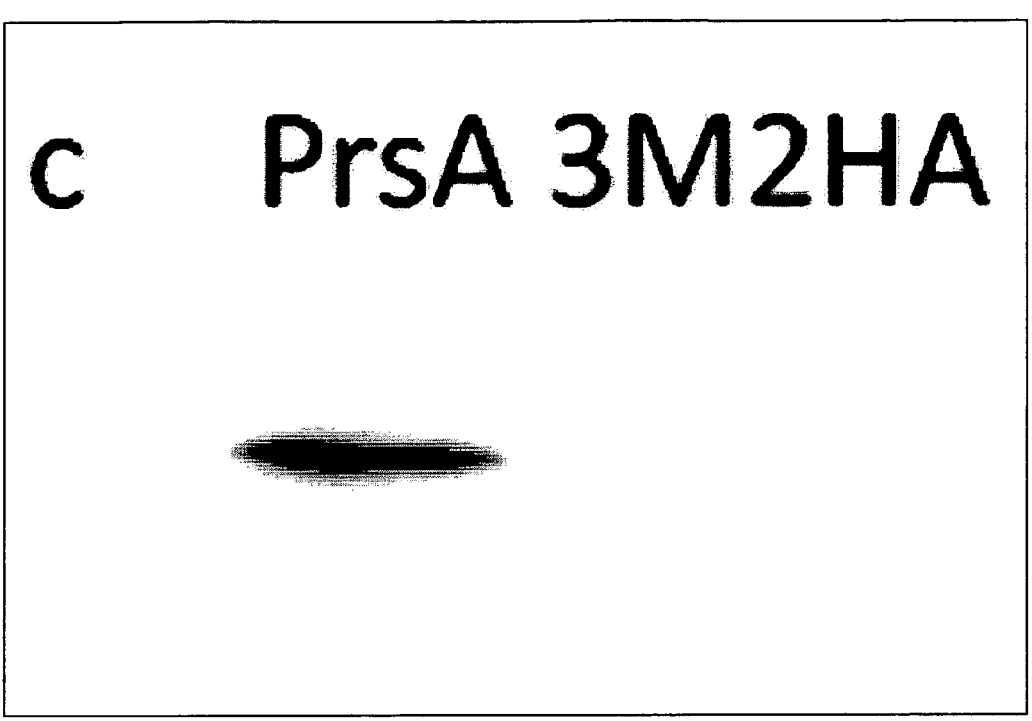
FIG. 19: Western analysis of recombinant bacteria. Western blot of a recombinant clone expressing the fusion between ureA and ureB. Lane c; negative control. Antibody: anti-haemagglutinin.

The cell binding factor (PrsA) is a highly immunogenic, secreted protein of *H. pylori*. It has been shown to interact with TLR4. Thus, PrsA is a potential candidate carrier protein for antigen delivery. The Influenza epitope tag 3M2HA was fused at the PrsA C-terminus. The fusion was inserted between the urease A and B subunits using pAB plasmid for the construction of a synthetic operon and expression from the strong urease promoter. FIG. 19 shows the expression of the PrsA-3M2HA fusion (SEQ ID NO:20) detected by Western blot using anti-Influenza antibodies.

Example 14

Expression of GroEL in *H. Pylori* and Use Thereof

Figure 20:
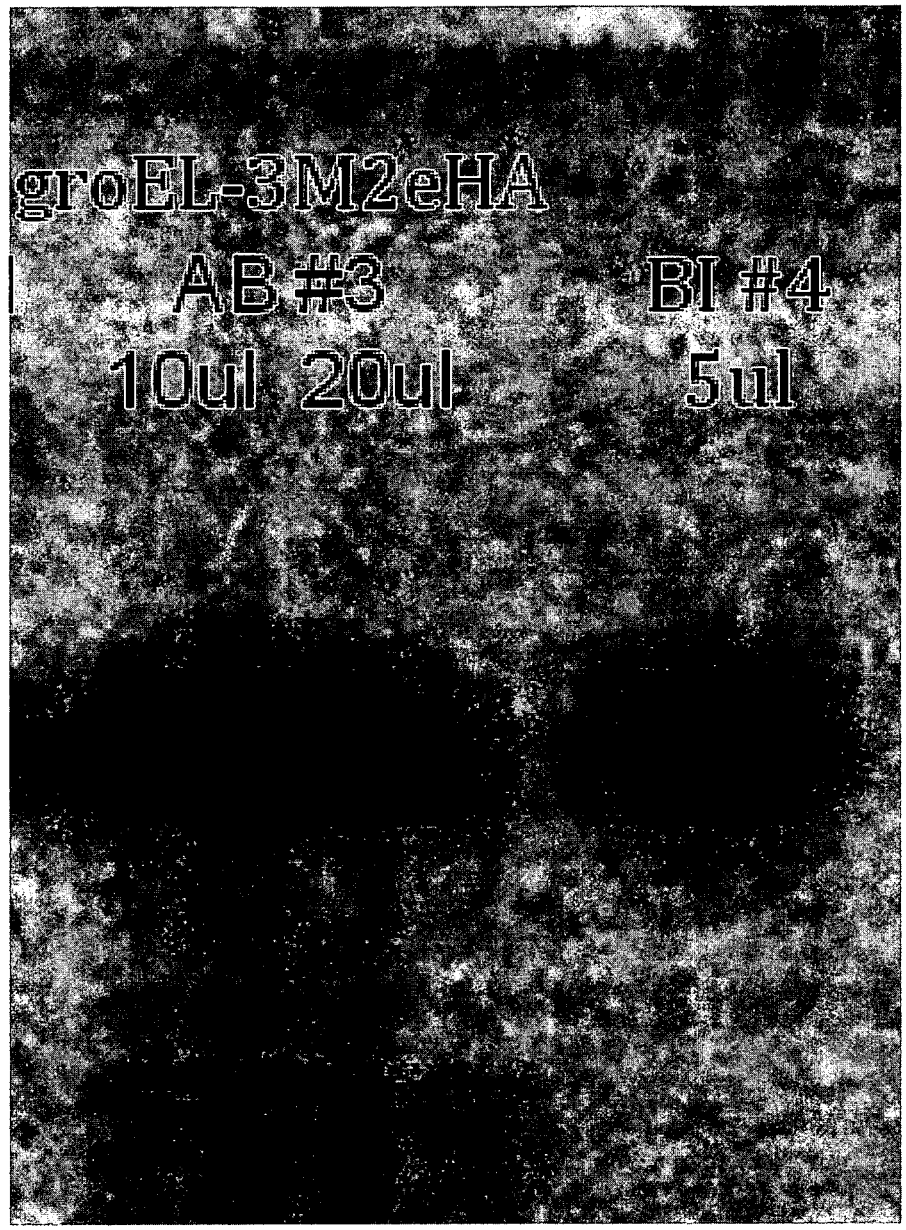
FIG. 20: Western analysis of recombinant bacteria. Western blot of recombinant clones: clone AB#3 expressing the groEL-3M2eHA fusion between ureA and ureB (pAB plasmid), and clone BI#4 expressing the groEL-3M2eHA fusion after ureB (pBI plasmid).
Figure 21:
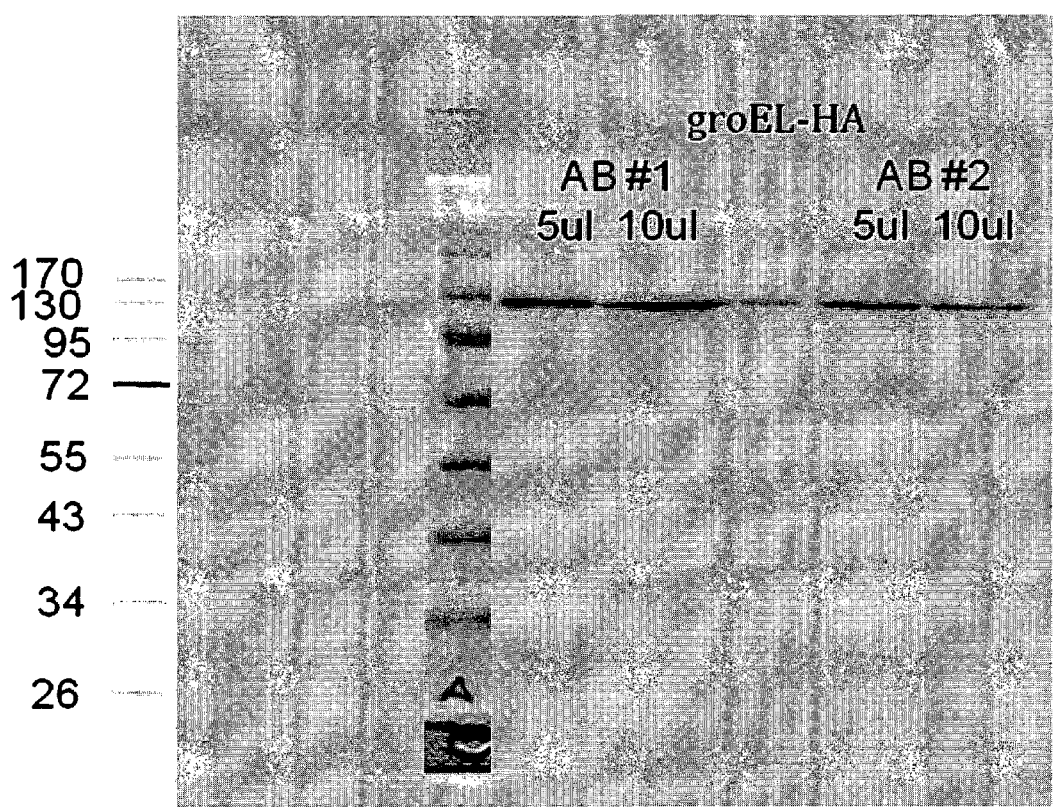
FIG. 21: Western blot of recombinant clones expressing the groEL-HA fusion between ureA and ureB (pAB plasmid), clone AB#1 and AB#2 respectively.
Figure 22:
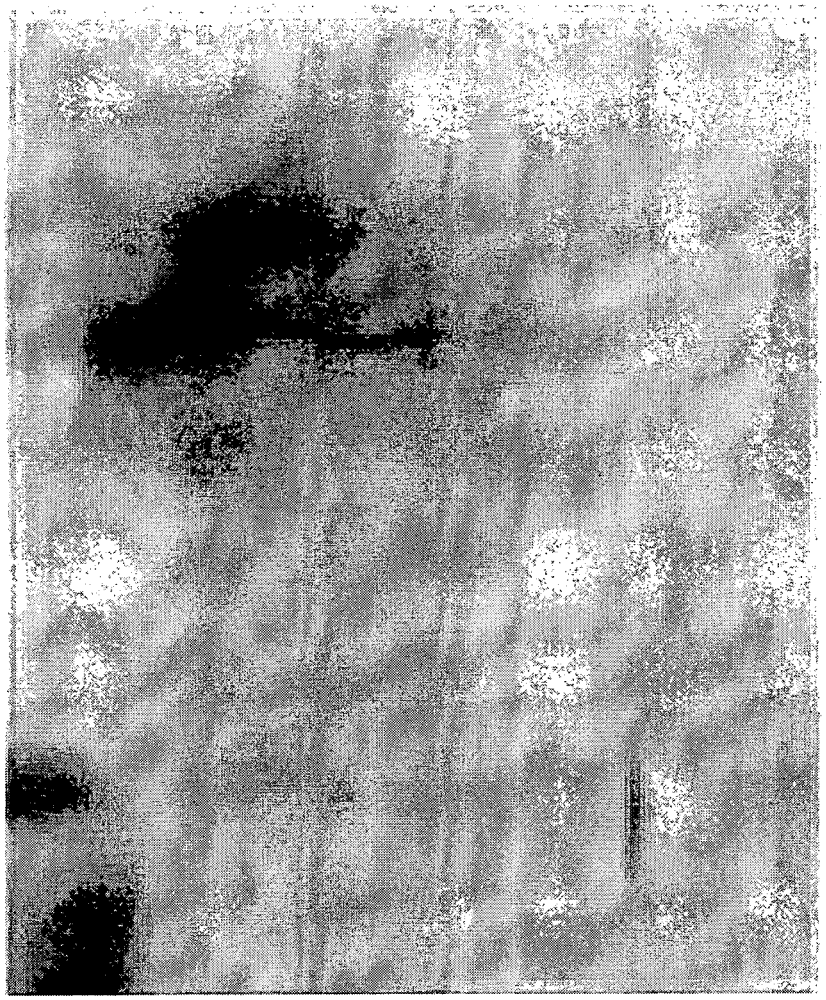
FIG. 22: Western blot of recombinant clones expressing the groEL-HA fusion between ureA and ureB (pOND634 plasmid), lane 1 and 2. Lane 3 corresponds to the negative control, recipient strains. Antibody: anti-haemagglutinin.

Fusions of GroEL to the haemagglutinin (HA) head of the Influenza virus (the main protective antigen for the Influenza vaccine) or the multiple epitope tag 3M2-HA were constructed for expression in *H. Pylori*. The fusions were inserted between the urease A and B subunits using pAB and pOND634 plasmids or after the urease B using pBI for the construction of a synthetic operon and expression from the strong urease promoter. FIGS. 20 to 22 show the expression of groEL-3M2eHA fusion (SEQ ID NO:21) in *H. pylori*, groEL-HA (SEQ ID NO:22) and groEL-HA fusion between ureA and ureB (pOND634 plasmid).

Example 15

Immune Responses

As described in Example 11, the synthetic operon of the present invention was exploited as a means to deliver bacterial antigens to the host. The strategy was developed to insert antigens, such as Cholera toxin subunit B and Pertussis S1 protein, between the urease A and B genes.

Figure 23:
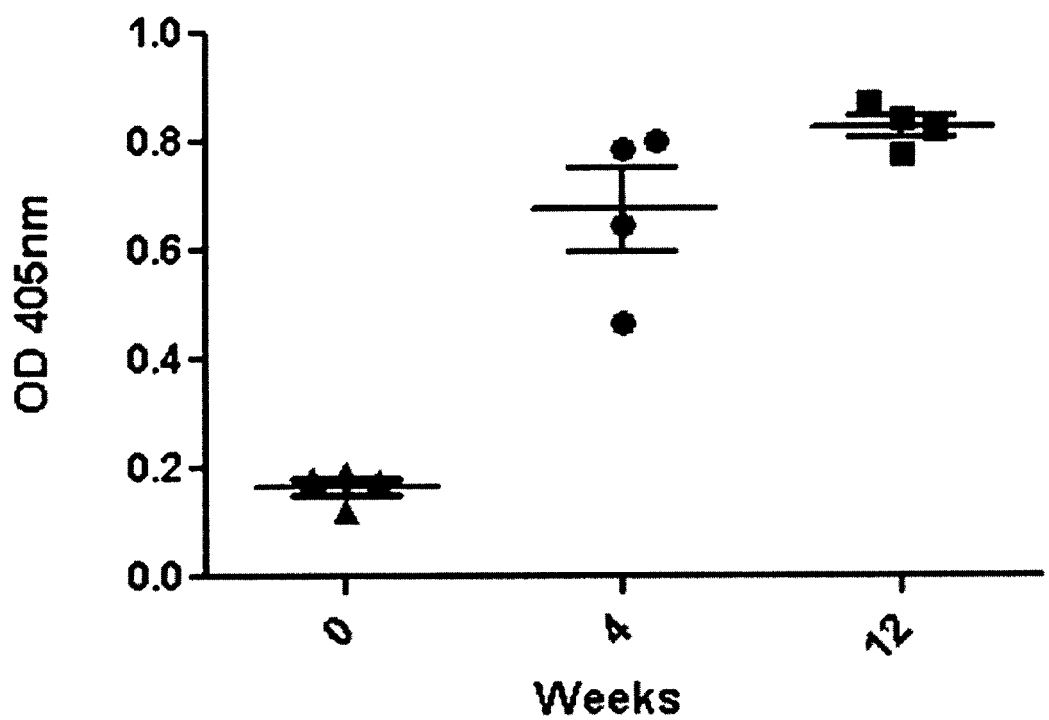
FIG. 23: Pertussis toxoid—specific antibodies in mice immunised with *H. pylori* expressing Pertussis S1 protein at the ureAB locus. Mice (n=5) were orally challenged with $10^9$ CFU bacteria and serum collected at 4 and 12 weeks post challenge. Specific antibody titres were measured by standard ELISA and expressed as the individual and average $OD_{405}$ value.

In vivo studies demonstrated that this approach was successful. High levels of Pertussis-specific IgG antibody titres were generated in all mice 4 weeks after challenge with the recombinant strain expressing the secreted Pertussis toxoid as shown in FIG. 23. Antibody titres persisted for up to 20 weeks post infection (data not shown).

Figure 24:
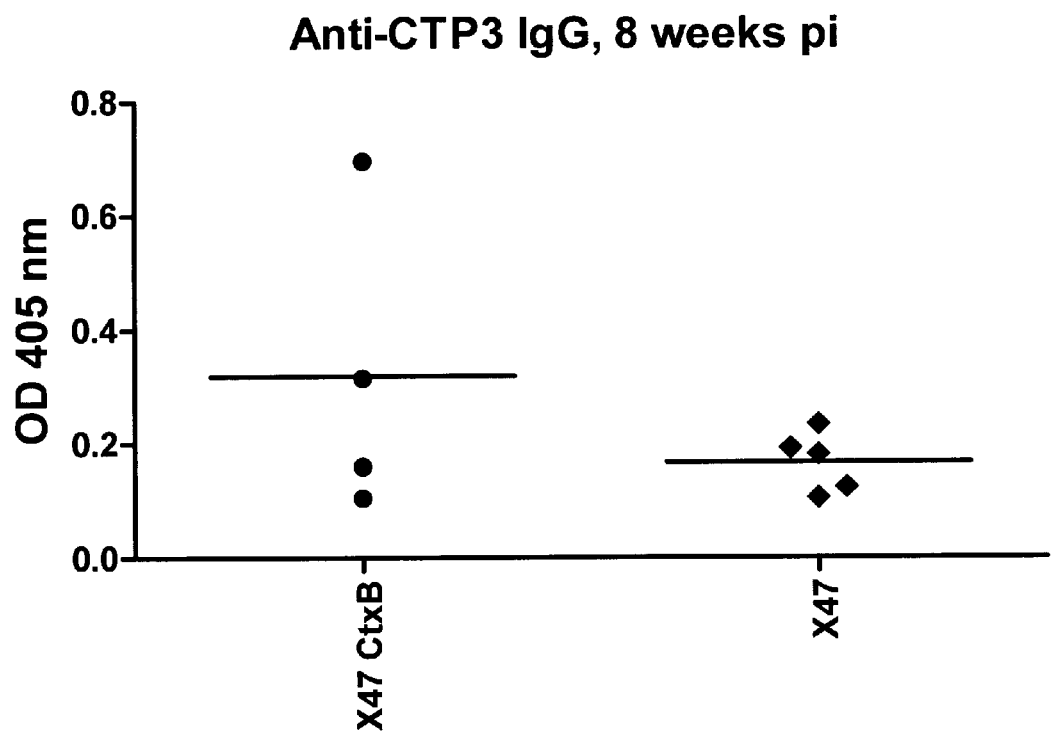
FIG. 24: Cholera—specific antibodies in mice immunised with *H. pylori* expressing CTxB at the ureAB locus. Mice (n=5) were orally challenged with $10^9$ CFU bacteria and serum was collected at 8 weeks after challenge. Specific IgG antibody titres were measured by standard ELISA and expressed as the $OD_{405}$ value. Results of individual mice and group averages are shown.

FIG. 24 shows expression of a second bacterial protein, ctxB by the Type II secretion system. Cholera-specific IgG responses were induced in approximately 50% of mice challenged with HPPT ureAB-CTxB.

Taken together, these results clearly indicate that the synthetic operon is a successful mode of delivery for large foreign antigens.

Figure 25:
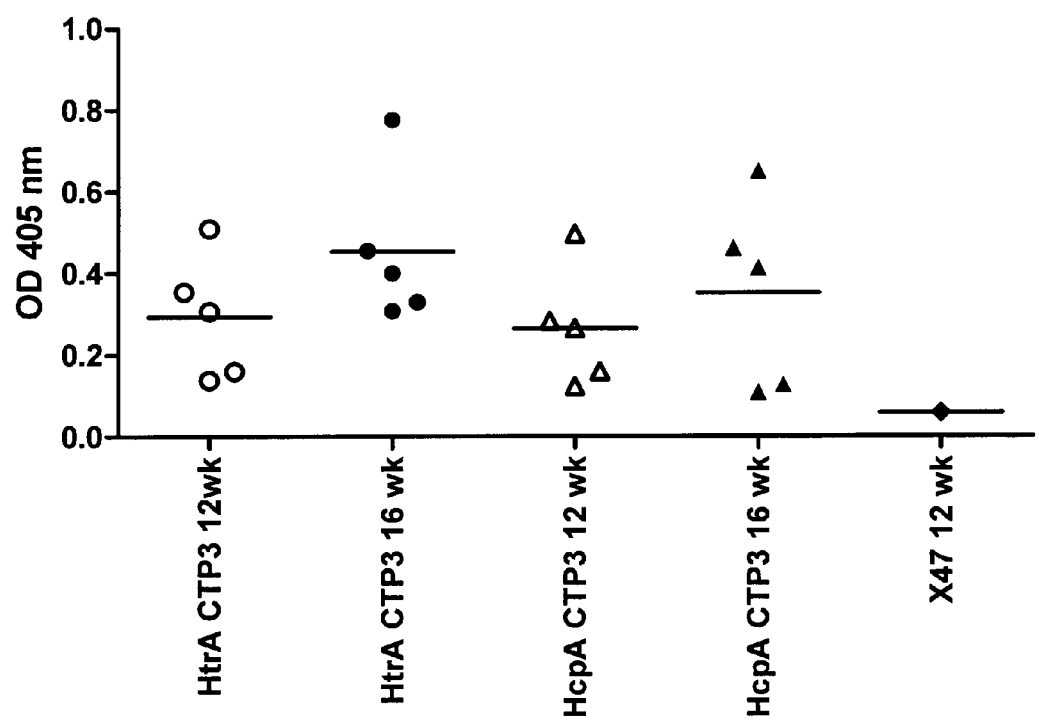
FIG. 25: Cholera toxin (CTP3)—specific antibodies in mice immunised with *H. pylori* expressing HtrA-CTP3 or HcpA-CTP3 at the ureA locus. Mice (n=5) were orally challenged with $10^9$ CFU bacteria and serum collected at 12 and 16 weeks post challenge. Specific antibody titres were measured by standard ELISA and expressed as the individual and average $OD_{405}$ value.

Delivery of the Cholera toxin CTP3 epitope was also evaluated using the *H. pylori* proteins HtrA and HcpA as carriers. In vivo studies demonstrated induction of specific IgG antibody titres in mice challenged with HPPT strains expressing CTP3 fused to HrtA or HcpA, 12 and 16 weeks after challenge as shown in FIG. 25. Although slightly weaker in general, antibody responses with the HtrA-CTP3 strain appeared to be stronger than those observed with the HcpA-CTP3 strain.

Example 16

Figure 26:
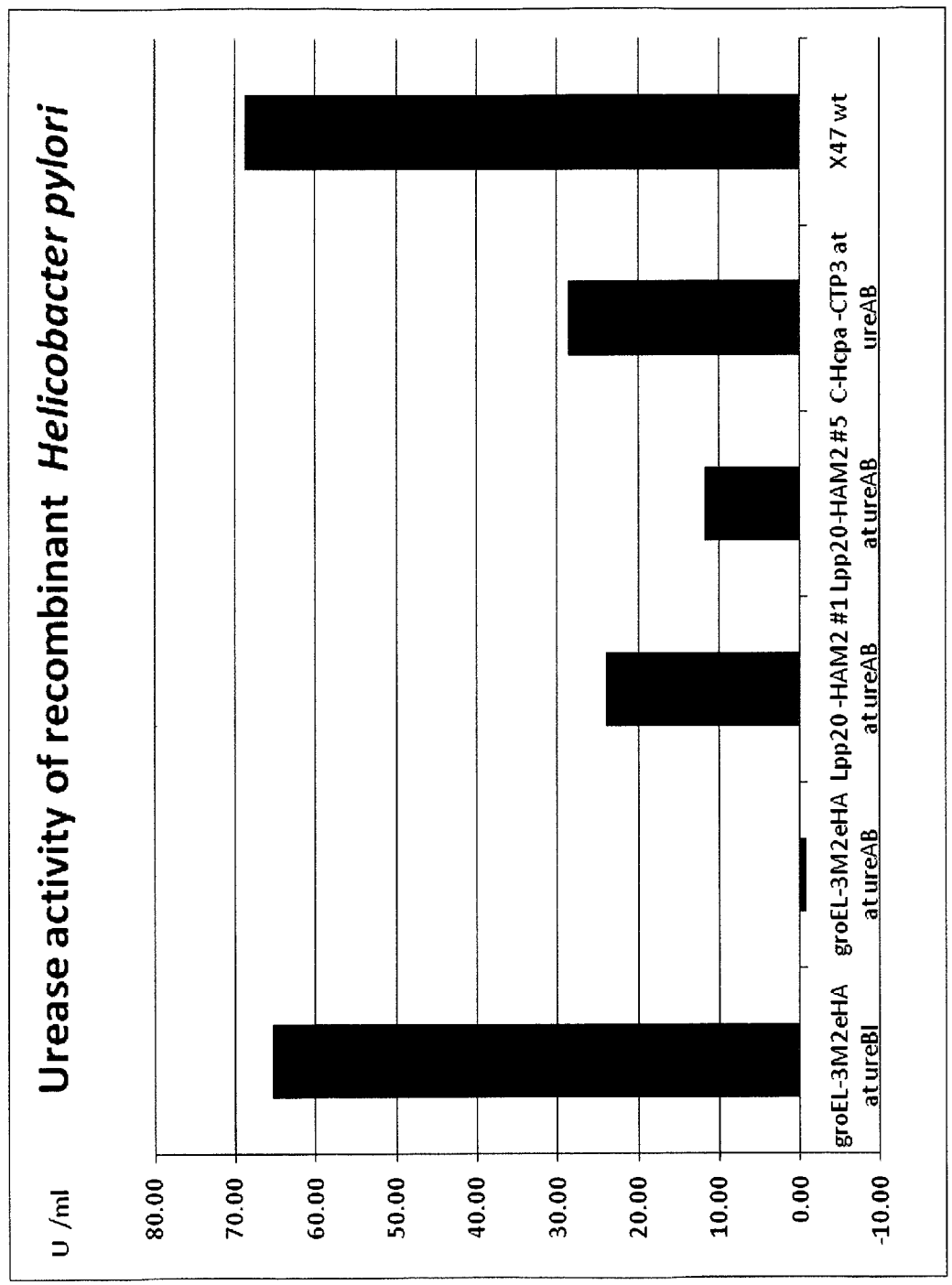
FIG. 26: Urease activity of recombinant *H. pylori* harbouring a urease synthetic operon. Ability of permeabilised *Helicobacter pylori* strains to neutralize acid after in the presence of urea. Urease activities of wild-type and recombinant bacteria cell suspensions were measured by a change in pH as indicated by a change in the colour of phenol red and express in U/ml.
Figure 27:
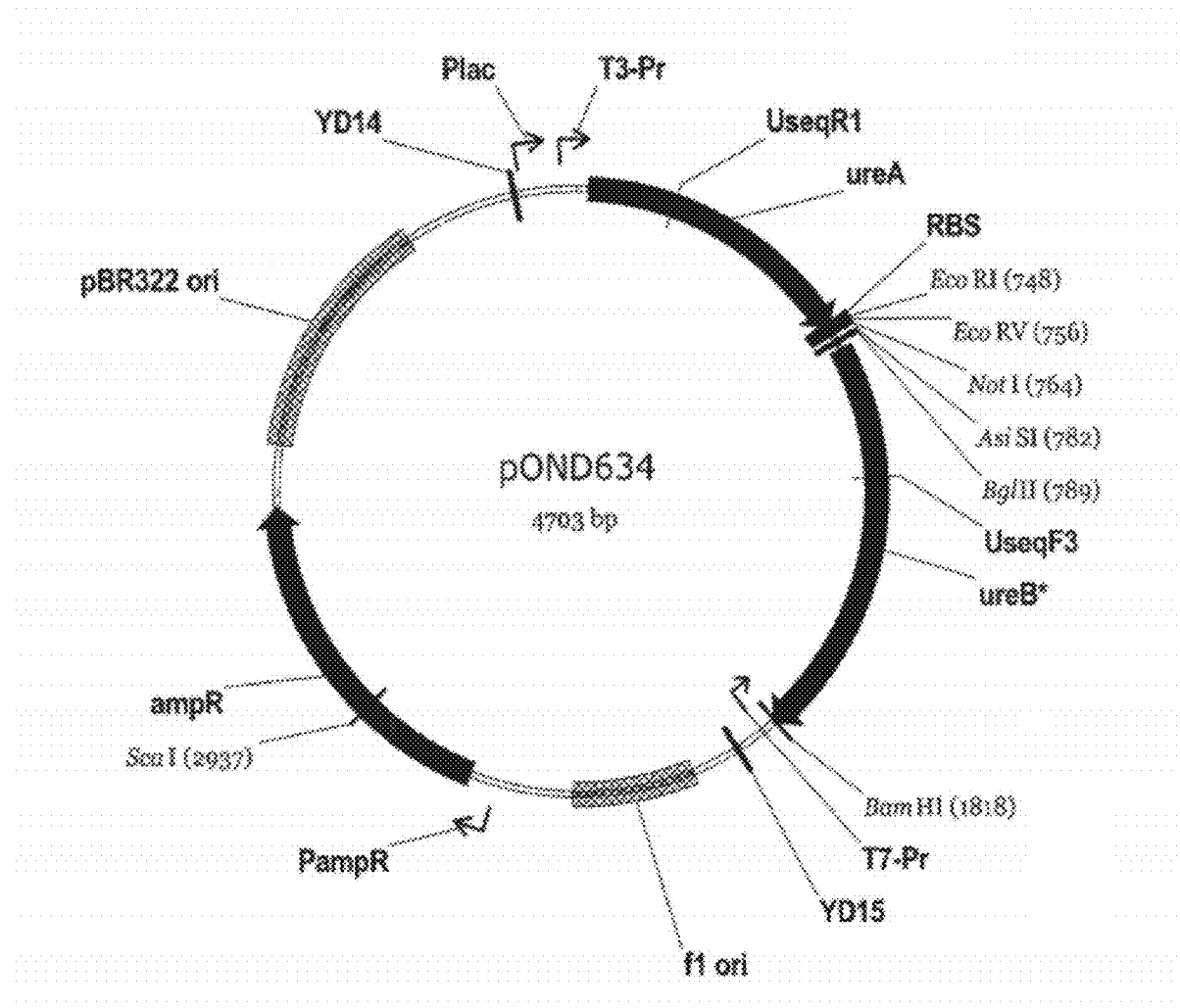
FIG. 27: Schematic of plasmid vector pOND634.

Urease Activity of Recombinant *H. Pylori* Harbouring the Urease Synthetic Operon The urease activity of recombinant *Helicobacter pylori* constructed with the pAB and pBI plasmids was found to be variable. Whereas, insertion of the fusions after the urease B always gave rise to clones with a similar urease activity to the wild type (FIG. 26 and data not shown), insertion of the fusions between A and B led to a variable and weaker urease activity compared to wild type. This result suggests that either co-transcription or the translation efficiency of the two urease subunits A and B is affected when the gene of interest insertion (sometimes called 'hitchhiker') is located between A and B, but not after B. Thus, investigation of translation signals of the urease operon was studied in more detail.

Example 17

Construction of a Plasmid that Enables the Insertion of Fusions Between the Urea and ureB Genes of *Helicobacter pylori* without Affecting the Urease Activity and Mouse Colonisation The ureA and ureB genes are highly expressed by *Helicobacter pylori* cells. Both genes belong to the same operon controlled by a strong promoter. Additionally, a strong Ribosome Binding Site (RBS) is located six nucleotides upstream of the initiation codon of each gene. The ureB RBS is located at the end of the ureA ORF and, as a result, the insertion of DNA cassettes between ureA and ureB in the pAB plasmid previously constructed separates ureB from its RBS. This may result in a lower urease activity and may be the explanation of the colonisation defect observed for some recombinant *Helicobacter pylori* strains harbouring a construct at the ureAB locus. This plasmid was constructed to restore the ureB RBS upon insertion of DNA constructs. In addition it contains an EcoRV site (produces blunt-ended DNA) for easy cloning of DNA constructs with blunt ends including those obtained by PCR.

To construct the plasmid, the ureA region was amplified from pOND549 using the primers:

YD14
(SEQ ID NO: 23)
ctcattaggcaccccaggcttta
and

YD-Ok054
(SEQ ID NO: 24)
TTAGCGATCGCCCATGTAGCGGCCGCATCGATATCgaattcttactcct
taattgttttta, and the ureB region amplified using the primers YD15
(SEQ ID NO: 25)
gatgtgctgcaaggcgattaagttg
and YD-Ok055
(SEQ ID NO: 26)
TACATGGGCGATCGCTAAAGATCTAGGAGTAACTAatgaaaaagattag
cagaaaagaatat.

YD-Ok054 and YD-Ok055 possess extensions that are partly overlapping. The two PCR products were fused and amplified using the primers M13F new:

(SEQ ID NO: 27)
CAGTCACGACGTTGTAAAACGACGG that binds downstream of YD15 and M13R new:

(SEQ ID NO: 28)
CAGGAAACAGCTATGACCATGATTACGC that hybridizes downstream of YD14. The resulting 1992 bp product was digested with KpnI and SacI and then treated with T4 DNA polymerase. The blunt-ended resulting product was ligated with the T4-DNA-Polymerase-treated 2856 bp KpnI-SacI fragment from pOND547. The ligation produced two orientations, pOND634 corresponds to the one in which ureA is placed under the control of the $P_{lac}$ promoter. The relevant regions of pOND634 were verified by sequencing (SEQ ID NO:29).

Example 18

Colonisation of Mouse Stomach

The ability of recombinant strains harbouring the urease synthetic operon to colonise mice depends on the ability to maintain a sufficient level of urease. It was found that insertion after the urease B subunit using pBI plasmid did not interfere with colonisation (Table 3 and data not shown). It was observed that colonisation varied significantly depending on the nature of the hitchhiker gene for insertions between the urease A and B using pAB plasmid (Table 3).

The use of the plasmid pOND634 restoring the ribosome binding site upon insertion of the hitchhiker gene between the urease subunits A and B allowed for robust colonisation of the recombinant strain as exemplified by the groeL-HA gene insertion (Table 3). Similar levels of urease activity compared to wild type were achieved when using the pOND634 plasmid (data not shown). In contrast, using pAB plasmid to insert the groeL-HA gene led to a complete lack of colonisation (Table 3) and very weak urease activity (data not shown).

TABLE 3

| Insert | Plasmid/Locus | Mouse colonisation |
|---|---|---|
| S1 fragment of the *Pertussis* toxin | pAB | 1/3 infected |
| CtxB | pAB | 3/3 infected |
| CTP3-htrA | pAB | 1/3 infected |
| Lpp20-HAM2 | pAB | 2/3 infected |
| HcpA-3M2-HA | pAB | 2/3 infected |
| HcpA-CTP3 | pAB | 0/3 infected |
| PrsA-3M2HA | pAB | 2/3 infected |
| groEL-3M2-HA | pBI | 3/3 infected |
| groEL-3M2-HA | pAB | 0/3 infected |
| groEL-HA | pAB | 0/3 infected |
| groEL-HA | pOND634 | 3/3 infected |

The invention claimed is:

1. A method of expressing a gene of interest in *H. pylori*, the method comprising:
   a) integrating an operon into chromosomal DNA of a *H. pylori* bacterium, wherein the operon comprises a promoter operably-linked to at least two genes, wherein at least one gene is a gene of interest and at least one gene is a *H. pylori* urease gene, wherein the gene of interest is positioned within the operon between a urease A (ureA) gene and a urease B (ureB) gene or after a ureB gene, such that transcription of the gene of interest is linked to transcription of subunits A and B of a urease complex, and wherein the promoter is arranged such that a polycistronic mRNA comprising both the gene of interest and the *H. pylori* urease gene is transcribed; and
   b) culturing said bacterium to express the gene of interest.

2. The method of claim 1, wherein the *H. pylori* is a strain of *H. pylori* selected from National Measurement Institute accession numbers V09/009,101 (OND737); V09/009,102 (OND738); V09/009,103 (OND739); V09/009,104 (OND740); V10/014,059 (OND248) and V10/014,060 (OND256).

3. The method of claim 1, wherein the operon is contained in an expression vector.

4. The method of claim 1, wherein the operon comprises a signal peptide.

5. The method of claim 4, wherein the signal peptide is a secretory signal peptide.

6. The method of claim 4, wherein the signal peptide is a secretory signal peptide of a *H. pylori* vacA protein.

7. The method of claim 4, wherein the signal peptide is at the N-terminus of the operon.

8. The method of claim 1, wherein the operon is stably integrated into a chromosome of *H. pylori*.

9. The method of claim 1, wherein the *H. pylori* urease gene is essential to colonization and survival in vivo of *H. pylori*.

* * * * *

SEQUENCE LISTING

<160> NUMBER OF SEQ ID NOS: 29

<210> SEQ ID NO 1
<211> LENGTH: 4973
<212> TYPE: DNA
<213> ORGANISM: Artificial Sequence
<220> FEATURE:
<223> OTHER INFORMATION: Plasmid DNA

<400> SEQUENCE: 1
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc    120
tcgccacgtt cgccggcttt ccccgtcaag ctctaaatcg ggggctccct ttagggttcc    180
gatttagtgc tttacggcac ctcgacccca aaaaacttga ttagggtgat ggttcacgta    240

```
gtgggccatc gccctgatag acggtttttc gcccttttgac gttggagtcc acgttcttta    300
atagtggact cttgttccaa actggaacaa cactcaaccc tatctcggtc tattcttttg    360
atttataagg gattttgccg attttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgggtaccgg    660
gccccccctc gatcgacggt atcgataagc ttagcactac cttgacatgg tagtggccgc    720
tggttcaagt ccagtcgtgg ccaccattat cactccaatt ttaattctca ttttttttgcg    780 agttttttgat ctttataaat tctaaagggg tattaaacgc acttctaata acgatttat    840 agcgcttcaa agatataaca ctaattcatt ttaaataata attagttaat gaacgcttct    900
gttaatctta gtaaatcaaa acattgctac aattacatcc aaccttgatt tcgttatgtc    960
ttcaaggaaa aacactttaa gaataggaga ataagatgaa actcaccccca aaagagttag   1020 acaagttgat gctccactat gctggagaat tggctaaaaa acgcaaagaa aaaggcatta   1080
agcttaacta tgtagaagcg gtagctttga ttagtgccca tattatggaa gaagcgagag   1140
ctggtaaaaa gactgcggct gaattgatgc aagaagggcg cactctttta aaaccggatg   1200
atgtgatgga tggcgtggca agcatgatcc atgaagtggg tattgaagcg atgtttcctg   1260
atgggacaaa actcgtaacc gtgcataccc ctattgaggc caatggtaaa ttagttcctg   1320
gtgagttgtt cttaaaaaat gaagacatca ctatcaacga aggcaaaaaa gccgttagcg   1380
tgaaagttaa aaatgttggc gacagaccgg ttcaaatcgg ctcacacttc catttctttg   1440
aagtgaatag atgcttagac tttgacagag aaaaaacttt cggtaaacgc ttagacattg   1500
cgagcgggac agcggtaagg tttgagcctg gcgaagaaaa atccgtagaa ttgattgaca   1560
ttggcggtaa cagaagaatc tttggattta acgcgttggt tgataggcaa gcagacaacg   1620
aaagcaaaaa aattgcttta cacagagcta agagcgtgg ttttcatggc gctaaaagcg   1680
atgacaacta tgtaaaaaca attaaggagt aagaattcag atctgaaatg aaaaagatta   1740
gcagaaaaga atatgtttct atgtatggcc ctactacagg cgataaagtg agattgggcg   1800
atacagactt gatcgctgaa gtagaacatg actacaccat ttatggcgaa gagcttaaat   1860
tcggtggcgg taaaaccctg agagaaggca tgagccaatc caacaaccct agcaaagaag   1920
aattggatct aatcatcact aacgctttaa tcgtggatta caccggtatt tataaagcgg   1980
atattggtat taaagatggc aaaatcgctg gcattggtaa aggcggtaac aaagacatgc   2040
aagatggcgt taaaaacaat cttagcgtag gtcctgctac tgaagcctta gccggtgaag   2100
gtttgatcgt aactgctggt ggtattgaca cacacatcca cttcatttca ccccaacaaa   2160
tccctacagc ttttgcaagc ggtgtaacaa ccatgattgg tggcggaact ggtcctgctg   2220
atggcactaa tgcgactact atcactccag gcagaagaaa tttaaaatgg atgctcagag   2280
cggctgaaga atattctatg aacttaggtt tcttggctaa aggtaacgct tctaacgacg   2340
cgagcttagc cgatcaaatt gaagctggtg cgattggctt taaatccac gaagactggg   2400 gcaccactcc ttctgcaatc aatcatgcgt tagatgttgc agacaaatac gatgtgcaag   2460
tcgctatcca cacagacact ttgaatgaag ccggttgcgt ggaagacact atggcagcta   2520
ttgccggacg cactatgcac acttttccaca ctgaaggtgc tggcggcgga cacgctcctg   2580
atattattaa agtagctggt gaacacaaca ttcttcccgc ttccactaac cccactatcc   2640
```

```
ctttcactgt gaatacagaa gcagaacaca tggacatgct tatggtgtgc caccacttgg    2700
ataaaagcat taaagaagat gttcagttcg ctgattcaag gatcctctag agcggccgcc    2760
accgcggtgg agctccagct tttgttccct ttagtgaggg ttaatttcga gcttggcgta    2820
atcatggtca tagctgtttc ctgtgtgaaa ttgttatccg ctcacaattc cacacaacat    2880
acgagccgga agcataaagt gtaaagcctg gggtgcctaa tgagtgagct aactcacatt    2940
aattgcgttg cgctcactgc ccgctttcca gtcgggaaac ctgtcgtgcc agctgcatta    3000
atgaatcggc caacgcgcgg ggagaggcgg tttgcgtatt gggcgctctt ccgcttcctc    3060
gctcactgac tcgctgcgct cggtcgttcg gctgcggcga gcggtatcag ctcactcaaa    3120
ggcggtaata cggttatcca cagaatcagg ggataacgca ggaaagaaca tgtgagcaaa    3180
aggccagcaa aaggccagga accgtaaaaa ggccgcgttg ctggcgtttt tccataggct    3240
ccgcccccct gacgagcatc acaaaaatcg acgctcaagt cagaggtggc gaaacccgac    3300
aggactataa agataccagg cgtttccccc tggaagctcc ctcgtgcgct ctcctgttcc    3360
gaccctgccg cttaccggat acctgtccgc ctttctccct tcgggaagcg tggcgctttc    3420
tcatagctca cgctgtaggt atctcagttc ggtgtaggtc gttcgctcca agctgggctg    3480
tgtgcacgaa ccccccgttc agcccgaccg ctgcgcctta tccggtaact atcgtcttga    3540
gtccaacccg gtaagacacg acttatcgcc actggcagca gccactggta acaggattag    3600
cagagcgagg tatgtaggcg gtgctacaga gttcttgaag tggtggccta actacggcta    3660
cactagaagg acagtatttg gtatctgcgc tctgctgaag ccagttacct tcggaaaaag    3720
agttggtagc tcttgatccg gcaaacaaac caccgctggt agcggtggtt tttttgtttg    3780
caagcagcag attacgcgca gaaaaaaagg atctcaagaa gatcctttga tcttttctac    3840
ggggtctgac gctcagtgga acgaaaactc acgttaaggg attttggtca tgagattatc    3900
aaaaaggatc ttcacctaga tccttttaaa ttaaaaatga agttttaaat caatctaaag    3960
tatatatgag taaacttggt ctgacagtta ccaatgctta atcagtgagg cacctatctc    4020
agcgatctgt ctatttcgtt catccatagt tgcctgactc cccgtcgtgt agataactac    4080
gatacgggag ggcttaccat ctggccccag tgctgcaatg ataccgcgag acccacgctc    4140
accggctcca gatttatcag caataaacca gccagccgga agggccgagc gcagaagtgg    4200
tcctgcaact ttatccgcct ccatccagtc tattaattgt tgccgggaag ctagagtaag    4260
tagttcgcca gttaatagtt tgcgcaacgt tgttgccatt gctacaggca tcgtggtgtc    4320
acgctcgtcg tttggtatgg cttcattcag ctccggttcc caacgatcaa ggcgagttac    4380
atgatccccc atgttgtgca aaaaagcggt tagctccttc ggtcctccga tcgttgtcag    4440
aagtaagttg gccgcagtgt tatcactcat ggttatggca gcactgcata attctcttac    4500
tgtcatgcca tccgtaagat gcttttctgt gactggtgag tactcaacca agtcattctg    4560
agaatagtgt atgcggcgac cgagttgctc ttgcccggcg tcaatacggg ataataccgc    4620
gccacatagc agaactttaa aagtgctcat cattggaaaa cgttcttcgg ggcgaaaact    4680
ctcaaggatc ttaccgctgt tgagatccag ttcgatgtaa cccactcgtg cacccaactg    4740
atcttcagca tcttttactt tcaccagcgt ttctgggtga gcaaaaacag gaaggcaaaa    4800
tgccgcaaaa aagggaataa gggcgacacg gaaatgttga atactcatac tcttcctttt    4860
tcaatattat tgaagcattt atcagggtta ttgtctcatg agcggataca tatttgaatg    4920
tatttagaaa aataaacaaa tagggggttcc gcgcacattt ccccgaaaag tgc          4973
```

<210> SEQ ID NO 2
<211> LENGTH: 4977
<212> TYPE: DNA
<213> ORGANISM: Artificial Sequence
<220> FEATURE:
<223> OTHER INFORMATION: Plasmid

<400> SEQUENCE: 2

| | | | | | | |
|---|---|---|---|---|---|---|
| cacctgacgc | gccctgtagc | ggcgcattaa | gcgcggcggg | tgtggtggtt | acgcgcagcg | 60 |
| tgaccgctac | acttgccagc | gccctagcgc | ccgctccttt | cgctttcttc | ccttcctttc | 120 |
| tcgccacgtt | cgccggcttt | ccccgtcaag | ctctaaatcg | gggctccct | ttagggttcc | 180 |
| gatttagtgc | tttacggcac | ctcgacccca | aaaaacttga | ttagggtgat | ggttcacgta | 240 |
| gtgggccatc | gccctgatag | acggttttc | gccctttgac | gttggagtcc | acgttcttta | 300 |
| atagtggact | cttgttccaa | actggaacaa | cactcaaccc | tatctcggtc | tattcttttg | 360 |
| atttataagg | gattttgccg | atttcggcct | attggttaaa | aaatgagctg | atttaacaaa | 420 |
| aatttaacgc | gaattttaac | aaaatattaa | cgcttacaat | ttccattcgc | cattcaggct | 480 |
| gcgcaactgt | tgggaagggc | gatcggtgcg | ggcctcttcg | ctattacgcc | agctggcgaa | 540 |
| agggggatgt | gctgcaaggc | gattaagttg | ggtaacgcca | gggttttccc | agtcacgacg | 600 |
| ttgtaaaacg | acggccagtg | aattgtaata | cgactcacta | tagggcgaat | tgggtaccgg | 660 |
| gccccccctc | gatcgacggt | atcgataagc | ttcatgcgtt | agatgttgca | gacaaatacg | 720 |
| atgtgcaagt | cgctatccac | acagacactt | tgaatgaagc | cggttgcgtg | aagacacta | 780 |
| tggcagctat | tgccggacgc | actatgcaca | ctttccacac | tgaaggtgct | ggcggcggac | 840 |
| acgctcctga | tattattaaa | gtagctggtg | aacacaacat | tcttcccgct | tccactaacc | 900 |
| ccactatccc | tttcactgtg | aatacagaag | cagaacacat | ggacatgctt | atggtgtgcc | 960 |
| accacttgga | taaaagcatt | aaagaagatg | ttcagttcgc | tgattcaagg | atccgccctc | 1020 |
| aaaccattgc | ggctgaagac | actttgcatg | acatggggat | tttctcaatc | accagctctg | 1080 |
| actctcaagc | tatgggtcgt | gtgggtgaag | ttatcactag | aacttggcaa | acagctgaca | 1140 |
| aaaacaaaaa | agaatttggc | cgcttgaaag | aagaaaaagg | cgataacgac | aacttcagga | 1200 |
| tcaaacgcta | cttgtctaaa | tacaccatta | acccagcgat | cgctcatggg | attagcgagt | 1260 |
| atgtaggttc | tgtagaagtg | ggcaaagtgg | ctgacttggt | attgtggagt | cccgcattct | 1320 |
| ttggcgtaaa | acccaacatg | atcatcaaag | gcgggttcat | tgcgttgagt | caaatgggtg | 1380 |
| acgcgaacgc | ttctatccct | accccacaac | cagtttatta | cagagaaatg | ttcgctcatc | 1440 |
| atggtaaagc | caaatacgat | gcaaacatca | cttttgtgtc | tcaagcggct | tatgacaaag | 1500 |
| gcattaaaga | agaattaggg | cttgaaagac | aagtgttgcc | ggtaaaaaat | tgcagaaaca | 1560 |
| tcactaaaaa | agacatgcaa | ttcaacgaca | ctaccgctca | cattgaagtc | aatcctgaaa | 1620 |
| cttaccatgt | gttcgtggat | ggcaaagaag | taacttctaa | accagccaat | aaagtgagct | 1680 |
| tggcgcaact | ctttagcatt | ttctaggatt | ttttaggagc | aacgctcctt | aaatccttag | 1740 |
| tttttagctc | tctgattttt | tgtttatcaa | aaaattgggg | gcttttttg | tgaattcaga | 1800 |
| tctttttatt | ttttgtcaat | ttactatttt | tctttatgat | tagctcaagc | aacaaaagtt | 1860 |
| attcgtaagg | tgcgtttgtt | gtaaaaattt | ttgtttggaa | ggaaaaggca | atgctaggac | 1920 |
| ttgtattgtt | atatgtttggg | attgttttaa | tcagcaatgg | gatttgcggg | ttaaccaaag | 1980 |
| tcgatcctaa | aagcactgcg | gtgatgaact | tttttgtggg | cggactttcc | attatttgta | 2040 |
| atatagttgt | catcacttat | tctgcactcc | accctacagc | ccctgtagaa | ggtgctgaag | 2100 |
| atattgctca | agtatcgcac | catttgacta | gtttctatgg | accagcgact | gggttattgt | 2160 |

```
ttggtttcac ctacttgtat gcggctatca accacacttt tggtttggat tggaggccct    2220
actcttggta tagcttattc gtagcgatca acacgattcc tgctgcgatt ttatcccact    2280
atagcgatat gcttgatgac cacaaagtgt taggcatcac tgaaggcgat tggtgggcga    2340
tcatttggtt ggcttggggt gttttgtggc ttaccgcttt cattgaaaac atcttgaaaa    2400
tccctttagg gaaattcact ccatggcttg ctatcattga gggtatttta accgcttgga    2460
tccctgcttg gttgctcttt atccaacact gggtgtgaga tgatcataga gcgtttagtt    2520
ggcaatctaa gggatttaaa ccccttggat ttcagcgtgg atcatgtgga tttggaatgg    2580
tttgaaacga ggaaaaaaat cgctcgtttt aaaaccaggc aaggcaaaga catagccata    2640
cgccttaaag acgctcccaa gttgggctc tctcaagggg atattttatt taaagaagag    2700
aaggaaatta tcgccgttaa tatcttggat tctgaagtca ttcacatcct ctagagcggc    2760
cgccaccgcg gtggagctcc agcttttgtt ccctttagtg agggttaatt tcgagcttgg    2820
cgtaatcatg gtcatagctg tttcctgtgt gaaattgtta tccgctcaca attccacaca    2880
acatacgagc cggaagcata aagtgtaaag cctggggtgc ctaatgagtg agctaactca    2940
cattaattgc gttgcgctca ctgcccgctt tccagtcggg aaacctgtcg tgccagctgc    3000
attaatgaat cggccaacgc gcggggagag gcggtttgcg tattgggcgc tcttccgctt    3060
cctcgctcac tgactcgctg cgctcggtcg ttcggctgcg gcgagcggta tcagctcact    3120
caaaggcggt aatacggtta tccacagaat caggggataa cgcaggaaag aacatgtgag    3180
caaaaggcca gcaaaaggcc aggaaccgta aaaaggccgc gttgctggcg ttttccata    3240
ggctccgccc ccctgacgag catcacaaaa atcgacgctc aagtcagagg tggcgaaacc    3300
cgacaggact ataaagatac caggcgtttc ccctggaag ctccctcgtg cgctctcctg    3360
ttccgaccct gccgcttacc ggatacctgt ccgcctttct cccttcggga agcgtggcgc    3420
tttctcatag ctcacgctgt aggtatctca gttcggtgta ggtcgttcgc tccaagctgg    3480
gctgtgtgca cgaaccccc gttcagcccg accgctgcgc cttatccggt aactatcgtc    3540
ttgagtccaa cccggtaaga cacgacttat cgccactggc agcagccact ggtaacagga    3600
ttagcagagc gaggtatgta ggcggtgcta cagagttctt gaagtggtgg cctaactacg    3660
gctacactag aaggacagta tttggtatct gcgctctgct gaagccagtt accttcggaa    3720
aaagagttgg tagctcttga tccggcaaac aaaccaccgc tggtagcggt ggtttttttg    3780
tttgcaagca gcagattacg cgcagaaaaa aaggatctca agaagatcct ttgatctttt    3840
ctacggggtc tgacgctcag tggaacgaaa actcacgtta agggattttg gtcatgagat    3900
tatcaaaaag gatcttcacc tagatccttt taaattaaaa atgaagtttt aaatcaatct    3960
aaagtatata tgagtaaact tggtctgaca gttaccaatg cttaatcagt gaggcaccta    4020
tctcagcgat ctgtctattt cgttcatcca tagttgcctg actccccgtc gtgtagataa    4080
ctacgatacg ggagggctta ccatctggcc ccagtgctgc aatgataccg cgagacccac    4140
gctcaccggc tccagattta tcagcaataa accagccagc cggaagggcc gagcgcagaa    4200
gtggtcctgc aactttatcc gcctccatcc agtctattaa ttgttgccgg gaagctagag    4260
taagtagttc gccagttaat agtttgcgca acgttgttgc cattgctaca ggcatcgtgg    4320
tgtcacgctc gtcgtttggt atggcttcat tcagctccgg ttcccaacga tcaaggcgag    4380
ttacatgatc ccccatgttg tgcaaaaaag cggttagctc cttcggtcct ccgatcgttg    4440
tcagaagtaa gttggccgca gtgttatcac tcatggttat ggcagcactg cataattctc    4500
ttactgtcat gccatccgta agatgctttt ctgtgactgg tgagtactca accaagtcat    4560
```

-continued

```
tctgagaata gtgtatgcgg cgaccgagtt gctcttgccc ggcgtcaata cgggataata    4620
ccgcgccaca tagcagaact ttaaaagtgc tcatcattgg aaaacgttct tcggggcgaa    4680
aactctcaag gatcttaccg ctgttgagat ccagttcgat gtaacccact cgtgcaccca    4740
actgatcttc agcatctttt actttcacca gcgtttctgg gtgagcaaaa acaggaaggc    4800
aaaatgccgc aaaaaaggga ataagggcga cacggaaatg ttgaatactc atactcttcc    4860
tttttcaata ttattgaagc atttatcagg gttattgtct catgagcgga tacatatttg    4920
aatgtattta gaaaataaaa caaataggggg ttccgcgcac atttccccga aaagtgc      4977
```

<210> SEQ ID NO 3
<211> LENGTH: 4723
<212> TYPE: DNA
<213> ORGANISM: Artificial Sequence
<220> FEATURE:
<223> OTHER INFORMATION: Operon

<400> SEQUENCE: 3

```
atgaaaaaga ttagcagaaa agaatatgtt tctatgtatg ccctactac aggcgataaa     60 gtgagattgg gcgatacaga cttgatcgct gaagtagaac atgactacac catttatggc    120
gaagagctta aattcggtgg cggtaaaacc ctgagagaag gcatgagcca atccaacaac    180
cctagcaaag aagaattgga tctaatcatc actaacgctt taatcgtgga ttacaccggt    240
atttataaag cggatattgg tattaaagat ggcaaaatcg ctggcattgg taaaggcggt    300
aacaaagaca tgcaagatgg cgttaaaaac aatcttagcg taggtcctgc tactgaagcc    360
ttagccggtg aaggtttgat cgtaactgct ggtggtattg acacacacat ccacttcatt    420
tcaccccaac aaatccctac agcttttgca agcggtgtaa caaccatgat tggtggcgga    480
actggtcctg ctgatggcac taatgcgact actatcactc caggcagaag aaatttaaaa    540
tggatgctca gagcggctga agaatattct atgaacttag gtttcttggc taaaggtaac    600
gcttctaacg acgcgagctt agccgatcaa attgaagctg gtgcgattgg ctttaaaatc    660
cacgaagact ggggcaccac tccttctgca atcaatcatg cgttagatgt tgcagacaaa    720
tacgatgtgc aagtcgctat ccacacagac actttgaatg aagccggttg cgtggaagac    780
actatggcag ctattgccgg acgcactatg cacactttcc acactgaagg tgctggcggc    840
ggacacgctc ctgatattat aaagtagct ggtgaacaca acattcttcc cgcttccact    900
aaccccacta tcccttttcac tgtgaataca gaagcagaac acatggacat gcttatggtg    960
tgccaccact tggataaaag cattaaagaa gatgttcagt tcgctgattc aaggatccgc   1020
cctcaaacca ttgcggctga agacactttg catgacatgg ggattttctc aatcaccagc   1080
tctgactctc aagctatggg tcgtgtgggt gaagttatca ctagaacttg gcaaacagct   1140
gacaaaaaca aaagaatt tggccgcttg aagaagaaa aaggcgataa cgacaacttc    1200
aggatcaaac gctacttgtc taaatacacc attaacccag cgatcgctca tgggattagc   1260
gagtatgtag ttctgtaga agtgggcaaa gtggctgact tggtattgtg gagtcccgca   1320
ttctttggcg taaacccaa catgatcatc aaaggcgggt tcattgcgtt gagtcaaatg   1380
ggtgacgcga acgcttctat ccctacccca caaccagttt attacagaga atgttcgct   1440 catcatggta agccaaata cgatgcaaac atcacttttg tgtctcaagc ggcttatgac   1500
aaaggcatta agaagaatt agggcttgaa agacaagtgt tgccggtaaa aaattgcaga   1560
aacatcacta aaaagacat gcaattcaac gacactaccg ctcacattga agtcaatcct   1620
gaaacttacc atgtgttcgt ggatggcaaa gaagtaactt ctaaaccagc caataaagtg   1680
```

```
agcttggcgc aactctttag cattttctag gattttttag gagcaacgct ccttaaatcc    1740
ttagttttta gctctctgat tttttgttta tcaaaaaatt gggggctttt tttgtaagga    1800
tacaaaatgg caaagaaat caaattttca gatagcgcga gaaaccttttt atttgaaggc    1860
gtgagacaac tccatgacgc tgttaaagta accatgggc  caagaggcag gaacgtgttg    1920
atccaaaaaa gctatggcgc tccaagcatc actaaagatg gcgtgagcgt ggctaaagag    1980
attgaattaa gttgcccggt agctaacatg ggcgctcaac tcgttaaaga agtagcgagc    2040
aaaaccgctg atgctgccgg cgatggcacg accacagcga ccgtgctggc ttatagcatt    2100
tttaagaag gtttgaggaa catcacggct ggggctaacc ctattgaagt gaaacgaggc     2160
atggataaag ccgctgaagc cattattaat gagcttaaaa aagcgagcaa aaaagtgggc    2220
ggtaaagaag aaatcaccca agtggcgacc atttctgcaa actccgatca caatatcggg    2280
aaactcatcg ctgacgctat ggaaaaagtg gtaaagacg gcgtgatcac cgttgaagaa     2340
gctaagggca ttgaagatga actagatgtt gtagaaggca tgcaatttga tagaggctac    2400
ctctccccctt attttgtaac aaacgctgag aaaatgaccg ctcaattgga taacgcttac   2460
atccttttaa cggataaaaa aatctctagc atgaaagaca ttctcccgct actagaaaaa    2520
accatgaaag agggcaaacc gcttttaatc atcgctgaag acattgaggg cgaagcttta   2580
acgactctag tggtgaataa attaagaggc gtgttaaata tcgcagcggt taaagctcca    2640
ggctttgggg acagaagaaa agaaatgctc aaagacatcg ctattttaac cggcggtcaa    2700
gttattagcg aagaattggg cttgagtcta gaaaacgctg aagtggagtt tttaggcaaa    2760
gccggaagga ttgtgattga caaagacaac accacgatcg tagatggcaa aggccatagc    2820
catgatgtca aagacagagt cgcgcaaatc aaaaacccaaa ttgcaagcac gacaagcgat    2880
tatgacaaag aaaaattgca agaaaggttg gctaaactct ctggcggtgt ggctgtgatt    2940
aaagtgggcg ctgcgagtga agtggaaatg aaagagaaaa aagaccgggt tgatgatgcg    3000
ttgagcgcga ctaaagcggc tgttgaagaa ggtattgtga ttggcggcgg tgcggctctc    3060
attcgcgcgg ctcaaaaagt gcatttgaat ttgcacgatg atgaaaaagt gggctatgaa    3120
atcatcatgc gcgccattaa agccccatta gctcaaatcg ctatcaatgc cggttatgat    3180
ggcggtgtgg tcgtgaatga agtagaaaaa cacgaagggc attttggttt taacgctagc    3240
aatggcaagt atgtggatat gtttaaagaa ggcattattg acccccttaaa agtagaaagg   3300
atcgctttac aaaatgcggt ttcggtttca gcctgctttt taaccacaga agccaccgtg    3360
catgaaatca agaagaaaa agcggcccca gcaatgcctg atatgggtgg catgggcggt    3420
atggaggca  tgggtggcat gatgggccct agccttgtgg aagtgcctgg ctctcaacat    3480
attgattctg aaaagaaagc ttaagccccc ttgcttttat ttttttgtcaa tttactattt    3540
ttctttatga ttagctcaag caacaaaagt tattcgtaag gtgcgtttgt tgtaaaaatt    3600
tttgtttgga aggaaaaggc aatgctagga cttgtattgt tatatgttgg gattgtttta    3660
atcagcaatg ggatttgcgg gttaaccaaa gtcgatccta aaagcactgc ggtgatgaac    3720
ttttttgtgg gcggacttc  cattatttgt aatatagttg tcatcactta ttctgcactc    3780
caccctacag cccctgtaga aggtgctgaa gatattgctc aagtatcgca ccatttgact    3840
agtttctatg gaccagcgac tgggttattg ttttggttca cctacttgta tgcggctatc    3900
aaccacactt ttggttttgga ttggaggccc tactcttggt atagcttatt cgtagcgatc   3960
aacacgattc ctgctgcgat tttatcccac tatagcgata tgcttgatga ccacaaagtg    4020
ttaggcatca ctgaaggcga ttggtgggcg atcatttggt tggcttgggg tgttttgtgg    4080
```

-continued

| | |
|---|---:|
| cttaccgctt tcattgaaaa catcttgaaa atcccttag ggaaattcac tccatggctt | 4140 |
| gctatcattg agggtatttt aaccgcttgg atccctgctt ggttgctctt tatccaacac | 4200 |
| tgggtgtgag atgatcatag agcgtttagt tggcaatcta agggatttaa acccttgga | 4260 |
| tttcagcgtg gatcatgtgg atttggaatg gtttgaaacg aggaaaaaaa tcgctcgttt | 4320 |
| taaaaccagg caaggcaaag acatagccat acgccttaaa gacgctccca agttggggct | 4380 |
| ctctcaaggg gatatttat ttaaagaaga gaaggaaatt atcgccgtta atatcttgga | 4440 |
| ttctgaagtc attcacatcc aagccaagag cgtggcagaa gtagcgaaaa tatgctatga | 4500 |
| aataggaaac cgccatgcgg ctttatacta tggcgagtct caatttgaat ttaaaacacc | 4560 |
| atttgaaaag cccacgctag cgttattaga aaagctaggg gttcaaaatc gtgttttaag | 4620 |
| ttcaaaattg gattccaaag aacgcttaac cgtgagcatg ccccatagtg agcctaattt | 4680 |
| taaggtctca ctagcgagcg attttaaagt ggtcgtaaaa tag | 4723 |

<210> SEQ ID NO 4
<211> LENGTH: 4723
<212> TYPE: DNA
<213> ORGANISM: Artificial Sequence
<220> FEATURE:
<223> OTHER INFORMATION: Operon

<400> SEQUENCE: 4

| | |
|---|---:|
| tacttttct aatcgtcttt tcttatacaa agatacatac cgggatgatg tccgctattt | 60 |
| cactctaacc cgctatgtct gaactagcga cttcatcttg tactgatgtg gtaaataccg | 120 |
| cttctcgaat ttaagccacc gccattttgg gactctcttc cgtactcggt taggttgttg | 180 |
| ggatcgtttc ttcttaacct agattagtag tgattgcgaa attagcacct aatgtggcca | 240 |
| taaatatttc gcctataacc ataatttcta ccgttttagc gaccgtaacc atttccgcca | 300 |
| tgtttctgt acgttctacc gcaattttg ttagaatcgc atccaggacg atgacttcgg | 360 |
| aatcggccac ttccaaacta gcattgacga ccaccataac tgtgtgtgta ggtgaagtaa | 420 |
| agtggggttg tttagggatg tcgaaaacgt tcgccacatt gttggtacta accaccgcct | 480 |
| tgaccaggac gactaccgtg attacgctga tgatagtgag gtccgtcttc tttaaatttt | 540 |
| acctacgagt ctcgccgact tcttataaga tacttgaatc caaagaaccg atttccattg | 600 |
| cgaagattgc tgcgctcgaa tcggctagtt aacttcgac cacgctaacc gaaatttag | 660 |
| gtgcttctga ccccgtggtg aggaagacgt tagttagtac gcaatctaca acgtctgttt | 720 |
| atgctacacg ttcagcgata ggtgtgtctg tgaaacttac ttcggccaac gcaccttctg | 780 |
| tgataccgtc gataacggcc tgcgtgatac gtgtgaaagg tgtgacttcc acgaccgccg | 840 |
| cctgtgcgag gactataata atttcatcga ccacttgtgt tgtaagaagg gcgaaggtga | 900 |
| ttgggggtgat agggaaagtg acacttatgt cttcgtcttg tgtacctgta cgaataccac | 960 |
| acggtggtga acctatttc gtaatttctt ctacaagtca agcgactaag ttcctaggcg | 1020 |
| ggagtttggt aacgccgact tctgtgaaac gtactgtacc cctaaaagag ttagtggtcg | 1080 |
| agactgagag ttcgataccc agcacaccca cttcaatagt gatcttgaac cgtttgtcga | 1140 |
| ctgttttgt tttttcttaa accggcgaac tttcttcttt ttccgctatt gctgttgaag | 1200 |
| tcctagtttg cgatgaacag atttatgtgg taattgggtc gctagcgagt accctaatcg | 1260 |
| ctcatacatc caagacatct tcacccgttt caccgactga accataacac ctcagggcgt | 1320 |
| aagaaaccgc atttgggtt gtactagtag tttccgccca agtaacgcaa ctcagtttac | 1380 |
| ccactgcgct tgcgaagata gggatggggt gttggtcaaa taatgtctct ttacaagcga | 1440 |

```
gtagtaccat ttcggtttat gctacgtttg tagtgaaaac acagagttcg ccgaatactg    1500 ttttccgtaat ttcttcttaa tcccgaactt tctgttcaca acggccattt tttaacgtct   1560
ttgtagtgat tttttctgta cgttaagttg ctgtgatggc gagtgtaact tcagttagga    1620 cttttgaatgg tacacaagca cctaccgttt cttcattgaa gatttggtcg gttatttcac   1680
tcgaaccgcg ttgagaaatc gtaaaagatc ctaaaaaatc ctcgttgcga ggaatttagg    1740
aatcaaaaat cgagagacta aaaacaaat agttttttaa ccccgaaaa aaacattcct      1800 atgttttacc gttttcttta gtttaaaagt ctatcgcgct cttttggaaaa taaacttccg   1860 cactctgttg aggtactgcg acaatttcat tggtaccccg gttctccgtc cttgcacaac    1920 taggttttt cgataccgcg aggttcgtag tgatttctac cgcactcgca ccgatttctc     1980
taacttaatt caacgggcca tcgattgtac ccgcgagttg agcaatttct tcatcgctcg    2040
ttttggcgac tacgacggcc gctaccgtgc tggtgtcgct ggcacgaccg aatatcgtaa    2100
aaatttcttc caaactcctt gtagtgccga ccccgattgg gataacttca ctttgctccg    2160
tacctatttc ggcgacttcg gtaataatta ctcgaatttt ttcgctcgtt ttttcacccg    2220
ccatttcttc tttagtgggt tcaccgctgg taaagacgtt tgaggctagt gttatagccc    2280
tttgagtagc gactgcgata ccttttttcac ccatttctgc cgcactagtg gcaacttctt   2340
cgattcccgt aacttctact tgatctacaa catcttccgt acgttaaact atctccgatg    2400
gagaggggaa taaaacattg tttgcgactc ttttactggc gagttaacct attgcgaatg    2460
taggaaaatt gcctattttt ttagagatcg tactttctgt aagagggcga tgatcttttt    2520
tggtactttc tcccgtttgg cgaaaattag tagcgacttc tgtaactccc gcttcgaaat    2580
tgctgagatc accacttatt taattctccg cacaacttat agcgtcgcca atttcgaggt    2640
ccgaaacccc tgtcttcttt tctttacgag tttctgtagc gataaaattg gccgccagtt    2700
caataatcgc ttcttaaccc gaactcagat cttttgcgac ttcacctcaa aaatccgttt    2760
cggccttcct aacactaact gtttctgttg tggtgctagc atctaccgtt tccggtatcg    2820
gtactacagt ttcctgtctca gcgcgtttag ttttgggttt aacgttcgtg ctgttcgcta    2880
atactgtttc ttttttaacgt tcttttccaac cgatttgaga gaccgccaca ccgacactaa    2940
tttcacccgc gacgctcact tcaccttttac tttctctttt ttctggccca actactacgc   3000
aactcgcgct gatttcgccg acaacttctt ccataacact aaccgccgcc acgccgagag    3060
taagcgcgcc gagttttttca cgtaaactta aacgtgctac tacttttttca cccgatactt    3120 tagtagtacg cgcggtaatt tcggggtaat cgagtttagc gatagttacg gccaatacta    3180
ccgccacacc agcacttact tcatcttttt gtgcttcccg taaaaccaaa attgcgatcg    3240
ttaccgttca tacacctata caaatttctt ccgtaataac tggggaattt tcatctttcc    3300
tagcgaaatg ttttacgcca aagccaaagt tcggacgaaa attggtgtct tcggtggcac    3360
gtactttagt ttcttctttt tcgccggggt cgttacggac tatacccacc gtacccgcca    3420
taccctccgt acccaccgta ctacccggga tcggaacacc ttcacggacc gagagttgta   3480
taactaagac ttttctttcg aattcggggg aacgaaaata aaaaacagtt aaatgataaa    3540 agaaatact aatcgagttc gttgttttca ataagcattc cacgcaaaca acatttttaa     3600
aaacaaacct tcctttttccg ttacgatcct gaacataaca atatacaacc ctaacaaaat   3660
tagtcgttac cctaaacgcc caattggttt cagctaggat tttcgtgacg ccactacttg    3720
aaaaaacacc cgcctgaaag gtaataaaca ttatatcaac agtagtgaat aagacgtgag    3780
gtgggatgtc ggggacatct tccacgactt ctataacgag ttcatagcgt ggtaaactga    3840
```

```
tcaaagatac ctggtcgctg acccaataac aaaccaaagt ggatgaacat acgccgatag    3900
ttggtgtgaa aaccaaacct aacctccggg atgagaacca tatcgaataa gcatcgctag    3960
ttgtgctaag gacgacgcta aaatagggtg atatcgctat acgaactact ggtgtttcac    4020
aatccgtagt gacttccgct aaccacccgc tagtaaacca accgaacccc acaaaacacc    4080
gaatggcgaa agtaactttt gtagaacttt tagggaaatc cctttaagtg aggtaccgaa    4140
cgatagtaac tcccataaaa ttggcgaacc tagggacgaa ccaacgagaa ataggttgtg    4200
acccacactc tactagtatc tcgcaaatca accgttagat tccctaaatt tggggaacct    4260
aaagtcgcac ctagtacacc taaaccttac caaactttgc tccttttttt agcgagcaaa    4320
attttggtcc gttccgtttc tgtatcggta tgcggaattt ctgcgagggt tcaaccccga    4380
gagagttccc ctataaaata aatttcttct cttcctttaa tagcggcaat tatagaacct    4440
aagacttcag taagtgtagg ttcggttctc gcaccgtctt catcgctttt atacgatact    4500
ttatcctttg gcggtacgcc gaaatatgat accgctcaga gttaaactta aattttgtgg    4560
taaacttttc gggtgcgatc gcaataatct tttcgatccc caagttttag cacaaaattc    4620
aagttttaac ctaaggtttc ttgcgaattg gcactcgtac ggggtatcac tcggattaaa    4680
attccagagt gatcgctcgc taaaatttca ccagcatttt atc                       4723

<210> SEQ ID NO 5
<211> LENGTH: 40
<212> TYPE: DNA
<213> ORGANISM: Artificial Sequence
<220> FEATURE:
<223> OTHER INFORMATION: Primer

<400> SEQUENCE: 5
acggtatcga taagcttagc actaccttga catggtagtg                           40

<210> SEQ ID NO 6
<211> LENGTH: 43
<212> TYPE: DNA
<213> ORGANISM: Artificial Sequence
<220> FEATURE:
<223> OTHER INFORMATION: Primer

<400> SEQUENCE: 6
ttcagatctg aattcttact ccttaattgt ttttacatag ttg                       43

<210> SEQ ID NO 7
<211> LENGTH: 49
<212> TYPE: DNA
<213> ORGANISM: Artificial Sequence
<220> FEATURE:
<223> OTHER INFORMATION: Primer

<400> SEQUENCE: 7
gagtaagaat tcagatctga atgaaaaag attagcagaa aagaatatg                  49

<210> SEQ ID NO 8
<211> LENGTH: 37
<212> TYPE: DNA
<213> ORGANISM: Artificial Sequence
<220> FEATURE:
<223> OTHER INFORMATION: Primer

<400> SEQUENCE: 8
aactgatcta gaggatcctt gaatcagcga actgaac                              37
```

```
<210> SEQ ID NO 9
<211> LENGTH: 45
<212> TYPE: DNA
<213> ORGANISM: Artificial Sequence
<220> FEATURE:
<223> OTHER INFORMATION: Primer

<400> SEQUENCE: 9
gacggtatcg ataagcttca tgcgttagat gttgcagaca aatac            45

<210> SEQ ID NO 10
<211> LENGTH: 50
<212> TYPE: DNA
<213> ORGANISM: Artificial Sequence
<220> FEATURE:
<223> OTHER INFORMATION: Primer

<400> SEQUENCE: 10
gacaaaaaat aaaagatctc gaattcacaa aaaaagcccc caattttttg        50

<210> SEQ ID NO 11
<211> LENGTH: 49
<212> TYPE: DNA
<213> ORGANISM: Artificial Sequence
<220> FEATURE:
<223> OTHER INFORMATION: Primer

<400> SEQUENCE: 11
gtgaattcag atctttttat tttttgtcaa tttactattt ttctttatg          49

<210> SEQ ID NO 12
<211> LENGTH: 37
<212> TYPE: DNA
<213> ORGANISM: Artificial Sequence
<220> FEATURE:
<223> OTHER INFORMATION: Primer

<400> SEQUENCE: 12
aactatctag aggatgtgaa tgacttcaga atccaag                      37

<210> SEQ ID NO 13
<211> LENGTH: 10
<212> TYPE: DNA
<213> ORGANISM: Artificial Sequence
<220> FEATURE:
<223> OTHER INFORMATION: Ribosome Binding Sequence

<400> SEQUENCE: 13
aggatacaaa                                                    10

<210> SEQ ID NO 14
<211> LENGTH: 858
<212> TYPE: DNA
<213> ORGANISM: Artificial Sequence
<220> FEATURE:
<223> OTHER INFORMATION: Fusion construct

<400> SEQUENCE: 14
atggaaatac aacaaacaca ccgcaaaatc aatcgccctt tggtttctct cgctttagta    60
ggagcgttag tcagcatcac accgcaacaa agtcatgccg cctttggcgg ccgcagcatt   120
attaattttg aaaaattagg gcctagctta gatgatcctc ctgctaccgt gtataaatat   180
gatagcagac tcctgaaga tgtgtttcaa aatgggttta ccgcttgggg gaataatgat   240
aatgtgttag tcatttaac cgggagaagc tgccaagtgg ggagcagcaa tagcgctttt   300
gtgagcacca gcagcagcag aagatatacc gaagtgtatt tagaacatag aatgcaagaa   360
```

```
gctgtggaag ctgaaagagc tgggagaggg accgggcatt ttattgggta tatttatgaa    420
gtgagagctg ataataattt ttatggggct gctagcagct attttgaata tgtggatacc    480
tatggggata atgctgggag aattttagct ggggctttag ctacctatca aagcgggtat    540
ttagctcata gaagaattcc tcctgaaaat attagaagag tgaccagagt gtatcataat    600
gggattaccg gggaaaccac caccaccgaa tatagcaatg ctagatatgt gagccaacaa    660
accagagcta atcctaatcc ttataccagc agaagaagcg tggctagcat tgtggggacc    720
ttagtgagaa tggctcctgt gattggggct tgcatggcta gacaagctga aagcagcgaa    780
gctatggctg cttggagcga aagagctggg gaagctatgg tgttagtgta ttatgaaagc    840
attgcttata gcttttaa                                                  858

<210> SEQ ID NO 15
<211> LENGTH: 381
<212> TYPE: DNA
<213> ORGANISM: Artificial Sequence
<220> FEATURE:
<223> OTHER INFORMATION: CtxB fusion

<400> SEQUENCE: 15
atggaaatac aacaaacaca ccgcaaaatc aatcgccctt tggtttctct cgctttagta     60
ggagcgttag tcagcatcac accgcaacaa agtcatgccg cctttacacc tcaaaatatt    120
actgatttgc tcgaggaatc acacaacaca caaatatata cgctaaatga taagatattt    180
tcgtatacag aatctctagc tggaaaaaga gagatggcta tcattacttt taagaatggt    240
gcaatttttc aagtagaagt accaggtagt caacatatag attcacaaaa aaaagcgatt    300
gaaaggatga aggataccct gaggattgca tatcttactg aagctaaagt cgaaaagtta    360
ggtgtaggga ataataaaac g                                              381

<210> SEQ ID NO 16
<211> LENGTH: 1488
<212> TYPE: DNA
<213> ORGANISM: Artificial Sequence
<220> FEATURE:
<223> OTHER INFORMATION: CTP3-htrA fusion

<400> SEQUENCE: 16
atgatgaaaa aaccccttttt tatctctttg ctttagcgt taagcttgaa tgcggtggaa     60
gtgcctggga gccaacatat tgatagccaa aaaaagctg ggcctagctt aggcaatatc    120
caaatccaga gcatgcccaa agttaaagag cgagtgagtg tccctctaa agacgatacg    180 atctattctt accacgattc tattaaggac tctattaagg cggtggtgaa tatctccact    240
gaaaagaaga ttaaaaacaa ttttataggt ggcggtgtgt ttaatgaccc cttttttccaa    300 caatttttttg gggatttggg tggcatgatt cctaaagaaa gaatgaaaag gctttaggc    360 agcggcgtaa tcatttctaa agacggctat attgtaacta taaccatgt gattgatggc    420 gcggataaga ttaaagttac cattccaggg agcaataaag aatattccgc cactctagta    480
ggcaccgatt ctgaaagcga tttagcgtg attcgcatca ctaaagacaa tctgcccacg    540
atcaaattct ctgattctaa tgatatttca gtgggcgatt tggttttttgc gattggtaac    600 ccttttggcg tgggcgaaag cgttacgcaa ggcattgttt cagcgctcaa taaaagcggg    660
attgggatca acagctatga gaatttcatt caaacagacg cttccatcaa tcctggaaat    720
tccggcggcg ctttaattga tagccgtgga gggttagtgg ggattaatac cgctattatc    780
tctaaaactg ggggcaacca cggcattggc tttgccatcc cttctaacat ggttaaagat    840
```

```
actgtaaccc aactcatcaa aaccggtaag attgaaagag gttacttggg cgtgggcttg      900
caagatttga gtggcgattt gcaaaattct tatgacaaca agaagggggc ggtagtcatt      960
agcgtagaaa aagactctcc ggctaaaaaa gcaggpattt tggtgtggga tttgatcacc     1020
gaagtcaatg ggaaaaaggt taaaaacacg aatgagttaa gaaatctaat cggctccatg     1080
ctacccaatc aaagagtaac cttaaaagtc attagagaca aaaagaacg cgctttcacc      1140 ctcactctag ctgaaaggaa aaaccctaac aaaaaagaaa ccatttctgc tcaaaacggc     1200
gcgcaaggcc aattgaacgg gcttcaagta gaagatttaa ctcaagaaac caaaaggtct    1260
atgcgtttga gcgatgatgt tcaaggggtt ttagtctctc aagtgaatga aaattcccca    1320
gcagagcaag ccggatttag gcaaggtaac attatcacaa aaattgaaga ggttgaagtt    1380
aaaagcgttg cggattttaa ccatgcttta gaaaagtata aaggcaaacc caaacgattc    1440
ttagttttag acttgaatca aggttatagg atcattttgg tgaaatga                 1488
```

<210> SEQ ID NO 17
<211> LENGTH: 1383
<212> TYPE: DNA
<213> ORGANISM: Artificial Sequence
<220> FEATURE:
<223> OTHER INFORMATION: lpp20-HAM2

<400> SEQUENCE: 17

```
atgaaaaatc aagttaaaaa aattttaggg atgagtgtgg tagcagcgat ggtgatcgta       60
ggttgcagcc atgccccaaa atcaggtatc agcaaaagca ataaggcata caagaagcg      120 actaaaggcg ctcctgattg ggtggtaggg gatttagaaa aagtggcgaa gtatgaaaag     180
tattcagggg tcttttttagg aagggctgaa gatttgatca ctaataacga tgtggattat    240
tctactaacc aagctacagc gaaagctagg gctaatttag cggcgaattt aaaatccact     300
ttacaaaaag atttggaaaa tgaaaaaact agaacggtag acgcttctgg taaaaggtcc     360
atcagcggca ctgatactga aaaaatttct caattagtgg ataaggaatt gattgcttct     420
aaaatgcttg cccgctatgt tggtaaagat agggttttttg ttttagtggg cttggataag    480
caaattgtgg ataaagtgcg cgaagagttg gcggccgct tatgcagatt aaaagggatt      540 gctccttttac aattagggaa atgcaatatt gctgggtggt tattagggaa tcctgaatgc    600
gatcctttat tacctgtgag aagctggagc tatattgtgg aaaccctaa tagcgaaaat     660 gggatttgct atcctgggga ttttattgat tatgaagaat taagaaaca attaagcagc     720 gtgagcagct ttgaaagatt tgaaatttt cctaaagaaa gcagctggcc taatcataat    780
accaccaaag gggtgaccgc tgcttgcagc catgctggga aaagcagctt ttatagaaat    840
ttattatggt taaccgaaaa agaagggagc tatcctaaat taaaaaatag ctatgtgaat     900
aaaaaaggga agaagtgtt agtgttatgg gggattcatc atcctagcaa tagcaaagat     960
caacaaaata tttatcaaaa tgaaatgct tatgtgagcg tggtgaccag caattataat    1020
agaagattta cccctgaaat tgctgaaaga cctaaagtga gagatcaagc tgggagaatg    1080
aattattatt ggaccttatt aaaacctggg gataccatta ttttttgaagc taatgggaat     1140 ttaattgctc ctagatatgc ttttgcttta agcagagggt ttgggagcgg gattattacc    1200
agcaatgcta gcatgcatga aagcttatta accgaagtg aaaccctat tagaaatgaa       1260 tgggggtgca gatgcaatga tagcagcgat gggcctagct taagcttatt aaccgaagtg    1320
gaaaccccta ttagaaatga atggggggtgc agatgcaatg atagcagcga tgggcctagc    1380
tta                                                                 1383
```

<210> SEQ ID NO 18
<211> LENGTH: 1074
<212> TYPE: DNA
<213> ORGANISM: Artificial Sequence
<220> FEATURE:
<223> OTHER INFORMATION: HcpA-3M2-HA fusion

<400> SEQUENCE: 18

| | | | | | |
|---|---|---|---|---|---|
| atgctaggaa | acgttaaaaa | aacccttttt | ggggtcttgt | gtttgggcac | gttgtgtttg | 60 |
| agagggttaa | tggcagagcc | agacgctaaa | gagcttgtta | atttaggcat | agagagcgcg | 120 |
| aagaagcaag | atttcgctca | agctaaaacg | cattttgaaa | aagcttgtga | gttaaaaaat | 180 |
| ggctttggat | gtgttttttt | agggcgttc | tatgaagaag | ggaaggagt | gggaaaagac | 240 |
| ttgaaaaaag | ccatccaatt | ttacactaaa | ggttgtgaat | taaatgatgg | ttatgggtgt | 300 |
| aacctgctag | gaaatttata | ctataacgga | caaggcgtgt | caaaagacgc | taaaaaagcc | 360 |
| tcacaatact | actctaaagc | ttgcgactta | aaccatgctg | aagggtgtat | ggtattagga | 420 |
| agcttacacc | attatggcgt | aggcacgcct | aaggatttaa | aaaggctct | tgatttgtat | 480 |
| gaaaaagctt | gcgatttaaa | agacagccca | gggtgtatta | atgcaggata | tatatatagt | 540 |
| gtaacaaaga | attttaagga | ggctatcgtt | cgttattcta | aagcatgcga | attaaaagat | 600 |
| ggtaggggt | gttataattt | aggggttatg | caatacaacg | ctcaaggtac | agcaaaggac | 660 |
| gaaaagcaag | cggtagaaaa | ctttaaaaaa | ggctgcaaat | caagcgttaa | gaagcatgc | 720 |
| gacgctctca | aggaattaaa | aatagaactt | ggcggccgca | gcttattaac | cgaagtggaa | 780 |
| accctatta | gaaatgaatg | ggggtgcaga | tgcaatgata | gcagcgatgg | gcctagctta | 840 |
| agcttattaa | ccgaagtgga | aaccctatt | agaaatgaat | ggggtgcag | atgcaatgat | 900 |
| agcagcgatg | ggcctagctt | aagcttatta | accgaagtgg | aaaccctat | agaaatgaa | 960 |
| tgggggtgca | gatgcaatga | tagcagcgat | gggcctagct | tatttgaaag | atttgaaatt | 1020 |
| tttcctaaag | aagggcctag | cttatggtta | accgaaaaag | aagggagcta | tcct | 1074 |

<210> SEQ ID NO 19
<211> LENGTH: 810
<212> TYPE: DNA
<213> ORGANISM: Artificial Sequence
<220> FEATURE:
<223> OTHER INFORMATION: HcpA-CTP3

<400> SEQUENCE: 19

| | | | | | |
|---|---|---|---|---|---|
| atgctaggaa | acgttaaaaa | aacccttttt | ggggtcttgt | gtttgggcac | gttgtgtttg | 60 |
| agagggttaa | tggcagtgga | agtgcctggg | agccaacata | ttgatagcca | aaaaaaagct | 120 |
| gggcctagct | tagagccaga | cgctaaagag | cttgttaatt | taggcataga | gagcgcgaag | 180 |
| aagcaagatt | tcgctcaagc | taaaacgcat | tttgaaaaag | cttgtgagtt | aaaaaatggc | 240 |
| tttggatgtg | ttttttttagg | ggcgttctat | gaagaaggga | aggagtggg | aaaagacttg | 300 |
| aaaaaagcca | tccaattta | cactaaaggt | tgtgaattaa | atgatggtta | tgggtgtaac | 360 |
| ctgctaggaa | atttatacta | taacggacaa | ggcgtgtcaa | aagacgctaa | aaaagcctca | 420 |
| caatactact | ctaaagcttg | cgacttaaac | catgctgaag | ggtgtatggt | attaggaagc | 480 |
| ttacaccatt | atggcgtagg | cacgcctaag | gatttaagaa | aggctcttga | tttgtatgaa | 540 |
| aaagcttgcg | atttaaaaga | cagcccaggg | tgtattaatg | caggatatat | atatagtgta | 600 |
| acaaagaatt | ttaaggaggc | tatcgttcgt | tattctaaag | catgcgaatt | aaaagatggt | 660 |
| aggggtgtt | ataatttagg | ggttatgcaa | tacaacgctc | aaggtacagc | aaaggacgaa | 720 |

| aagcaagcgg tagaaaactt taaaaaaggc tgcaaatcaa gcgttaaaga agcatgcgac | 780 |
| gctctcaagg aattaaaaat agaactttaa | 810 |

<210> SEQ ID NO 20
<211> LENGTH: 1137
<212> TYPE: DNA
<213> ORGANISM: Artificial Sequence
<220> FEATURE:
<223> OTHER INFORMATION: PrsA-3M2HA fusion

<400> SEQUENCE: 20

| atgaaaaaaa atatcttaaa tttagcgtta gtgggtgcgt tgagcacgtc gttttttgatg | 60 |
| gctaagccgg ctcataacgc aaataacgct acgcataaca cgaaaaaaac gactgattct | 120 |
| tcagcaggcg tgttagcgac agtggatggc agacctatca ctaaaagcga ttttgacatg | 180 |
| attaagcaac gaaatcctaa tttttgatttt gacaagctta agagaaaga aaaagaagcc | 240 |
| ttgattgatc aagctattcg caccgccctt gtagaaaatg aagctaaaac cgagaaattg | 300 |
| gacagcactc cagaatttaa agcgatgatg gaagcggtta aaaaacaggc tttagtggaa | 360 |
| ttttgggcta aaaaacaggc tgaagaagtg aaaaaagtcc aatcccaga aaagaaatg | 420 |
| caagatttt acaacgctaa caaagatcag cttttttgtca agcaagaagc ccatgctagg | 480 |
| catattttag tgaaaaccga agatgaggct aaacggatta tttctgagat tgacaaacag | 540 |
| ccaaaggcta aaaagaagc taaattcatt gagttagcca atcgggatac gattgatcct | 600 |
| aacagcaaga acgcgcaaaa tggcggtgat ttgggggaaat tccaaaagaa ccaaatggct | 660 |
| ccggattttt ctaaagccgc tttcgcttta actcctgggg attacactaa aacccctgtt | 720 |
| aaaacagagt ttggttatca tattatctat ttgatttcta agatagccc tgtaacttat | 780 |
| acttatgaac aggctaaacc taccattaag gggatgttac aagaaaagct tttccaagaa | 840 |
| cgcatgaatc aacgcattga ggaactaaga aagcacgcta aaattgttat caacaagggc | 900 |
| ggccgcagct tattaaccga agtggaaacc cctattagaa atgaatgggg gtgcagatgc | 960 |
| aatgatagca gcgatgggcc tagcttaagc ttattaaccg aagtggaaac ccctattaga | 1020 |
| aatgaatggg ggtgcagatg caatgatagc agcgatgggc tagcttaag cttattaacc | 1080 |
| gaagtggaaa ccctattag aaatgaatgg gggtgcagat gcaatgatag cagcgat | 1137 |

<210> SEQ ID NO 21
<211> LENGTH: 1980
<212> TYPE: DNA
<213> ORGANISM: Artificial Sequence
<220> FEATURE:
<223> OTHER INFORMATION: GroEL 3M2-HA fusion

<400> SEQUENCE: 21

| atggcaaaag aaatcaaatt ttcagatagc gcgagaaacc ttttatttga aggcgtgaga | 60 |
| caactccatg acgctgttaa agtaaccatg gggccaagag gcaggaacgt gttgatccaa | 120 |
| aaaagctatg cgctccaag catcactaaa gatggcgtga gcgtggctaa agagattgaa | 180 |
| ttaagttgcc cggtagctaa catgggcgct caactcgtta agaagtagc gagcaaaacc | 240 |
| gctgatgctg ccggcgatgg cacgaccaca gcgaccgtgc tggcttatag catttttaaa | 300 |
| gaaggtttga ggaacatcac ggctgggggct aaccctattg aagtgaaacg aggcatggat | 360 |
| aaagccgctg aagccattat taatgagctt aaaaaagcga gcaaaaaagt gggcggtaaa | 420 |
| gaagaaatca cccaagtggc gaccattcct gcaaactccg atcacaatat cgggaaactc | 480 |
| atcgctgacg ctatggaaaa agtgggtaaa gacggcgtga tcaccgttga agaagctaag | 540 |

```
ggcattgaag atgaactaga tgttgtagaa ggcatgcaat ttgatagagg ctacctctcc    600
ccttattttg taacaaacgc tgagaaaatg accgctcaat tggataacgc ttacatcctt    660
ttaacggata aaaaaatctc tagcatgaaa gacattctcc cgctactaga aaaaaccatg    720
aaagagggca accgctttt aatcatcgct gaagacattg agggcgaagc tttaacgact    780
ctagtggtga ataaattaag aggcgtgttg aatatcgcag cggttaaagc tccaggcttt    840
ggggacagaa gaaaagaaat gctcaaagac atcgctattt taaccggcgg tcaagttatt    900
agcgaagaat tgggcttgag tctagaaaac gctgaagtgg agttttttagg caaagccgga    960 aggattgtga ttgacaaaga caacaccacg atcgtagatg gcaaaggcca tagccatgat   1020
gtcaaagaca gagtcgcgca aatcaaaacc caaattgcaa gcacgacaag cgattatgac   1080
aaagaaaaat tgcaagaaag gttggctaaa ctctctggcg gtgtggctgt gattaaagtg   1140
ggcgctgcga gtgaagtgga aatgaaagag aaaaaagacc gggttgatga tgcgttgagc   1200
gcgactaaag cggctgttga agaaggtatt gtgattggcg gcggtgcggc tctcattcgc   1260
gcggctcaaa aagtgcattt gaatttgcac gatgatgaaa agtgggcta tgaaatcatc    1320 atgcgcgcca ttaaagcccc attagctcaa atcgctatca atgccggtta tgatggcggt   1380
gtggtcgtga atgaagtaga aaaacacgaa gggcattttg gttttaacgc tagcaatggc   1440
aagtatgtgg atatgtttaa agaaggcatt attgacccct aaaagtaga aaggatcgct    1500 ttacaaaatg cggtttcggt ttcaagcctg cttttaacca cagaagccac cgtgcatgaa    1560
atcaaagaag aaaaagcggc cccagcaatg cctgatatgg gtggcatggg cggtatggga    1620
ggcatgggtg gcatgatggg ctccggcggc ggctccggct ccagcttatt aaccgaagtg    1680 gaaacccta ttagaaatga atgggggtgc agatgcaatg atagcagcga tgggcctagc     1740
ttaagcttat taaccgaagt ggaaaccct attagaaatg aatggggtg cagatgcaat      1800 gatagcagcg atgggcctag cttaagctta ttaaccgaag tggaaacccc tattagaaat   1860 gaatggggt gcagatgcaa tgatagcagc gatgggccta gcttatttga aagatttgaa    1920
atttttccta aagaagggcc tagcttatgg ttaaccgaaa agaagggag ctatccttaa     1980
```

<210> SEQ ID NO 22
<211> LENGTH: 2367
<212> TYPE: DNA
<213> ORGANISM: Artificial Sequence
<220> FEATURE:
<223> OTHER INFORMATION: GroEL- HA

<400> SEQUENCE: 22

```
atggcaaaag aaatcaaatt ttcagatagc gcgagaaacc ttttatttga aggcgtgaga     60
caactccatg acgctgttaa agtaaccatg gggccaagag gcaggaacgt gttgatccaa    120
aaaagctatg cgctccaag catcactaaa gatggcgtga gcgtggctaa agagattgaa     180
ttaagttgcc cggtagctaa catgggcgct caactcgtta agaagtagc gagcaaaacc     240 gctgatgctg ccggcgatgg cacgaccaca gcgaccgtgc tggcttatag catttttaaa    300
gaaggtttga ggaacatcac ggctgggct aaccctattg aagtgaaacg aggcatggat     360
aaagccgctg aagccattat taatgagctt aaaaaagcga gcaaaaagt gggcggtaaa    420 gaagaaatca cccaagtggc gaccatttct gcaaactccg atcacaatat cgggaaactc    480
atcgctgacg ctatggaaaa agtgggtaaa gacggcgtga tcaccgttga agaagctaag   540
ggcattgaag atgaactaga tgttgtagaa ggcatgcaat ttgatagagg ctacctctcc    600
ccttattttg taacaaacgc tgagaaaatg accgctcaat tggataacgc ttacatcctt    660
```

-continued

```
ttaacggata aaaaaatctc tagcatgaaa gacattctcc cgctactaga aaaaaccatg    720
aaagagggca aaccgctttt aatcatcgct gaagacattg agggcgaagc tttaacgact    780
ctagtggtga ataaattaag aggcgtgttg aatatcgcag cggttaaagc tccaggcttt    840
ggggacagaa gaaaagaaat gctcaaagac atcgctattt taaccggcgg tcaagttatt    900
agcgaagaat tgggcttgag tctagaaaac gctgaagtgg agttttagg caaagccgga     960 aggattgtga ttgacaaaga caacaccacg atcgtagatg gcaaaggcca tagccatgat   1020
gtcaaagaca gagtcgcgca aatcaaaacc caaattgcaa gcacgacaag cgattatgac   1080
aaagaaaaat tgcaagaaag gttggctaaa ctctctggcg gtgtggctgt gattaaagtg   1140
ggcgctgcga gtgaagtgga aatgaaagag aaaaagacc gggttgatga tgcgttgagc    1200
gcgactaaag cggctgttga agaaggtatt gtgattggcg gcggtgcggc tctcattcgc   1260
gcggctcaaa aagtgcattt gaatttgcac gatgatgaaa aagtgggcta tgaaatcatc   1320
atgcgcgcca ttaaagcccc attagctcaa atcgctatca atgccggtta tgatggcggt   1380
gtggtcgtga atgaagtaga aaaacacgaa gggcattttg gttttaacgc tagcaatggc   1440
aagtatgtgg atatgtttaa agaaggcatt attgacccct taaaagtaga aaggatcgct   1500
ttacaaaatg cggtttcggt ttcaagcctg cttttaacca cagaagccac cgtgcatgaa   1560
atcaaagaag aaaaagcggc cccagcaatg cctgatatgg gtggcatggg cggtatggga   1620
ggcatgggtg gcatgatggg ctccggcggc ggctccggct ccttatgcag attaaaaggg   1680
attgctcctt tacaattagg gaaatgcaat attgctgggt ggttattagg gaatcctgaa   1740
tgcgatcctt tattacctgt gagaagctgg agctatattg tggaaccccc taatagcgaa   1800
aatgggattt gctatcctgg ggattttatt gattatgaag aattaagaga acaattaagc   1860
agcgtgagca gctttgaaag atttgaaatt tttcctaaag aaagcagctg gcctaatcat   1920
aataccacca aagggggtgac cgctgcttgc agccatgctg ggaaaagcag cttttataga   1980
aatttattat ggttaaccga aaaagaaggg agctatccta aattaaaaaa tagctatgtg   2040
aataaaaaag ggaaagaagt gttagtgtta tgggggattc atcatcctag caatagcaaa   2100
gatcaacaaa atatttatca aaatgaaaat gcttatgtga gcgtggtgac cagcaattat   2160
aatagaagat ttaccctga aattgctgaa agacctaaag tgagagatca agctgggaga    2220
atgaattatt attggaccttt attaaaacct ggggatacca ttatttttga agctaatggg   2280
aatttaattg ctcctagata tgcttttgct ttaagcagag ggtttgggag cgggattatt   2340
accagcaatg ctagcatgca tgaataa                                       2367
```

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ctcattaggc accccaggct tta                                              23

<210> SEQ ID NO 24
<211> LENGTH: 61
<212> TYPE: DNA
<213> ORGANISM: Artificial Sequence
<220> FEATURE:
<223> OTHER INFORMATION: Primer

<400> SEQUENCE: 24

```
ttagcgatcg cccatgtagc ggccgcatcg atatcgaatt cttactcctt aattgttttt    60
a                                                                    61

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
gatgtgctgc aaggcgatta agttg                                          25

<210> SEQ ID NO 26
<211> LENGTH: 62
<212> TYPE: DNA
<213> ORGANISM: Artificial Sequence
<220> FEATURE:
<223> OTHER INFORMATION: Primer

<400> SEQUENCE: 26
tacatgggcg atcgctaaag atctaggagt aactaatgaa aaagattagc agaaaagaat    60
at                                                                   62

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
cagtcacgac gttgtaaaac gacgg                                          25

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
caggaaacag ctatgaccat gattacgc                                       28

<210> SEQ ID NO 29
<211> LENGTH: 4703
<212> TYPE: DNA
<213> ORGANISM: Artificial Sequence
<220> FEATURE:
<223> OTHER INFORMATION: Plasmid

<400> SEQUENCE: 29
cgggcccccc ctcgatcgac ggtatcgata tgaaactcac cccaaaagag ttagacaagt    60
tgatgctcca ctatgctgga gaattggcta aaaaacgcaa agaaaaaggc attaagctta   120
actatgtaga agcggtagct ttgattagtg cccatattat ggaagaagcg agagctggta   180
aaaagactgc ggctgaattg atgcaagaag ggcgcactct tttaaaaccg gatgatgtga   240
tggatggcgt ggcaagcatg atccatgaag tgggtattga agcgatgttt cctgatggga   300
caaaactcgt aaccgtgcat accctattg aggccaatgg taaattagtt cctggtgagt   360
tgttcttaaa aaatgaagac atcactatca acgaaggcaa aaaagccgtt agcgtgaaag   420
ttaaaaatgt tggcgacaga ccggttcaaa tcggctcaca cttccatttc tttgaagtga   480
```

```
atagatgctt agactttgac agagaaaaaa ctttcggtaa acgcttagac attgcgagcg    540
ggacagcggt aaggtttgag cctggcgaag aaaaatccgt agaattgatt gacattggcg    600
gtaacagaag aatctttgga tttaacgcgt tggttgatag gcaagcagac aacgaaagca    660
aaaaaattgc tttacacaga gctaaagagc gtggttttca tggcgctaaa agcgatgaca    720
actatgtaaa aacaattaag gagtaagaat tcgatatcga tgcggccgct acatgggcga    780
tcgctaaaga tctaggagta actaatgaaa aagattagca gaaaagaata tgtttctatg    840
tatggcccta ctacaggcga taaagtgaga ttgggcgata cagacttgat cgctgaagta    900
gaacatgact acaccattta tggcgaagag cttaaattcg gtggcggtaa aaccctgaga    960
gaaggcatga gccaatccaa caaccctagc aaagaagaat tggatctaat catcactaac   1020
gctttaatcg tggattacac cggtatttat aaagcggata ttggtattaa agatggcaaa   1080
atcgctggca ttggtaaagg cggtaacaaa gacatgcaag atggcgttaa aaacaatctt   1140
agcgtaggtc ctgctactga agccttagcc ggtgaaggtt tgatcgtaac tgctggtggt   1200
attgacacac acatccactt catttcaccc caacaaatcc ctacagcttt tgcaagcggt   1260
gtaacaacca tgattggtgg cggaactggt cctgctgatg gcactaatgc gactactatc   1320
actccaggca gaagaaattt aaaatggatg ctcagagcgg ctgaagaata ttctatgaac   1380
ttaggtttct tggctaaagg taacgcttct aacgacgcga gcttagccga tcaaattgaa   1440
gctggtgcga ttggctttaa aatccacgaa gactggggca ccactccttc tgcaatcaat   1500
catgcgttag atgttgcaga caaatacgat gtgcaagtcg ctatccacac agacactttg   1560
aatgaagccg gttgcgtgga agacactatg gcagctattg ccggacgcac tatgcacact   1620
ttccacactg aaggtgctgg cggcggacac gctcctgata ttattaaagt agctggtgaa   1680
cacaacattc ttcccgcttc cactaacccc actatccctt tcactgtgaa tacagaagca   1740
gaacacatgg acatgcttat ggtgtgccac cacttggata aaagcattaa agaagatgtt   1800
cagttcgctg attcaaggat cctctagagc ggccggccgc caccgcggtg gccaattcgc   1860
cctatagtga gtcgtattac aattcactgg ccgtcgtttt acaacgtcgt gactgggaaa   1920
accctggcgt tacccaactt aatcgccttg cagcacatcc cccttttcgcc agctggcgta   1980 atagcgaaga ggcccgcacc gatcgccctt cccaacagtt gcgcagcctg aatggcgaat   2040
ggaaattgta agcgttaata ttttgttaaa attcgcgtta atttttgtt aaatcagctc   2100 attttttaac caataggccg aaatcggcaa aatcccttat aaatcaaaag aatagaccga   2160
gatagggttg agtgttgttc cagtttggaa caagagtcca ctattaaaga acgtggactc   2220
caacgtcaaa gggcgaaaaa ccgtctatca gggcgatggc ccactacgtg aaccatcacc   2280
ctaatcaagt ttttggggt cgaggtgccg taaagcacta atcggaacc ctaaagggag   2340 cccccgattt agagcttgac ggggaaagcc ggcgaacgtg gcgagaaagg aagggaagaa   2400
agcgaaagga gcggcgcta gggcgctggc aagtgtagcg gtcacgctgc gcgtaaccac   2460
cacacccgcc gcgcttaatg cgccgctaca gggcgcgtca ggtggcactt ttcggggaaa   2520
tgtgcgcgga acccctattt gtttatttt ctaaatacat tcaaatatgt atccgctcat   2580
gagacaataa ccctgataaa tgcttcaata atattgaaaa aggaagagta tgagtattca   2640
acatttccgt gtcgccctta ttccctttt tgcggcattt tgccttcctg ttttgctca   2700 cccagaaacg ctggtgaaag taaaagatgc tgaagatcag ttgggtgcac gagtgggtta   2760
catcgaactg gatctcaaca gcggtaagat ccttgagagt tttcgccccg aagaacgttt   2820
tccaatgatg agcactttta aagttctgct atgtggcgcg gtattatccc gtattgacgc   2880
```

```
cgggcaagag caactcggtc gccgcataca ctattctcag aatgacttgg ttgagtactc    2940
accagtcaca gaaaagcatc ttacggatgg catgacagta agagaattat gcagtgctgc    3000
cataaccatg agtgataaca ctgcggccaa cttacttctg acaacgatcg gaggaccgaa    3060
ggagctaacc gcttttttgc acaacatggg ggatcatgta actcgccttg atcgttggga    3120
accggagctg aatgaagcca taccaaacga cgagcgtgac accacgatgc ctgtagcaat    3180
ggcaacaacg ttgcgcaaac tattaactgg cgaactactt actctagctt cccggcaaca    3240
attaatagac tggatggagg cggataaagt tgcaggacca cttctgcgct cggcccttcc    3300
ggctggctgg tttattgctg ataaatctgg agccggtgag cgtgggtctc gcggtatcat    3360
tgcagcactg gggccagatg gtaagccctc ccgtatcgta gttatctaca cgacggggag    3420
tcaggcaact atggatgaac gaaatagaca gatcgctgag ataggtgcct cactgattaa    3480
gcattggtaa ctgtcagacc aagtttactc atatatactt tagattgatt taaaacttca    3540
tttttaattt aaaaggatct aggtgaagat cctttttgat aatctcatga ccaaaatccc    3600
ttaacgtgag ttttcgttcc actgagcgtc agaccccgta gaaaagatca aaggatcttc    3660
ttgagatcct ttttttctgc gcgtaatctg ctgcttgcaa acaaaaaaac caccgctacc    3720
agcggtggtt tgtttgccgg atcaagagct accaactctt tttccgaagg taactggctt    3780
cagcagagcg cagataccaa atactgtcct tctagtgtag ccgtagttag gccaccactt    3840
caagaactct gtagcaccgc ctacatacct cgctctgcta atcctgttac cagtggctgc    3900
tgccagtggc gataagtcgt gtcttaccgg gttggactca agacgatagt taccggataa    3960
ggcgcagcgg tcgggctgaa cggggggttc gtgcacacag cccagcttgg agcgaacgac    4020
ctacaccgaa ctgagatacc tacagcgtga gctatgagaa agcgccacgc ttcccgaagg    4080
gagaaaggcg gacaggtatc cggtaagcgg cagggtcgga acaggagagc gcacgaggga    4140
gcttccaggg ggaaacgcct ggtatcttta tagtcctgtc gggtttcgcc acctctgact    4200
tgagcgtcga ttttgtgat gctcgtcagg ggggcggagc ctatggaaaa acgccagcaa    4260
cgcggccttt ttacggttcc tggccttttg ctggccttt gctcacatgt tctttcctgc    4320
gttatcccct gattctgtgg ataaccgtat taccgccttt gagtgagctg ataccgctcg    4380
ccgcagccga acgaccgagc gcagcgagtc agtgagcgag gaagcggaag agcgcccaat    4440
acgcaaaccg cctctccccg cgcgttggcc gattcattaa tgcagctggc acgacaggtt    4500
tcccgactgg aaagcgggca gtgagcgcaa cgcaattaat gtgagttagc tcactcatta    4560
ggcacccag gctttacact ttatgcttcc ggctcgtatg ttgtgtggaa ttgtgagcgg    4620
ataacaattt cacacaggaa acagctatga ccatgattac gccaagctcg aaattaaccc    4680
tcactaaagg gaacaaaagc tgg                                            4703
```